(12) United States Patent
Davis et al.

(10) Patent No.: US 11,848,083 B2
(45) Date of Patent: *Dec. 19, 2023

(54) MEASURING REPRESENTATIONAL MOTIONS IN A MEDICAL CONTEXT

(71) Applicants: Massachusetts Institute of Technology, Cambridge, MA (US); Lahey Clinic Foundation, Inc., Burlington, MA (US)

(72) Inventors: Randall Davis, Weston, MA (US); Dana L. Penney, Weston, MA (US)

(73) Assignees: Massachusetts Institute of Technology, Cambridge, MA (US); Lahey Clinic Foundation Inc., Burlington, MA (US)

( * ) Notice: Subject to any disclaimer, the term of this patent is extended or adjusted under 35 U.S.C. 154(b) by 70 days.

This patent is subject to a terminal disclaimer.

(21) Appl. No.: 17/164,992

(22) Filed: Feb. 2, 2021

(65) Prior Publication Data

US 2021/0295969 A1 Sep. 23, 2021

Related U.S. Application Data

(63) Continuation of application No. 15/867,458, filed on Jan. 10, 2018, now Pat. No. 10,943,683, which is a
(Continued)

(51) Int. Cl.
*G16H 15/00* (2018.01)
*A61B 5/16* (2006.01)
(Continued)

(52) U.S. Cl.
CPC ............. *G16H 15/00* (2018.01); *A61B 5/165* (2013.01); *A61B 5/4088* (2013.01);
(Continued)

(58) Field of Classification Search
CPC ......... A61B 5/1124; A61B 5/16; A61B 5/165; A61B 5/4088; A61B 5/7264; G16H 15/00; G16H 50/00–70
See application file for complete search history.

(56) References Cited

U.S. PATENT DOCUMENTS 4,885,687 A 12/1989 Carey
4,922,925 A 5/1990 Crandall et al.
(Continued)

FOREIGN PATENT DOCUMENTS

ES 2161641 A1 12/2001
WO 2006088415 A1 8/2006

OTHER PUBLICATIONS

"Automatic Clock Drawing Test™—Times2Tell™—by Specialty Automated" (2006), pp. 1-15.
(Continued)

*Primary Examiner* — Thaddeus B Cox
(74) *Attorney, Agent, or Firm* — Bookoff McAndrews, PLLC

(57) ABSTRACT

A method includes receiving data representing graphomotor motion during a succession of executions of graphomotor diagnostic tasks performed in a medical context by a subject, processing the received data using a computer, including determining a first set of quantitative features from a first execution of a task by the subject, and determining a second set of quantitative features from a second execution of a task by the subject, determining one or more metrics based on a comparison to the successive executions, including using at least the first set of quantitative features and the second set of quantitative features to determine said metrics, and providing a diagnostic report associated with neurocognitive mechanisms underlying the subject's execution of the tasks based on the determined metrics.

20 Claims, 42 Drawing Sheets

Related U.S. Application Data continuation of application No. 13/920,270, filed on Jun. 18, 2013, now Pat. No. 9,895,085, which is a continuation-in-part of application No. 12/077,730, filed on Mar. 20, 2008, now Pat. No. 8,740,819.

(60) Provisional application No. 61/661,123, filed on Jun. 18, 2012, provisional application No. 60/919,338, filed on Mar. 21, 2007.

(51) Int. Cl.
```
G16H 50/00      (2018.01)
G16H 50/20      (2018.01)
G06Q 10/101     (2023.01)
G06Q 50/00      (2012.01)
A61B 5/00       (2006.01)
G16H 40/63      (2018.01)
```

(52) U.S. Cl.
CPC .......... *A61B 5/7264* (2013.01); *A61B 5/7475* (2013.01); *G06Q 10/101* (2013.01); *G06Q 50/01* (2013.01); *G16H 40/63* (2018.01); *G16H 50/00* (2018.01); *A61B 5/002* (2013.01); *G16H 50/20* (2018.01)

(56) References Cited

U.S. PATENT DOCUMENTS

| | | | |
|---|---|---|---|
| 5,022,086 A | 6/1991 | Crane et al. | |
| 5,772,611 A | 6/1998 | Hocherman | |
| 5,885,231 A | 3/1999 | Cramer et al. | |
| 5,888,074 A | 3/1999 | Staplin et al. | |
| 5,956,020 A | 9/1999 | D'Amico et al. | |
| 6,018,336 A | 1/2000 | Akiyama et al. | |
| 6,090,044 A | 7/2000 | Bishop et al. | |
| 6,115,024 A | 9/2000 | Hayama | |
| 6,280,198 B1 | 8/2001 | Calhoun et al. | |
| 6,350,032 B1 | 2/2002 | Menozzi et al. | |
| 6,454,706 B1 | 9/2002 | Pullman | |
| 6,517,480 B1 | 2/2003 | Krass | |
| 6,546,134 B1 | 4/2003 | Shrairman et al. | |
| 7,267,440 B2 | 9/2007 | Poreh et al. | |
| 7,294,107 B2 | 11/2007 | Doniger et al. | |
| 7,636,457 B2 | 12/2009 | Franke et al. | |
| 8,016,416 B1 | 9/2011 | Straus | |
| 8,407,625 B2 | 3/2013 | Cohen et al. | |
| 2003/0059759 A1 | 3/2003 | Calhoun et al. | |
| 2003/0223038 A1 | 12/2003 | Alster et al. | |
| 2004/0081945 A1 | 4/2004 | Reeves et al. | |
| 2004/0152995 A1 | 8/2004 | Cox et al. | |
| 2004/0167380 A1 | 8/2004 | Simon | |
| 2004/0229198 A1 | 11/2004 | Boyd et al. | |
| 2005/0019734 A1 | 1/2005 | Peled | |
| 2005/0142524 A1 | 6/2005 | Simon et al. | |
| 2005/0187436 A1 | 8/2005 | Doniger et al. | |
| 2005/0225720 A1 | 10/2005 | Ridings et al. | |
| 2005/0273017 A1 | 12/2005 | Gordon | |
| 2005/0288571 A1 | 12/2005 | Perkins et al. | |
| 2006/0189903 A1 | 8/2006 | Poreh et al. | |
| 2006/0210112 A1 | 9/2006 | Cohen et al. | |
| 2006/0240393 A1 | 10/2006 | Reeves et al. | |
| 2006/0271640 A1 | 11/2006 | Muldoon et al. | |
| 2008/0009772 A1 | 1/2008 | Tyler et al. | |
| 2008/0039698 A1 | 2/2008 | Burton | |
| 2008/0200796 A1 | 8/2008 | Graham et al. | |
| 2008/0243033 A1* | 10/2008 | Davis .................. | A61B 5/7475 600/595 |
| 2008/0280276 A1 | 11/2008 | Raber et al. | |
| 2008/0312958 A1 | 12/2008 | Sachs et al. | |
| 2012/0095363 A1 | 4/2012 | Garner | |
| 2012/0172682 A1 | 7/2012 | Linderman et al. | |
| 2014/0031724 A1 | 1/2014 | Davis et al. | |
| 2014/0113258 A1 | 4/2014 | Degoede et al. | |

OTHER PUBLICATIONS

"Clock Drawing Task," Mar. 2006. pp. 1-3.

CogState [online], [retrieved on Jan. 26, 2007] Retrieved from the Internet URL: http://cogstate.com/index.php?sectioniD=OPageiD=4319.

Davies et al., "An Investigation into the Measurement of Driver Impairment at the Roadside Using a Logitech Digital Pen," 17th International Conference on Alcohol, Drugs and Traffic Safety Glasgow, UK (2004).

Diegelman et al., "Validity of the Clock Drawing Test in Predicting Reports on Driving Problems in the Elderly," BMC Geriatrics 4(10) (2004).

Freedman et al., "Clock Drawing: A Neuropsychological Analysis," p. 44 (NY: Oxford University Press, Inc.) (1994).

Instruments for Clinical Health-Care Research 100 (Marilyn Frank-Stromborg & Sharon J Olsen eds., Jones and Bartlett Publishers, Inc. 1997) (1992).

Shah, "Only Time Will Tell: Clock Drawings as an Early Indicator of Neurological Dysfunction," P&S Medical Review, 30-34 (2001).

Stillings et al., Cognitive Science: An Introduction, p. 306 (Massachusetts Institute of Technology 2nd ed, 1998) (1995).

Straus, "Use of the automatic clock drawing test to rapidly screen for cognitive impairment in older adults, drivers, and the physically challenged," J. Am. Geriatr. Soc., Feb. 2007, 55(2):310-1. (Year: 2007).

Tiplady et al., "Development of Tests of Psychological Performance Using a Digital Pen," Proceedings of the British Psychological Society, 12: 72 (2004).

Tiplady et al., "Use of a Digital Pen to Administer a Psychomotor Test," [online], [retrieved on Feb. 15, 2007] Retrieved from the Internet URL: http://www.penscreen.com/Tiplady%2020036%20BAP%20Pen%20Poster.pdf.

Tiplady et al., "Use of a Digital Pen to Administer a Psychomotor Test," Journal of Psychopharmacology 17 (Supp. 3), A71 (2003).

Wilson et al., "Computer-Based Assessment in Neuropsychology," In a Handbook of Neuropsychological Assessment, John R. Crawford et al., eds. (Lawrence Erlbaum, Assocs. Ltd.), pp. 413-431 (1992).

Wilson et al., "Neuropsychological Assessment in Alcohol, Drug Abuse and Toxic Conditions," In a Handbook of Neuropsychological Assessment, John R. Crawford et al., eds. (Lawrence Erlbaum, Assocs. Ltd.), pp. 323-337 (1992).

* cited by examiner

TABLE 1

Spreadsheet of Detailed Analysis of Classified Clock Drawing

MetaData
Patient Name(Last, First)           Doe           Jane
Doctor Name(Last, First)
Clinic ID                           LN19
Drawing
Drawing Type                        COMMAND
# of Strokes                        43
Time(s)                             16.002
Clockface(s)
Strokes                           1
Time(s)                             1.493
Length(mm)                          302.2048302
Avg. Pen Speed 1st Quarter(mm/s)    107.3864839
Avg. Pen Speed 2nd Quarter(mm/s)    291.2080343
Avg. Pen Speed 3rd Quarter(mm/s)    274.9512737
Avg. Pen Speed 4th Quarter(mm/s)    136.9220223
Horizontal Diameter(mm)             98.7
Vertical Diameter(mm)               79.425
Fitted Horizontal Diameter(mm)      79.21503761
Fitted Vertical Diameter(mm)        98.29411028
Horizontal Symmetry                 37.46124906
Vertical Symmetry                   79.425
Ellipse Horizontal Symmetry         29.54644081
Ellipse Vertical Symmetry           45.89609075
Closed Curve %                      8.79775E−05
Closed Curve Angle                  −21.93603052
Ellipse Angle                       84.43858889
Center: X(mm)                       431.6808079
Center: Y(mm)                       91.5418925
Hour Hands                          1
Strokes                           1
Time(s)                             1.506
Total Length (mm)                   37.44648939
Hand Length(mm)                     24.45304812
Center: X(mm)                       451.0511054
Center: Y(mm)                       83.03457527

FIG. 23a

TABLE 1 - Continued

Spreadsheet of Detailed Analysis of Classified Clock Drawing

| | | | |
|---|---|---|---|
| Direction of Stroke | 1 | | |
| Direction of Arrowhead | 1 | | |
| Distance from Center(mm) | 1.6410955 | | |
| Angle | 18.87952403 | | |
| Difference from Ideal Angle | 131.120476 | | |
| Minute Hands | 1 | | |
| # Strokes | 4 | | |
| Time(s) | 15.918 | | |
| Total Length (mm) | 84.69232851 | | |
| Hand Length(mm) | 27.36688236 | | |
| Center: X(mm) | 422.1427668 | | |
| Center: Y(mm) | 70.91232523 | | |
| Direction of Stroke | 1 | | |
| Direction of Arrowhead | 1 | | |
| Distance from Center(mm) | 1.87223277 | | |
| Angle | 111.7139351 | | |
| Difference from Ideal Angle | −81.71393508 | | |
| Hand Pairs | | | |
| Hour Hand | 1 | | |
| Minute Hand | 1 | | |
| Intersection X(mm) | 430.370706 | | |
| Intersection Y(mm) | 90.27699518 | | |
| Angle between Hands | −92.83441105 | | |
| Number Analysis | | | |
| Missing | | | |
| Order Drawn In | 12 | 6 | 9 |
| Order Drawn In (Cont.) | 3 | 1 | 2 |
| Order Drawn In (Cont.) | 4 | 5 | 7 |
| Order Drawn In (Cont.) | 8 | 10 | 11 |
| Avg[.] Width(mm) | 7.346875 | | |
| Avg[.] Height(mm) | 8.403125 | | |
| Numbers | 12 | 6 | 9 |
| # Strokes | 2 | 1 | 1 |
| Time(s) | 0.712 | 0.48 | 0.413 |
| Length(mm) | 27.20432645 | 22.32754048 | 23.5459184 |
| Center: X(mm) | 438.0562452 | 428.5005813 | 393.8026 |
| Center: Y(mm) | 58.54151905 | 124.0437406 | 86.08662963 |
| Width(mm) | 12.75 | 5.8875 | 6.1125 |
| Height(mm) | 6.3375 | 8.55 | 9.6 |
| Outside Clockface | 0 | 0 | 0 |
| Angle | 77.5842539 | 263.5759801 | 174.8192988 |
| Difference from Ideal Angle | −12.4157461 | −6.4240199 | −5.180701174 |

FIG. 23b

TABLE 1 - Continued

Spreadsheet of Detailed Analysis of Classified Clock Drawing

| | | | |
|---|---|---|---|
| Center: Y(mm) | 109.6718792 | 74.00183529 | 64.85114237 |
| Width(mm) | 4.5 | 7.9875 | 10.65 |
| Height(mm) | 11.55 | 6.7875 | 8.5875 |
| Outside Clockface | 0 | 0 | 0 |
| Angle | 204.6800976 | 147.355377 | 118.5462213 |
| Difference from Ideal Angle | −5.319902433 | −2.644622978 | −1.453778678 |
| Distance from Circumference(mm) | 10.7985025 | 10.00080075 | 10.23009691 |

FIG. 23c

MEASURING REPRESENTATIONAL MOTIONS IN A MEDICAL CONTEXT

CROSS-REFERENCE TO RELATED APPLICATIONS

This application is a continuation of U.S. application Ser. No. 15/867,458, filed Jan. 10, 2018, which is a continuation of U.S. patent application Ser. No. 13/920,270, filed Jun. 18, 2013, now U.S. Pat. No. 9,895,085, which is a continuation-in-part of U.S. application Ser. No. 12/077,730, filed on Mar. 20, 2008, now U.S. Pat. No. 8,740,819, which claims the benefit of U.S. Provisional Application No. 60/919,338, filed on Mar. 21, 2007. U.S. patent application Ser. No. 13/920, 270 also claims the benefit of U.S. Provisional Application No. 61/661,123, filed on Jun. 18, 2012. The entire teachings of the above applications are incorporated herein by reference.

BACKGROUND

This description relates to measuring representational motions in a medical context.

Neuropsychological tests can be used to test a particular psychological characteristic of a person, and, in so doing, the test provides additional information about the person's neurological functions as related to the tested psychological characteristic. Neil A. Stillings et. al., Cognitive Science: An Introduction 306 (Massachusetts Institute of Technology 2nd ed. 1998) (1995). Neuropsychological tests may be administered by a proctor in an isolated setting, which is ideal because the isolated setting allows for an optimum level of observing a person's cognitive abilities. See Instruments for Clinical Health-Care Research 100 (Marilyn Frank-Stromborg & Sharon J. Olsen eds., Jones and Bartlett Publishers, Inc. 1997) (1992). There are a myriad of neuropsychological tests that may be used, which include, but are not limited to, the following: the Rey-Osterreith Complex Figure, Mini-Mental State Examination, Wechsler Memory Scale, or the Clock Drawing Test. Id. at 86-112. Each test can be administered by a proctor, which can be a nurse, doctor, or other person with requisite training or background. Id. at 100. To interpret results of a neuropsychological test, an during the testing as well the examinee's background (e.g., medical history, education, occupation, etc.) and process approach to the test, and then consider these characteristics in the context of normative standards. Id. at 100-01.

SUMMARY

While current use of neuropsychological tests is widespread, problems exist, which include reproducibility of test settings and standardization of test scores. For example, in current practice, a person may be asked to perform a neuropsychological test by a technician or nurse, and the technician or nurse then gives a doctor the completed test for analysis and assessment. In this example, the doctor is unable to observe the person's planning and implementation to complete the test, which means that the doctor loses substantive process data useful in assessing the person's cognitive condition.

Additionally, current practice of neuropsychological testing leaves room for qualitative interpretation of what the completed test means. For example, with the Clock Drawing Test (CDT), a slightly misshaped clock frame may not signify a neurological deficit to one medical practitioner, but may represent as well as allow for early detection and prevention of a neurological disease to another medical practitioner who is trained in the process approach to test interpretation.

While automated cognitive testing is currently developing, such as testing using automated programs on computers, mobile phones, tablet computers, and touchscreens, such use changes the administration of the neuropsychological test. For example, with the CDT, allowing a person to draw the clock and place the time solely using a touchscreen may materially alter the test because the person is not using a writing utensil and paper to perform the test. Also, automated testing of cognitive changes of a person based upon alcohol or drug consumption is being researched. Such testing is being done to assess and observe the transient effects that alcohol and drugs have on a person's cognitive abilities. The alcohol and drug research is not being done to assess and observe the person's response to the test and what the same represents regarding the person's neurological functions and capabilities.

Example embodiments presented in the present disclosure allow for both of the aforementioned cognitive tests while not materially altering the testing apparatus. The same or other embodiments account for the neurological functions and capabilities of a person based upon their response to neuropsychological testing, while simultaneously providing a means to precisely capture and quantify qualitative characteristics of standardized neuropsychological testing.

The summary that follows details some of the embodiments included in this disclosure. The information is proffered to provide a fundamental level of comprehension of aspects of this disclosure.

One or more embodiments comprise receiving data representing graphomotor motion during a succession of executions of graphomotor diagnostic tasks performed in a medical, diagnostic, or other assessment (e.g., in school, at home, at work, and so on) context by a subject. The received data is processed using a computer. This processing includes determining a first set of quantitative features from a first execution of a task by the subject, and determining a second set of quantitative features from a second execution of a task by the subject. One or more metrics are determined based on a comparison to the successive executions, including using at least the first set of quantitative features and the second set of quantitative features to determine said metrics. A diagnostic report associated with neurocognitive mechanisms underlying the subject's execution of the tasks is provided based on the determined metrics.

Another embodiment of the present disclosure includes an apparatus for and a corresponding method of measuring representational motions made by a person in any assessment context, with medical as one such context. One embodiment includes (i) capturing with spatial precision individual representational motions made by a person in a medical context in a form of representations that signify neurocognitive mechanisms underlying the motions and (ii) reporting information based on the representations of the individual representational motions. For example, this embodiment may be used in assessment across the lifespan of a person, including children through geriatric, and in a variety of settings, including schools, rehabilitation centers, and clinics.

The apparatus for or method of measuring representational motions made by a person in a medical context may include capturing the individual representational motions while logging timestamps corresponding to the individual representational motions. The apparatus and method may also permit logging timestamps while recording with temporal precision, where the timestamps may be real-time timestamps that indicate the times at which the person made the individual representational motions.

The apparatus for or method of measuring representational motions made by a person in a medical context may include capturing the individual representational motions under multiple conditions. The multiple conditions may include capturing with spatial precision individual representational motions made by the person in at least one of the following conditions: free-drawn, pre-drawn (or copy), or completion.

In accordance with the present disclosure, "spatial precision" may be defined by capturing the individual representational motions within a tolerance recognized as acceptable to measure accurately an individual representational motion by the person in the medical context. Also, "medical context" may include at least one of the following conditions: neuropsychological, neurological, neurogenetic, geriatric, developmental or general health. The medical context may also include clinical evaluation of therapeutic interventions or diagnostic purposes. The medical context may also include at least one of the following settings: medical, academic, rehabilitation, screening clinics.

In accordance with the present disclosure, "information" based on the representations of the individual representational motions may include at least one of the following: at least one property of the representations, a metric based on at least one of the representations, a diagnosis, or representations of the individual representational motions. Additionally, a "diagnosis" may include a list of potential diagnoses, a list of observations, or a list of observations and corresponding potential diagnoses.

The apparatus for or method of measuring representational motions made by a person in a medical context may also include measuring at least one property of the individual representational motions. As used herein, measuring the at least one property of the individual representational motions includes measuring at least one of the following: at least one characteristic of a stroke of an individual representational motion, segment of an individual representational motion, multiple individual representational motions, or transition between at least two individual representational motions made by the person.

The apparatus for or method of measuring representational motions made by a person in a medical context may also include reporting information about the person corresponding to the medical context as a function of at least one property. As used in the present disclosure, reporting information about the person corresponding to the medical context as a function of at least one property includes calculating a metric as a function of (i) data representing the individual representational motions produced by capturing the individual representational motions and (ii) (a) data representing known standards corresponding to the individual representational motions or (b) data empirically measured in the past representing the same or similar representational motions made by the person or at least one other person. Reporting information about the person corresponding to the medical context as a function of at least one property may also include determining a pass/fail result or an incremental difference from the expected standard (i.e., based on normative standards or the person's previously established unique baseline from prior use of the example embodiment). The pass/fail result or incremental difference may be based on the at least one property of the individual representational motions with respect to at least one criterion. Additionally, reporting information about the person corresponding to the medical context as a function of at least one property may include producing a tabular array of multiple metrics of the at least one property. Reporting information about the person corresponding to the medical context as a function of at least one property may also include transmitting the at least one property via either a local or wide area network.

The apparatus for or method of measuring representational motions made by a person in a medical context may include capturing individual representational motions by digitizing handwritten motions. Digitizing handwritten motions may include digitizing handwritten motions made by the person in producing graphical figures or text or in producing a visible, physical mark. Digitizing the handwritten motions may further include collecting data from a digitizing stylus used by the person in performing the handwritten motions. Collecting the data from the digitizing stylus may also include collecting data corresponding to positioning the digitizing stylus relative to material comprising self-identifying marks correlating to spatial locations on or in the material. Additionally, capturing the individual representational motions may include digitizing motion of a body part of the person in connection with an activity other than or in addition to handwritten motions.

As used in the present disclosure, "individual representational motions" may be defined by at least one of the following: change in position of an appendage of the person relative to a reference point, acceleration, rate, time of making an individual representational motion relative to other individual representational motions, starting and ending positions relative to expected positions, or via point positions relative to expected via point positions between a starting position and an ending position.

The apparatus for or method of measuring representational motions made by a person in a medical context may further include displaying the individual representational motions as a single collective image.

The apparatus for or method of measuring representational motions made by a person in a medical context may also further include displaying the individual representational motions in a chronological sequence. The apparatus for or method may also further include interactively displaying the individual representational motions in a chronological sequence in real-time, fast forward mode, or slow motion mode.

The apparatus for or method of measuring representational motions made by a person in a medical context may further comprise analyzing the individual representational motions based on the spatial precision of the individual representational motions, at least one property of the individual representational motions, or a metric calculated as a function of at least one of the individual representational motions. As used herein, analyzing the individual representational motions may include classifying the individual representational motions according to the medical context. Additionally, analyzing the individual representational motions may include analyzing the individual representational motions based on a chronological sequence by which the person made the individual representational motions. Analyzing the individual representational motions may also include classifying the individual representational motions based on geometric properties of the individual representational motions. At least one property of the individual representational motions may include temporal properties and analyzing the individual representational motions may include classifying the individual representational motions based on the temporal properties of the individual representational motions. The at least one "property" of the individual representational motions may include geometric properties and temporal properties. Also, analyzing the individual representational motions may include classifying the individual representational motions based on a combination of the geometric and temporal properties of the individual representational motions.

The apparatus for or method of measuring representational motions made by a person in a medical context may further comprise accepting user indications of misclassifications and user indications of correct classifications of the individual representational motions.

Additionally, as used in some embodiments of the present disclosure, analyzing the individual representational motions includes analyzing the individual representational motions based on a chronological sequence by which the person made the individual representational motions, including pauses between individual representational motions. Analyzing the individual representational motions may also include analyzing angular displacements or at least one geometrical relationship between (i) a given individual representational motion at two moments or periods in time, (ii) two different individual representational motions, or (iii) an individual representational motion and a fixed location relative to the individual representational motion. Analyzing the individual representational motions may also include analyzing transitions between the individual representational motions.

The apparatus for or method of measuring representational motions made by a person in a medical context may further comprise calculating at least one metric of at least one property and generating a report of the at least one metric.

The apparatus for or method of measuring representational motions made by a person in a medical context may further comprise transmitting at least one of the following about the individual representational motions made by the person: representations of the individual representational motions; measurements of at least one property of the individual representational motions; reports of a metric of at least one property; or images, either single image or a chronological sequence, of the individual representational motions.

The apparatus for or method of measuring representational motions made by a person in a medical context may further include adding data to a database about the individual representational motions made by the person. As used herein, "data" may include at least one of the following: data based on the individual representational motions, stroke classification, stroke splitting points, or stroke origination points.

The apparatus for or method of measuring representational motions made by a person in a medical context may further include responding to queries to the database with data about the individual representational motions made by the person.

The apparatus for or method of measuring representational motions made by a person in a medical context may further include collecting fees to access the data in the database. Collecting fees may also include collecting fees in the form of subscription service fees.

The apparatus for or method of measuring representational motions made by a person in a medical context may further include reporting information about the individual representational motions as a function of at least one property. Reporting information about the individual representational motions as a function of at least one property may also include calculating a metric as a function of (i) data representing the individual representational motions produced by capturing the individual representational motions and (ii) (a) data representing known standards corresponding to the individual representational motions or (b) data empirically measured in the past representing the same or similar representational motions made by the person or at least one other person. Additionally, reporting information about the individual representational motions as a function of at least one property may also include determining a pass or fail result based on the at least one property of the individual representational motions with respect to at least one criterion. Reporting information about the individual representational motions as a function of at least one property may also include producing a tabular array of multiple metrics of the at least one property or transmitting the at least one property via either a local or wide area network.

The apparatus for or method of measuring representational motions made by a person in a medical context may be performed in at least one of the following settings: a medical facility or a school. Additionally, the apparatus for or method of measuring representational motions made by a person in a medical context may be performed under supervision of a medical practitioner or in an absence of a medical practitioner.

The apparatus for or method of measuring representational motions made by a person in a medical context may further include identifying motor or cognitive skill changes in the person at an early stage of a cause of either the motor or cognitive skill changes, respectively. The apparatus for or method of measuring representational motions made by a person in a medical context may further include identifying motor or cognitive skill changes of the person in a longitudinal study or non-longitudinal study, such as a single day study.

The apparatus for or method of measuring representational motions made by a person in a medical context may further include identifying whether to adjust a pharmaceutical dosage administered to the person.

The apparatus for or method of measuring representational motions made by a person in a medical context may further include identifying whether to adjust treatment administered to the person. Additionally, the apparatus for or method of measuring representational motions made by a person in a medical context may further include contributing to a differential diagnosis or identifying additional tests useful in establishing a diagnosis. The apparatus for or method of measuring representational motions made by a person in a medical context may further include identifying changes of implantable interventions (e.g., deep brain stimulator) in the person, changing parameters of the implantable interventions in the person, identifying medical treatment changes (e.g., changes in medications), or monitoring changes in the medical condition.

The apparatus for or method of measuring representational motions made by a person in a medical context may be performed on a control group and a test group and may include calculating metrics as a function of at least one property for the control group and the test group and optionally further including developing a standard for domestic or international application based on the metrics associated with the control and test groups.

In another aspect, in general, a computer implemented method includes receiving data representing graphomotor motion during a succession of executions of graphomotor diagnostic tasks performed in a medical context by a subject, processing the received data using a computer, including determining a first set of quantitative features from a first execution of a task by the subject, and determining a second set of quantitative features from a second execution of a task by the subject, determining one or more metrics based on a comparison to the successive executions, including using at least the first set of quantitative features and the second set of quantitative features to determine said metrics, and providing a diagnostic report associated with neurocognitive mechanisms underlying the subject's execution of the tasks based on the determined metrics.

Aspects may include one or more of the following features.

The graphomotor diagnostic tasks may include maze-following tasks. The maze-following tasks may include a first maze following task corresponding to the first set of quantitative features, and a second maze-following task corresponding to the second set of quantitative features. The second maze-following task may be executed after the first maze-following task, and the first and second maze following tasks may share a common solution, and the second maze following task may have a greater number of decision points in the solution than the first maze following task.

The first set of quantitative features may include an execution time for the first task and the second set of quantitative features may include an execution time for the second task, and wherein the one or more metrics may include a comparison of said execution times. The second maze-following task may include one or more decision points and the second set of quantitative features may include a characterization of a decision making time at the one or more decision points, a characterization of incorrect decisions made at the one or more decision points, and/or a characterization of over-corrections made in response to incorrect decisions made at the one or more decision points. Each decision point of the one or more decision points may be associated with a local characterization of a decision making time at the decision point, a local characterization of incorrect decisions made at the decision point, and/or a local characterization of over-corrections made in response to incorrect decisions made at the decision point.

The graphomotor diagnostic tasks may include clock drawing tasks. Processing the received data using a computer may include determining a first set of qualitative features from the first execution of the task by the subject, and determining a second set of qualitative features from the second execution of the task by the subject; and determining the one or more metrics based on the comparison to the successive executions, may include using at least the first set of qualitative features and the second set of qualitative features to determine said metrics. The first set of quantitative features may include a rate of occurrence of graphomotor motion elements during the first execution of the task and the second set of quantitative features may include a rate of occurrence of graphomotor motion elements during the second execution of the task. The graphomotor motion elements may include hooklets.

In another aspect, in general, a computer implemented method includes receiving data representing graphomotor motion during an execution of a graphomotor diagnostic task performed in a medical context by a subject, the graphomotor diagnostic task including one or more decision points, processing the received data using a computer, including determining a first set of quantitative features from the execution of the task by the subject, the first set of quantitative features characterizing the motion in a vicinity of the one or more decision points, processing prior data characterizing motion during one or more prior executions of the diagnostic task to determine a second set of quantitative features from the one or more prior executions of the task, the second set of quantitative features characterizing the motion of the one or more prior executions of the diagnostic task in a vicinity of the one or more decision points, determining one or more metrics based on a comparison to the prior executions, including using at least the first set of quantitative features and the second set of quantitative features to determine said metrics, and providing a diagnostic report associated with neurocognitive mechanisms underlying the subject's execution of the tasks based on the determined metrics.

Aspects may include one or more of the following features.

The first set of quantitative features may include a decision making time in the vicinity of each of the one or more decision points during the execution of the task and the second set of quantitative features may include a representation of a decision making time in the vicinity of each of the one or more decision points during the one or more prior executions of the task. The first set of quantitative features may include an overall execution time for the task and the second set of quantitative features may include a representation of overall execution times for the one or more prior executions of the task.

The first set of quantitative features may include a characterization of incorrect decisions made in the vicinity of the one or more decision points during the execution of the task and/or a characterization of over-corrections made in response to incorrect decisions made in the vicinity of the one or more decision points during the execution of the task, and the second set of quantitative features may include a characterization of incorrect decisions made in the vicinity of the one or more decision points during the one or more prior executions of the task and/or a characterization of over-corrections made in response to incorrect decisions made in the vicinity of the one or more decision points during the one or more prior executions of the task.

At least some of the decision points may be embedded decision points. The graphomotor diagnostic task may include a maze-following task and the one or more decision points may include branch points in the maze drawing task. At least some of the one or more decision points may include a different number of branch points than at least some other decision points of the one or more decision points. For each of at least some of the decision points, at least one of the branch points associated with the decision point may lead to another, adjacent decision point and at least one of the branch points may lead to a dead end in the maze and a distance from the decision point to the adjacent decision point may be equal to a distance from the decision point to a dead end associated with the decision point.

The first set of quantitative features may include a rate of occurrence of graphomotor motion elements during the execution of the task and the second set of quantitative features may include a rate of occurrence of graphomotor motion elements during the one or more prior executions of the task. The graphomotor motion elements may include hooklets.

Advantageously, measuring dynamic characteristics of the subject's performance during a diagnostic task enables detection and tracking of cognitive errors even when the subject's performance appears to be correct to an expert (e.g., a doctor) who is observing the subject.

DESCRIPTION OF DRAWINGS

FIG. 23*a*-FIG. 23*c* is a table showing a result of an analysis of a clock drawing.

DESCRIPTION

A description of example embodiments of the invention follows.

A Clock Drawing Test (CDT) may be used to evaluate neurocognitive processes that are important in a variety of medical conditions, such as dementia, by a health care professional because the CDT may allow an examiner to observe cognitive mechanisms and dysfunctions of a person based upon the person's performance. Morris Freedman et. al., Clock Drawing: A Neuropsychological Analysis 44 (Oxford University Press, Inc. 1994). The CDT may also be used to examine numerous conditions that includes, but is not limited to other dementias and a spectrum of neurological disorders, such as "metabolic encephalopathy, traumatic brain injury, and disconnection syndromes." Id. at 77. The CDT has been used to test visuoconstructive, visuospatial, visuomotor, visuoperceptual, or auditory processing functions or abilities of a person. Id. at 3-5. The CDT has three conditions, which are: (i) clock drawing, (ii) clock setting, and (iii) clock reading. Instruments for Clinical Health-Care Research at 89. The CDT may sound simplistic in nature, but it requires the use of several regions of the brain. Clock Drawing at 4. For example, when the person receives an auditory command to "draw a clock," the person must have sufficient auditory skills to understand the request as well as possess a representation of a clock in the person's memory, along with a means to retrieve such information. Id. The person must also possess the visuoperceptual and visuomotor processes necessary to create the retrieved memory. Id. The person's ability to plan, strategize, and implement the plan or strategy may also be observed. Clock Drawing at 5. The CDT may be used to "demonstrate deficits due to dysfunction in specific brain systems that may be affected by a broad spectrum of neurological disorders." Id. at 78. For example, a study found that the CDT may be "used to distinguish between neurological conditions." Id. at 98.

Additionally, the CDT requires the concurrent use of neurocognitive processes. Id. For example, in order for the person to draw the clock, he or she must place the numbers on the clock face while observing the spatial arrangement of the clock. Id. Also, the person's executive functions, such as, planning, organization, and simultaneous processing, are necessary for the person to perform multiple steps to create the clock. Id. If the person must place a specific time on the clock, the person's memory skills are used to store the information and to recover the specific time from the person's memory once the clock face and numbers have been created. Id. Each of the previously mentioned requirements are controlled by different regions of the brain, which include: cortical and subcortical, anterior and posterior, and left and right cerebral hemispheres. Id. Any suboptimal performance of the different regions of the brain will yield a different clock drawing. Id.

Figure 1:
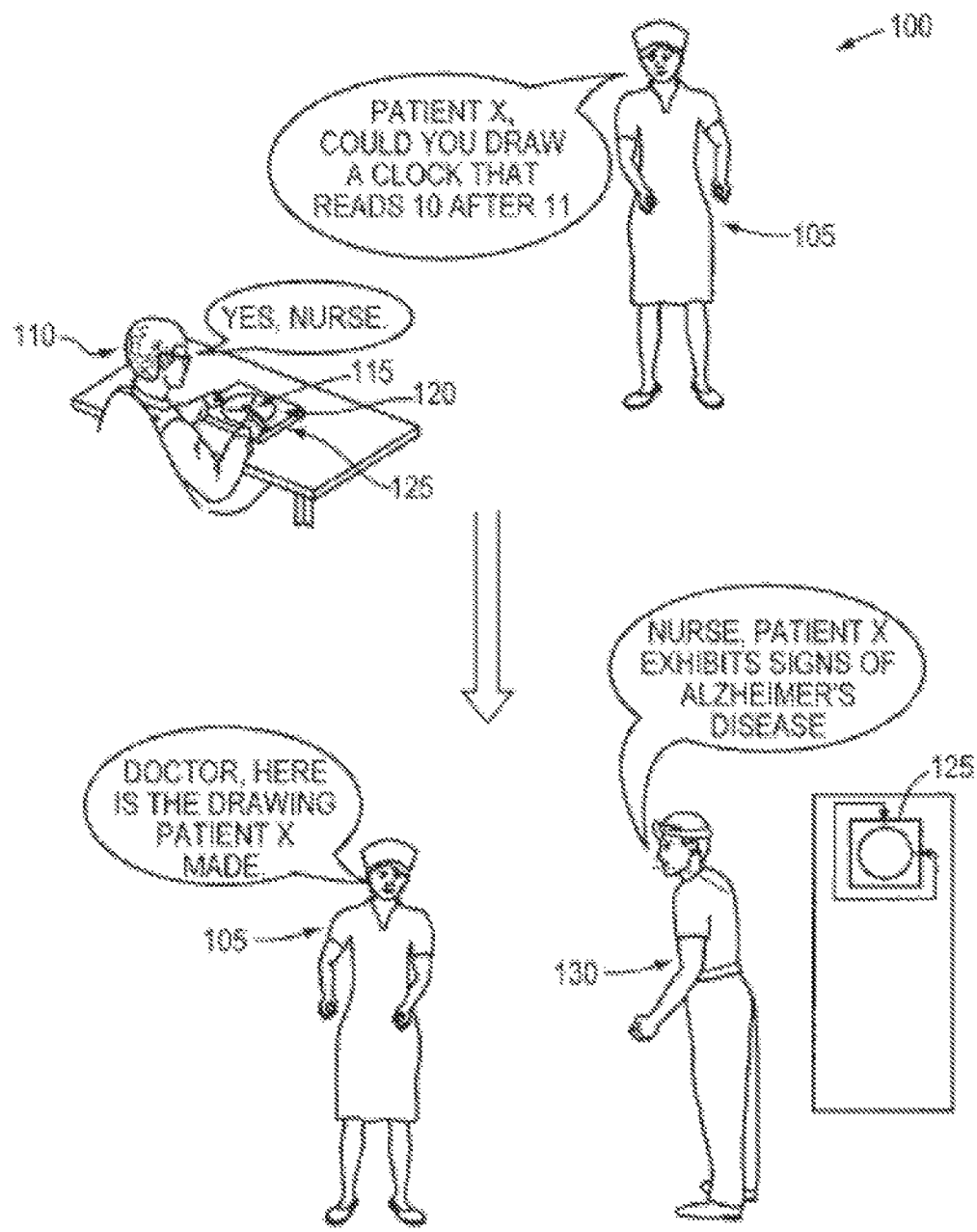
FIG. 1 is an example illustration of the administration of a neuropsychological test as administered under current practice and upon which a medical practitioner performs an analysis or diagnosis of the person.

FIG. 1 is an example illustration of the administration of a neuropsychological test as administered under current practice and upon which a medical practitioner performs an analysis and diagnosis of the person 100. In FIG. 1, a nurse 105 administers a CDT to a person 110. There are several variations or conditions of administering the CDT. One variation is to give a person a blank sheet of paper, ask the person to draw a clockface, and then draw the hands showing a particular time on the clock. Id. at 47-48. Another variation is to give the person a pre-drawn clock and to instruct the person to draw a specified time on the clock, which may be done with one specified time or multiple times. Id. at 48. In some instances, when an examinee is asked to draw a specific time in a clock face, the examinee may write the literal version of the request, such as drawing a "10" after an "11" when requested to draw "10 after 11" Id. at 28. Such an error may signify that the examinee made "a concrete interpretation of the [examiner's] instructions and is suggestive of frontal system dysfunction." Id. An additional variation is to present the person with a completely pre-drawn clock and to instruct the person to copy the clock exactly as it appears. Id. at 6-7. Each variation has similar attributes, but also "differ[s] in the clinical information they provide." Id. at 77.

In FIG. 1, the person 110 is instructed by the nurse 105 to draw a face of an analog clock at a specific time using a writing utensil 115 and a sheet of paper 120, as explained above in reference to the first variation. The nurse 105 collects the drawing 125 once completed by the person 110, which the nurse then gives to the doctor 130. The doctor 130 reviews the drawing 125 and establishes an opinion.

Figure 2A:
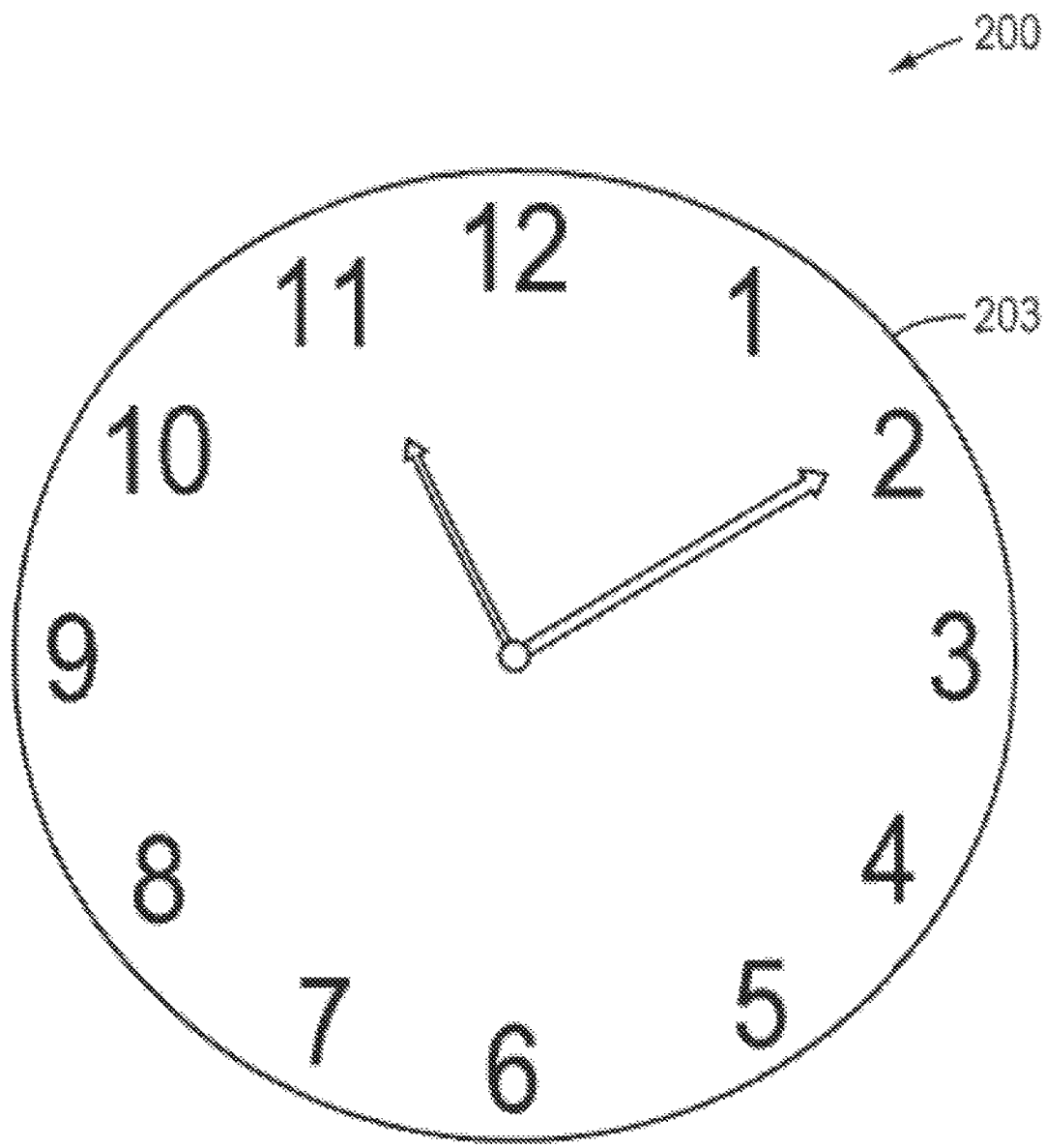
FIG. 2A is an illustration of a completed Clock Drawing Test that may be received under current practice and procedure.

FIG. 2A is a clock diagram illustrating a result (i.e., clock 200) of a CDT that may be received under current practice and procedure. In current practice, a medical practitioner may request that a person use a writing utensil, such as a pencil, pen, marker, crayon, colored pencil, or the like, and a piece of paper. The practitioner may or may not watch the person as he or she creates a clock face 203. There are several problems with current practice and procedure of administrating the CDT. For example, if the person receives an audible command, by not observing the person as he or she creates the clock, the medical practitioner does not receive substantive data regarding the person's auditory processing of information, which relates to linguistic functions of the brain. Clock Drawing at 4. Additionally, if the person experiences a delay or a pause in creating the clock, which may relate to frontal lobe functions if they have trouble with initiating behavior, temporal lobe functions if associated with memory (right and left temporal) and language (left temporal) functions of the brain, the medical practitioner is not informed of such based upon the completed clock 200. See Clock Drawing at 6.

Figure 2B:
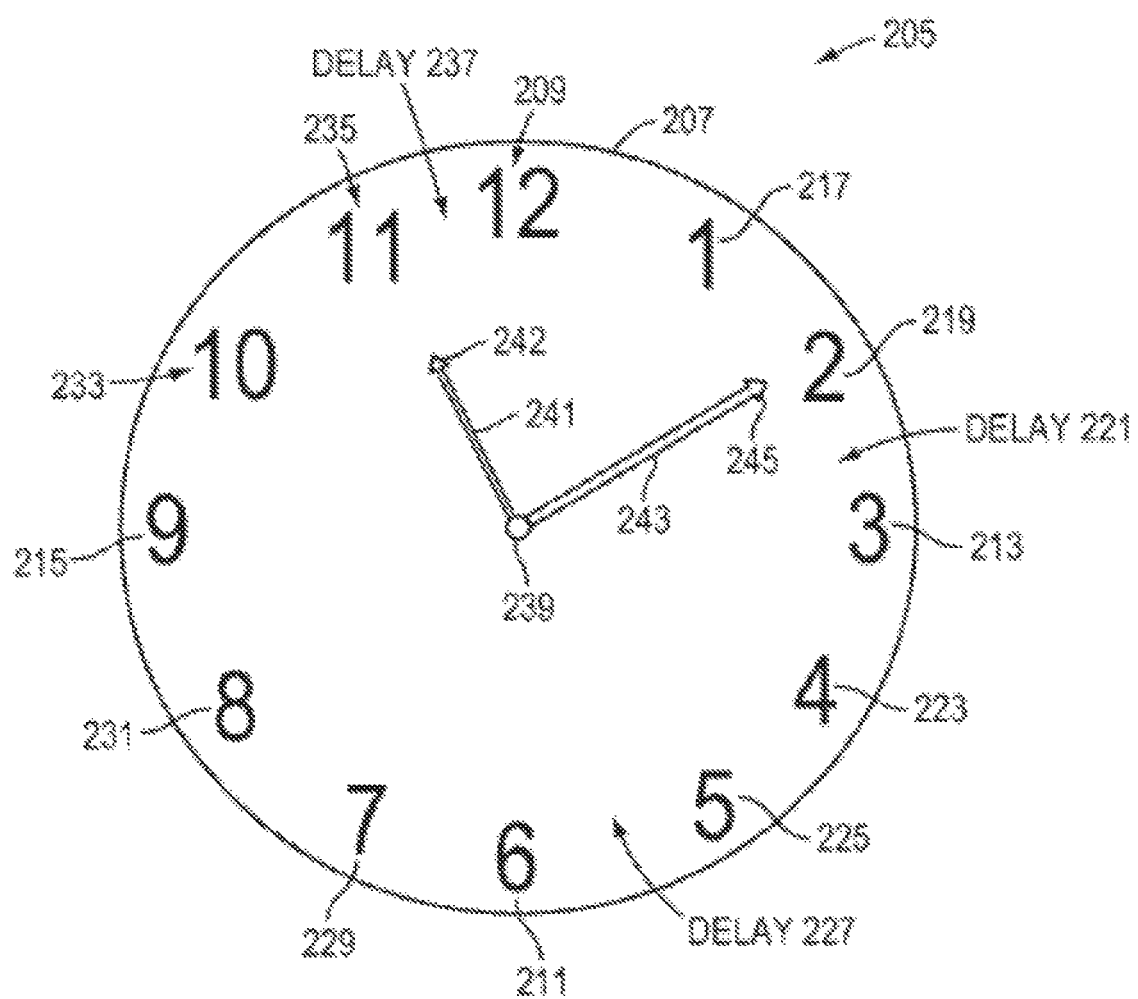
FIG. 2B is an illustration of a Clock Drawing Test that may be received in accordance with an example embodiment of the present invention in which a chronological sequence by which the test was performed may be viewed.

FIG. 2B is a clock diagram illustrating a result (i.e., clock face 205) of a CDT that may be received in accordance with an embodiment of the present invention. A chronological sequence by which the test was completed may be viewed. The following sequence is an example chronological sequence by which the person drew the clock diagram 203. Initially, the person drew a circle 207 to represent a border of the clock face 205. The person then drew the numerals "2" 209, "6" 211, "3" 213, and "9" 215. Next, the person drew the numeral "1" 217 and the numeral "2" 219, which was followed by a delay (or pause) 221. The person then drew the numerals "4" 223 and "5" 225, which was followed by another delay 227. Next, the person drew the numerals "7" 229, "8" 231, "10" 233, and "11" 235, which was followed by a delay 237. The person then drew a mark 239 at the center of the clock face 205. Then, the person drew an hour hand 241 of the clock and then an arrowhead 242. The person then drew a shaft of the minute hand 243 and then the arrowhead 245 of the minute hand 243.

By allowing the medical practitioner to observe the chronological order by which the person created the clock face 205, the medical practitioner is able to observe the executive function of the person by his/her planning and strategy, such as creating quadrants by placing the "12" 209, "6" 211, "3" 213, and "9" 215, in that order. The medical practitioner is able to observe the spatial approach to the task relating to parietal function. Additionally, the delays 221, 227, 237 or lack of a delay noticed when the person reaches the previously drawn "3" 213, "6" 211, "9" 215, and "12" 209 relate to the person's memory, both short-term (instructions for the time) and long-term (image of a clock face in the person's memory) and executive function or their ability to rapidly process information (e.g., decision to refrain from drawing again the previously drawn numbers).

Figure 2C:
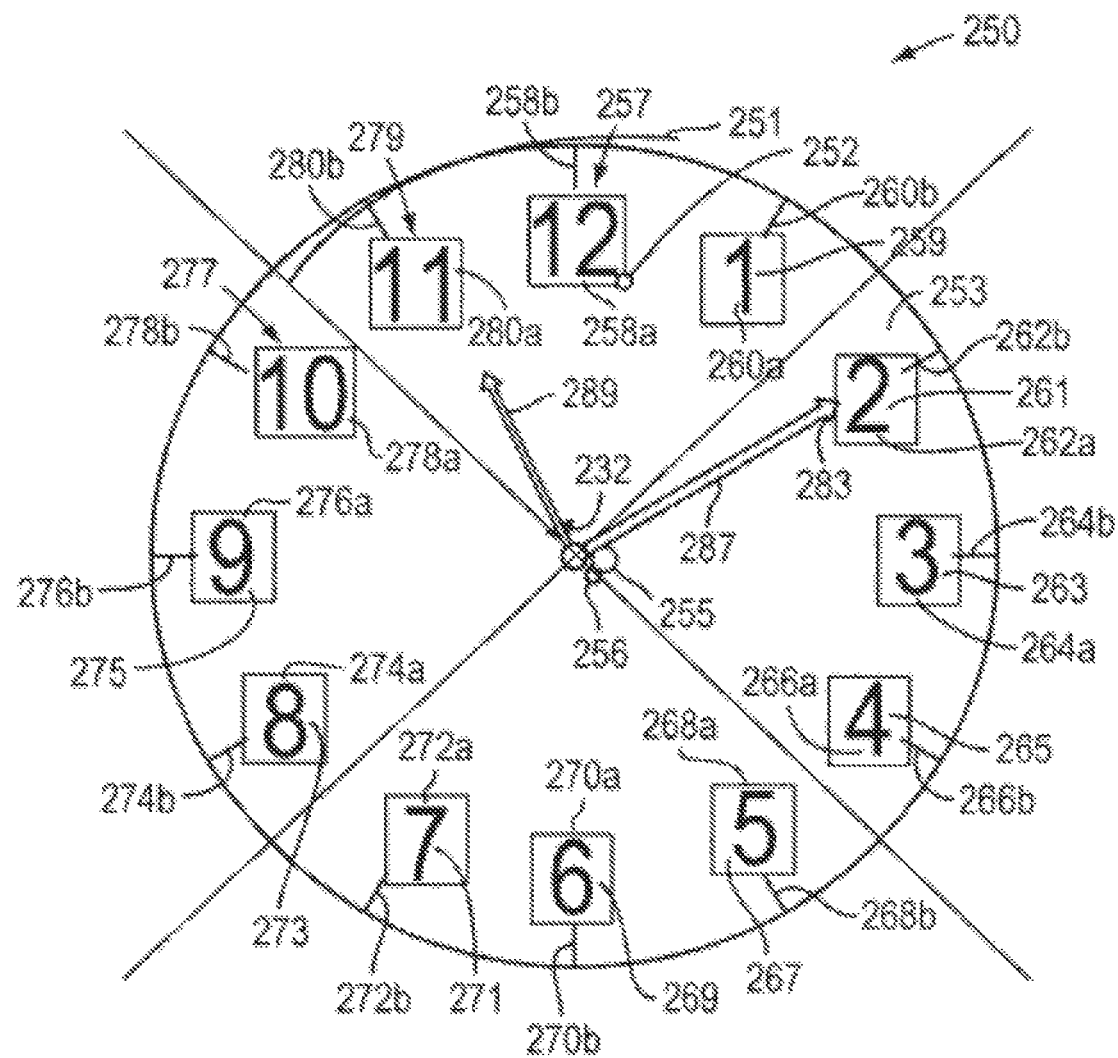
FIG. 2C is an illustration of a Clock Drawing Test that may be received in accordance with an example embodiment in which each element of the Clock Drawing Test may be classified.

FIG. 2C is a clock drawing illustrating a result (i.e., clockface 250) of a CDT that may be received in accordance with an example embodiment, whereby each element of the clock 250 may be classified. In one embodiment, each element of the clock is approximated. For example, the clock face 251 is drawn by the person, and the processing of the embodiment approximates the clock face 251 with an ellipse or circle 252 that best fits the clock face 251. The ellipse or circle 252 has a major axis 253 (major axis center 255) and a minor axis 254 (minor axis center 256). Additionally, each numeral 1-12 representing an hour on the clock face 251 is placed inside of a "bounding box" (or box), which may be a rectangle with horizontal or vertical sides that are just large enough to enclose a respective numeral. Also, a line may be drawn from the circle 252 to the center of each respective box, where the intersection of the lines and the circle 252 indicates the spacing of the numerals around the circle 252. The sizes of the boxes and angles of the lines may be mined for information that may be used to analyze results of the CDT. Further, the distance between the centers of the boxes and the circle 252, and the trends of the centers (e.g., numerals 7-11 from the left side of the circle 252) may also be mined for information of test results.

The following is a list of the numbers with its corresponding box: "12" 257 (box 258a, line 258b), "1" 259 (box 260a, line 260b), "2" 261 (box 262a, line 262b), "3" 263 (box 264a, line 264b), "4" 265 (box 266a, line 266b), "5" 267 (box 268a, line 268b), "6" 269 (box 270a, line 270b), "7" 271 (box 272a, line 272b), "8" 273 (box 274a, line 274b), "9" 275 (box 276a, line 276b), "10" 277 (box 278a, line 278b), and "11" 279 (box 280a, line 280b). The drawn hour hand 281 is approximated in the present embodiment with a computer generated arrow 282 that best fits the drawn hour hand 281. The drawn minute hand 283 is indicated in the present embodiment with a computer generated arrow 284 that best fits the drawn minute hand 283.

Figure 2D:
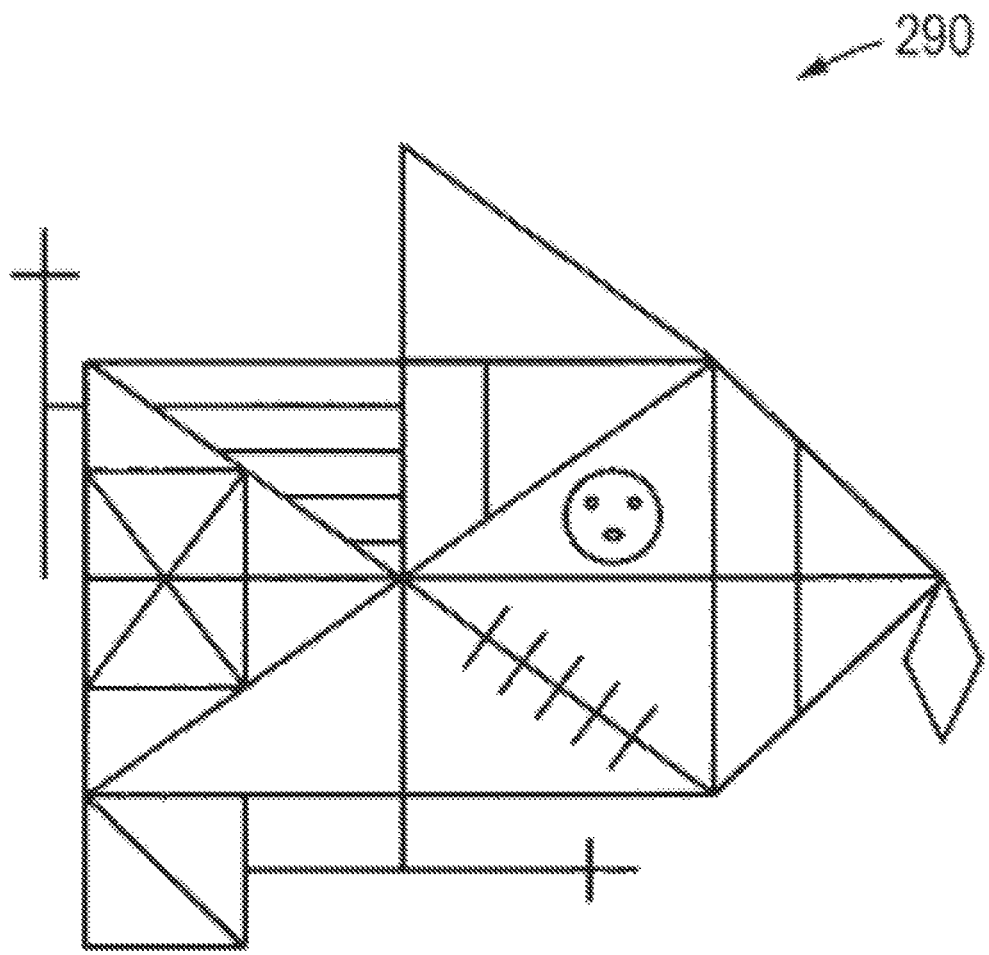
FIG. 2D is an illustration of a Rey-Osterreith Complex Figure Test, which is a neuropsychological test, that may be administered in accordance with another embodiment of the present invention.

FIG. 2D is a diagram illustrating a result 290 of a Rey-Osterreith Complex Figure Test, a neuropsychological test, that may be administered in accordance with another embodiment of the present invention.

Figure 3A:
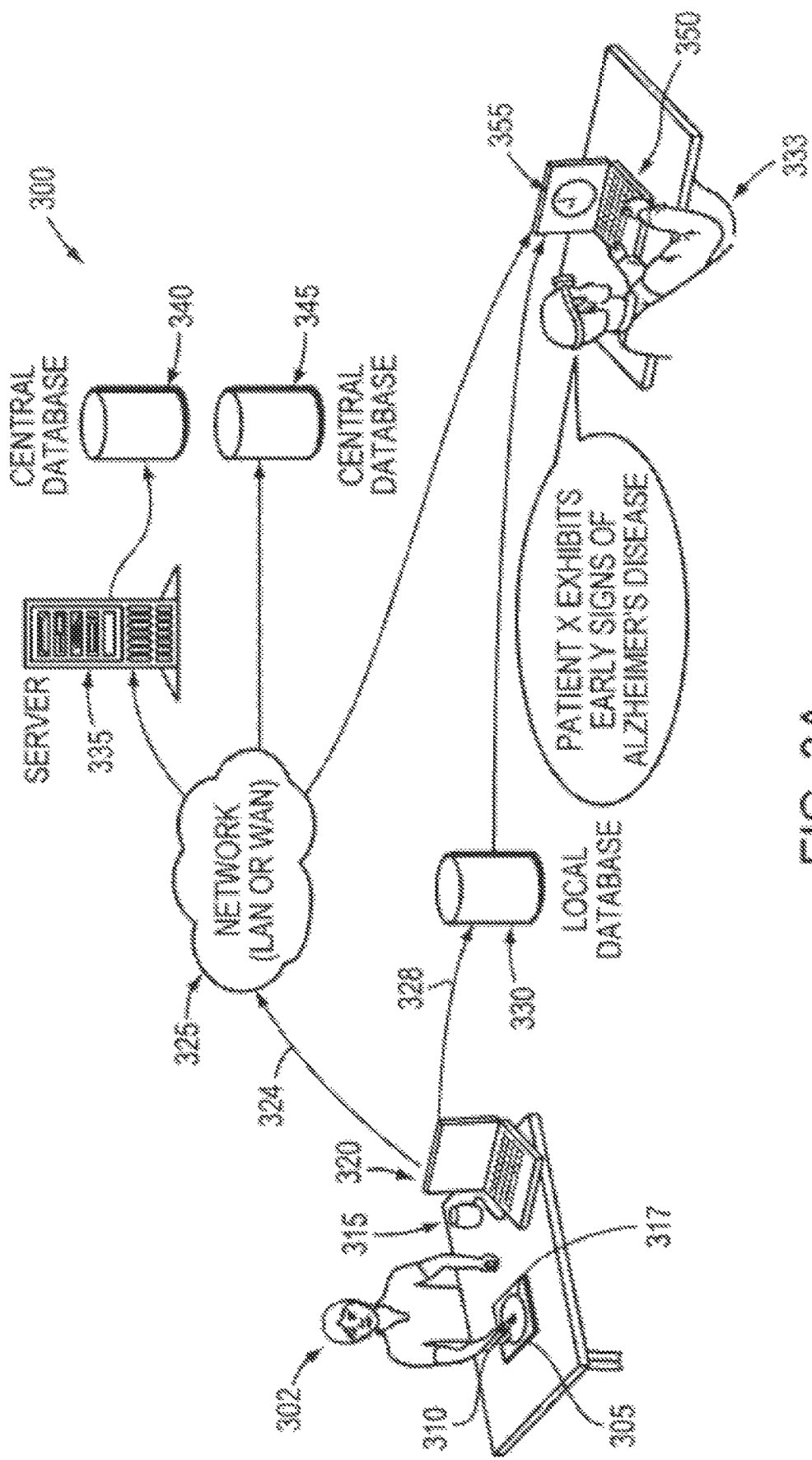
FIG. 3A illustrates an administration of the Clock Drawing Test where representations of individual representational motions made by a person in generating an analog clock face may be sent either to a network or a local database, and thereafter observed by a medical practitioner for analysis and diagnosis purposes in accordance with the present disclosure.
Figure 3B:
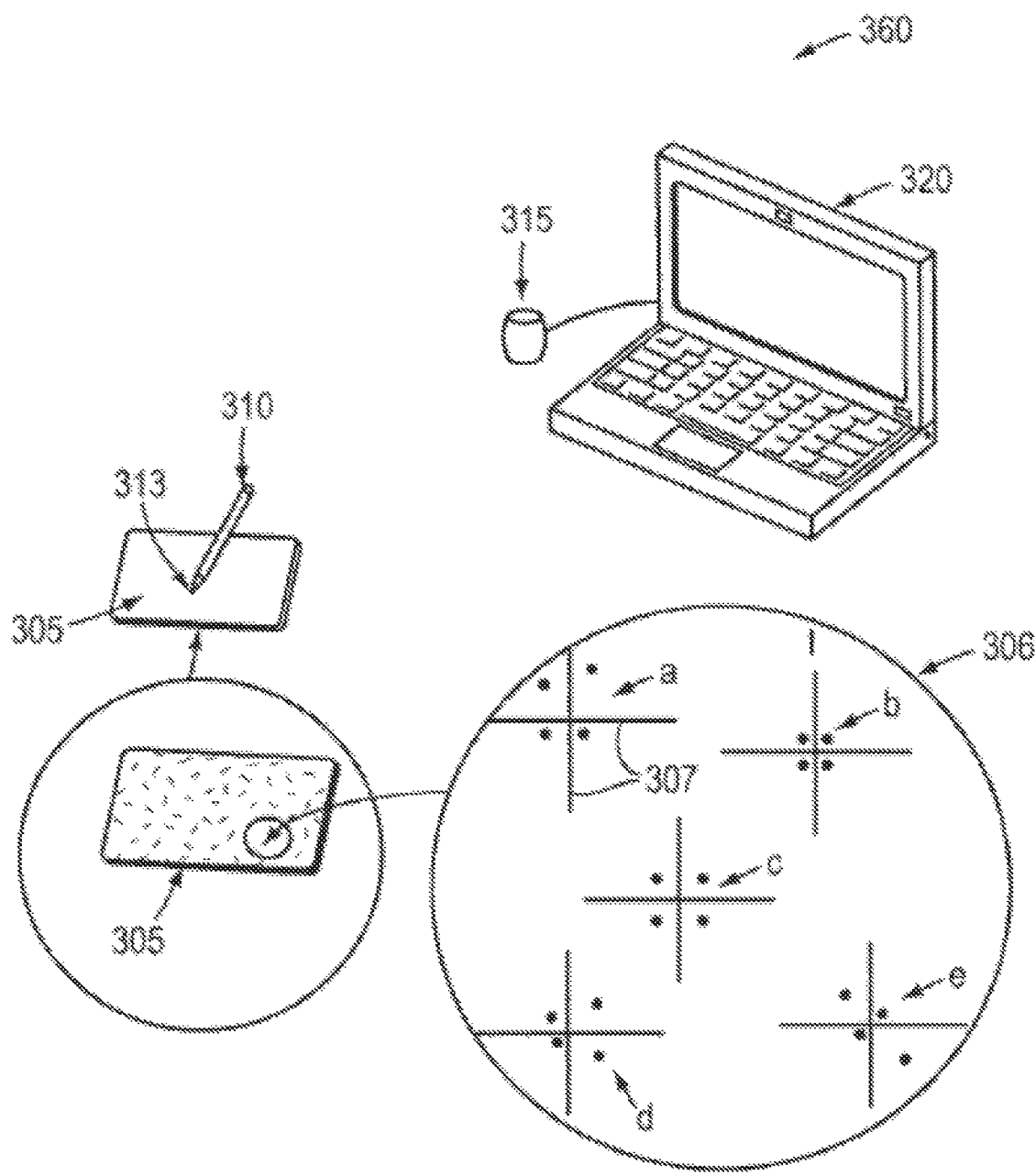
FIG. 3B is a close-up view of an example neuropsychological testing apparatus in accordance with an embodiment of the present disclosure.
Figure 3C:
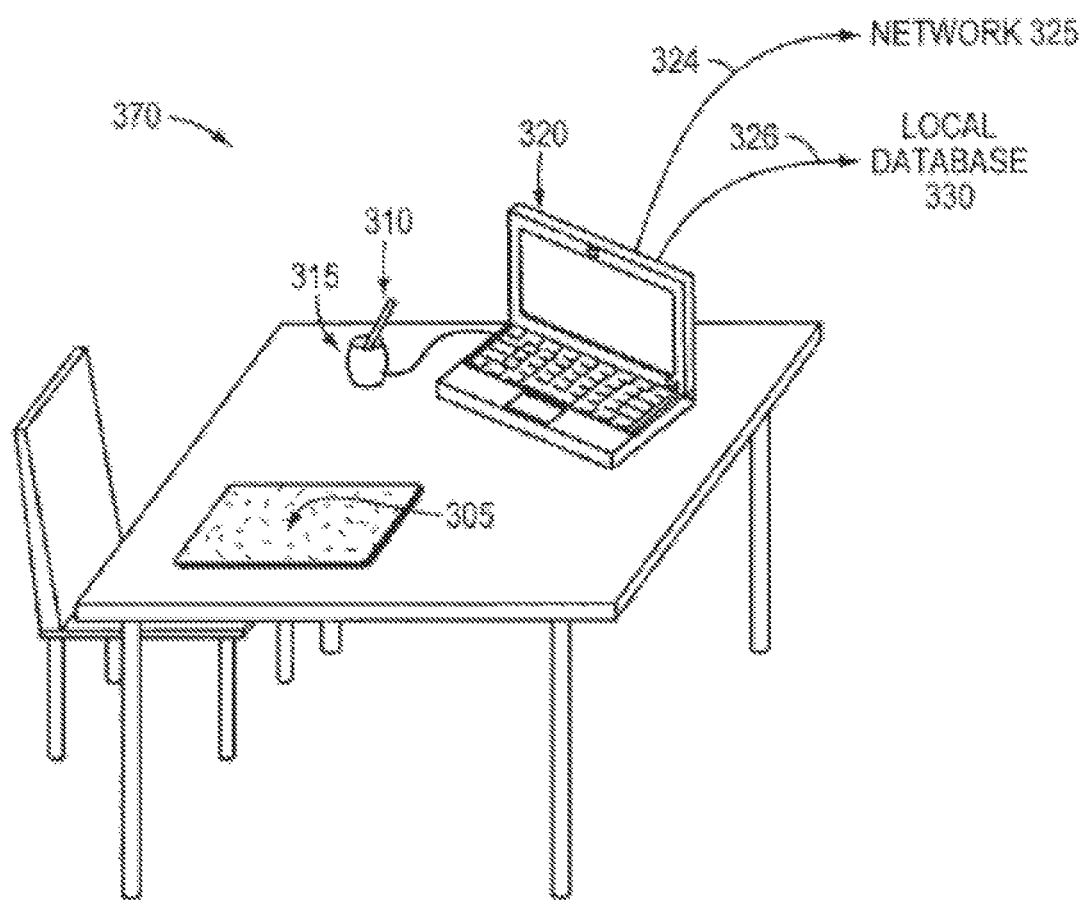
FIG. 3C is an example neuropsychological testing apparatus in accordance with another embodiment.

FIGS. 3A through 3C are diagrams that illustrate an example administration of a CDT in accordance with an embodiment of the present invention. FIG. 3A is a network diagram of a network 300 illustrating network-based administration of the CDT in accordance with the present disclosure. The person 302 (i.e., test subject or examinee) is administered a CDT where the person 302 uses paper 305 and a capture unit 310 (herein represented as a digitizer) to draw a clock according to the CDT, where drawing the clock 317 may result in a physical or electronic drawing of the clock 317. In FIG. 3A, the capture unit 310 includes a docking station 315, which is connected to a computer 320. In this example embodiment, the computer 320 either transmits collected representations (not shown) of the clock 317 to a local database 330 for storage via a local connection 328 or to a network (local or wide area) 325 via a remote connection 324. The network 325 can be connected to a myriad of storage devices, represented as a server 335 with central database 340, central database 345, or directly to a doctor's computer 350. The doctor's computer 355 may also receive the collected representations from a local database 330. The doctor 333 may then review the collected representations 355 under an array of default or doctor selected conditions, which include: a real-time movie, slow-motion images, chronological order, approximations and associated numerical values, and the like. By allowing the doctor 333 to select condition(s) under which to review the representations of individual representational motions made by the person 302 while drawing the clock 317 in this example, the doctor is better able to analyze the representations and what the motions indicate regarding the person's neurocognitive condition(s). The collected representations 355 may be preserved to enable comparison to performance on a subsequent testing and may enable to the doctor to reexamine the prior drawing, which may allow for additional assessment of change in the person's 302 performance over time. Additionally, the collected representations 355 may allow for a second opinion to be received based upon the same drawing.

It should be understood that the embodiment of FIG. 3A may be used to test any of the previously mentioned conditions of the CDT. Additionally, the present embodiment may be used in assessment across the lifespan of a person, including children through geriatric, and in a variety of medical contexts, including at least one of the following: neuropsychological, neurological, neurogenetic, geriatric, pediatric, ]general health, rehabilitation centers, clinical evaluation of therapeutic interventions, or diagnostic purposes. The apparatus and corresponding method may be used in several settings, which include a medical facility or school, with or without the supervision of a medical practitioner. The apparatus and method can also be used on a control group and a test group to develop domestic or international standard(s), and which is simplified logistically through use of network data transfer and, optionally, collaborative network support utilities to allow doctors to collaborate on their research results with common or local data.

FIG. 38 is a close-up view of an example neuropsychological testing apparatus 360 in accordance with the present embodiment. The example neuropsychological testing apparatus 360 is useful for neuropsychological testing that is paper and writing utensil based because use of an apparatus as depicted in FIG. 3B does not materially alter the testing, while introducing advancements in technology. The digitizer 310 can be operated as a normal writing utensil (e.g., pencil, pen, marker, colored pencil, crayon, or the like) because the digitizer 310 is similar to a pen in terms of size and weight. A cap (not shown) of the digitizer 310 may function as an on/off switch. In this example, the digitizer 310 has an optical sensor 313 on its tip, which allows for capturing and recording the motions made by the person using the digitizer 310. Digital representations of the motions may be transmitted to the computer 320 by placing the digitizer 310 in the docking station 315, which is connected to the computer 320, or via a direct wired or wireless interface (not shown). In this embodiment, the computer 320 contains software that allows for the transmission, conversion, management, storage, reporting, and display of the information based on the data received from the digitizer 310.

The paper 305 has printed thereon a collection of patterns of small dots 306a-e that communicates a particular location on the paper 305 to the digitizer 310 and is relatively unnoticeable to the naked eye, meaning that the person 302 may only notice a slight color or tint. The patterns of small dots 306a-e are unique (i.e., self-identifying) relative to a regularly spaced grid 307 to allow software either in the digitizer 310 or computer 320 to translate the unique patterns 306a-e to unique locations on the paper 305. It should be understood that a vast number of patterns of dots relative to gridlines may be used to support very precise determination of the digitizer 310 on the paper 305 or to within a location tolerance suitable for capturing data accurately. The digitizer 310 shown is used only for example purposes. The digitizer 310 of FIG. 3B may be used to digitize or record handwritten motions, but it should be understood that other forms of digitizers may be employed to capture representations of individual representational motions made by any other appendage or activity of the person's body.

FIG. 3C is an example neuropsychological testing apparatus in accordance with the environment 370 of FIG. 3A. In FIG. 3C, the digitizer 310 has been placed in the docking station 315, which is connected to the computer 320. Once the digitized representations of individual representational motions made by the person 302 in drawing a clock on the paper 305, for example, collected by the digitizer 310 is transmitted to the computer 320 via the docking station 315, the digitized representations may be stored on the computer 320. The digitized representations may also be transmitted 324, 326 to either a network 325 or a local database 330.

Figure 3D:
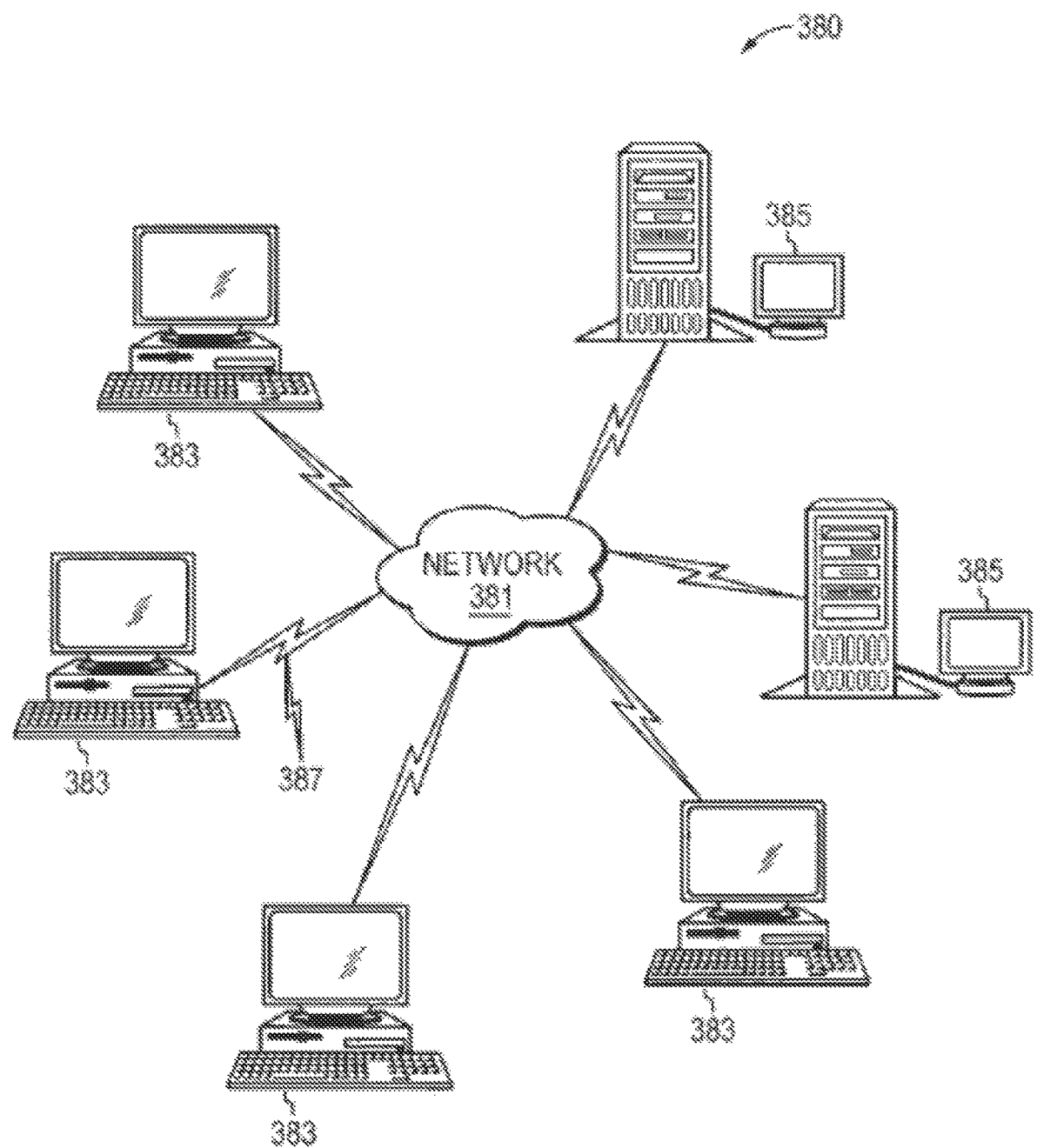
FIG. 3D is a schematic view of a computer environment in which the principles of the present invention may be implemented.

FIG. 3D illustrates a computer network or similar digital processing environment 380 in which embodiment(s) of the present invention may be implemented.

Computer(s)/devices 383 and server computer(s) 385 provide processing, storage, and input/output devices executing application programs and the like. The computer (s)/devices 383 can also be linked through a communications network 381 to other computing devices (not shown), such as other devices/processes 383 and server computer(s) 385. The communications network 381 can be part of a remote access network, a global computer network (e.g., the Internet), a worldwide collection of computers, local area or wide area networks (LAN or WAN, respectively), and gateways that currently use respective protocols (TCP/IP, Wireless Local Area Network (WLAN), Bluetooth®, etc.) to communicate with one another. Other electronic device/ computer network architectures may also be suitable for use with embodiments of the present invention.

Figure 3E:
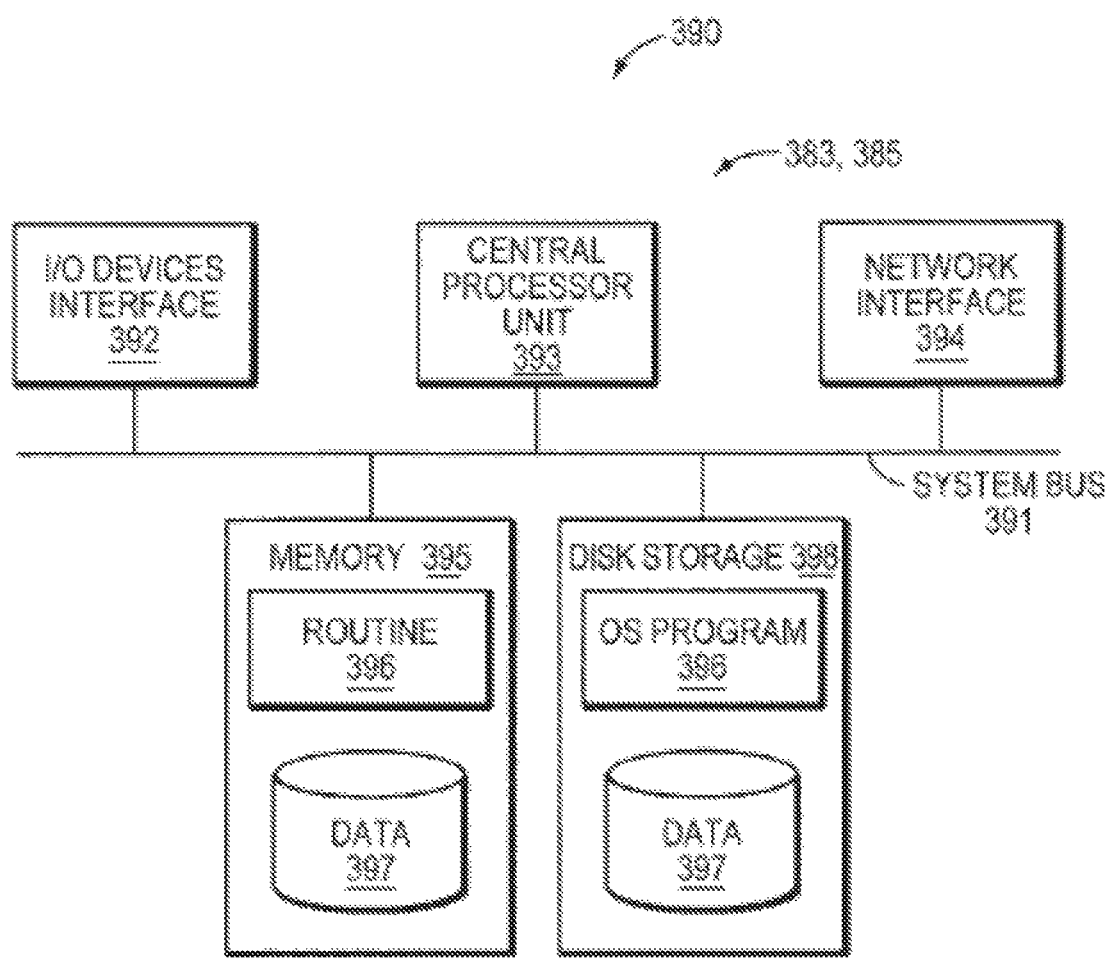
FIG. 3E is a block diagram of an internal structure of a computer in the FIG. 3D computer environment.

FIG. 3E is a diagram of an example internal structure 390 of a computer (e.g., processor/device 383 or server computers 385) in the computer system 380 of FIG. 3D. Each computer 383, 385 contains a system bus 391, where a bus is a set of hardware lines used for data transfer among the components of a computer or processing system. The bus 391 is essentially a shared conduit that connects different elements of a computer system (e.g., processor, disk storage, memory, input/output ports, network ports, etc.) that enables the transfer of information between the elements. Attached to system bus 391 is an I/O device interface 392 for connecting various input and output devices (e.g., keyboard, mouse, displays, printers, speakers, etc.) to the computer 383, 385. A network interface 394 allows the computer to connect to various other devices attached to a network (e.g., the network 381 of FIG. 3D). Memory 395 provides volatile or non-volatile storage for computer software instructions 396 and data 397 used to implement an embodiment of the present invention (e.g., central database records per CDT, supporting tables and classification estimation calculations). A disk storage 398 provides non-volatile storage for computer software instructions 396 and data 397 used to implement an embodiment of the present invention. A central processor unit 393 is also attached to system bus 391 and provides for the execution of computer instructions.

In one embodiment, the processor routines 396 and data 397 are stored on a computer program product (generally referenced as 396), including a computer readable medium (e.g., a removable storage medium, such as one or more DVD-ROM's, CD-ROM's, diskettes, tapes, etc.) that provides at least a portion of the software instructions for the network or single computer embodiment. The computer program product 396 can be installed by any suitable software installation procedure, as is well known in the art. In another embodiment, at least a portion of the software instructions may also be downloaded over a communications cable or wireless connection. In other embodiments, the invention programs are a computer program propagated signal product 387 embodied on a propagated signal on a propagation medium (e.g., a radio wave, infrared wave, laser wave, sound wave, or electrical wave propagated over a global network, such as the Internet, or other network(s)). Such carrier medium or signals provide transmission support for at least a portion of the software instructions for the present invention routines/program 396.

In alternative embodiments, the propagated signal is an analog carrier wave or digital signal carried on the propagated medium. For example, the propagated signal may be a digitized signal propagated over a global computer network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 396 is a propagation medium that the computer system 383 may receive and read, such as by receiving the propagation medium and identifying a propagated signal embodied in the propagation medium, as described above for computer program propagated signal product.

Further, the present invention may be implemented in a variety of computer architectures. The computer network of FIGS. 3D and 3E are for purposes of illustration and not limitation of any embodiments of the present invention.

Figure 4:
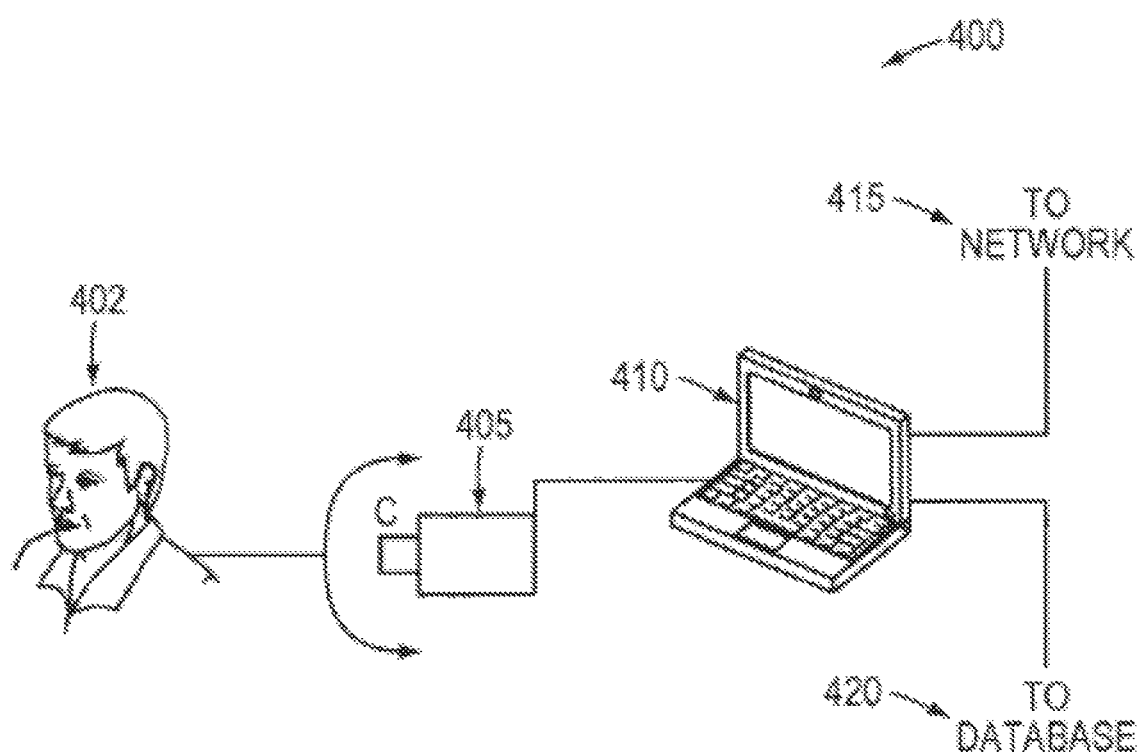
FIG. 4 is an example neuropsychological testing apparatus that may be implemented in accordance with another embodiment of the present invention.

FIG. 4 is a schematic diagram of an example neuropsychological testing apparatus 400 that may be implemented in accordance with an embodiment of the present invention. In FIG. 4, the person 402 may be observed by using a camera 405 (or a similar motion recording device) while performing a neuropsychological test, such as a CDT). The camera 405 is configured to record individual representational motions made by the person 402 during the neuropsychological test. The camera 405 may be coupled to a computer 410. The motions recorded by the camera 405 may be stored on the computer 410. The motions recorded may also be sent from the computer to a network (local area or wide area) 415 or to a database 420.

Figure 5:
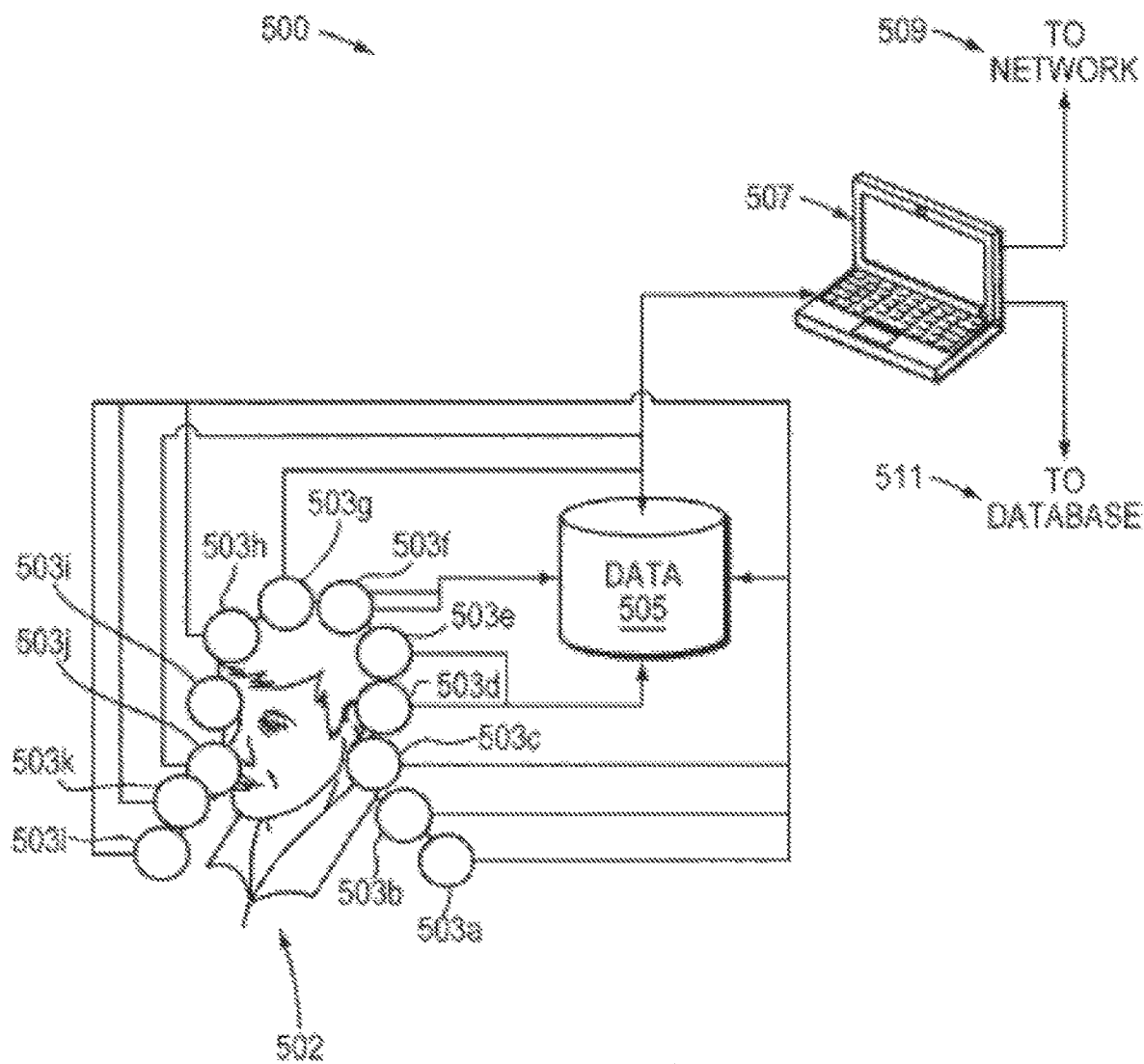
FIG. 5 is an example illustration of a neuropsychological testing apparatus in accordance with another example embodiment.

FIG. 5 is an example test environment 500 illustrating a neuropsychological testing apparatus that may be implemented in accordance with an embodiment of the present invention. Motion sensors 503a-1 may be attached to the person 502 and the representations of the motions made by the person 502 while performing a neuropsychological test may be sent to a data storage unit 505 that is coupled to (i.e., in electrical communication with) the motion sensors 503a-1 either directly or via an interface (not shown), such as a computer. The connection between the motion sensors 503a-5031 may be connected optically, wirelessly, by wires, or the like. The data storage unit 505 may store the representations of motions made by the person 502 as recorded by the motion sensors 503a-1. The data storage unit 505 may be connected to a computer 507, which may store the representations of motions. The computer 507 may also send the recorded representations of motion or other related information to a network 509 or to a database 511.

FIGS. 4 and 5 are provided to illustrate and detail additional embodiments that may be used in accordance with the present disclosure. Such examples are not meant to be exclusionary, and are only included for example purposes.

Figure 6:
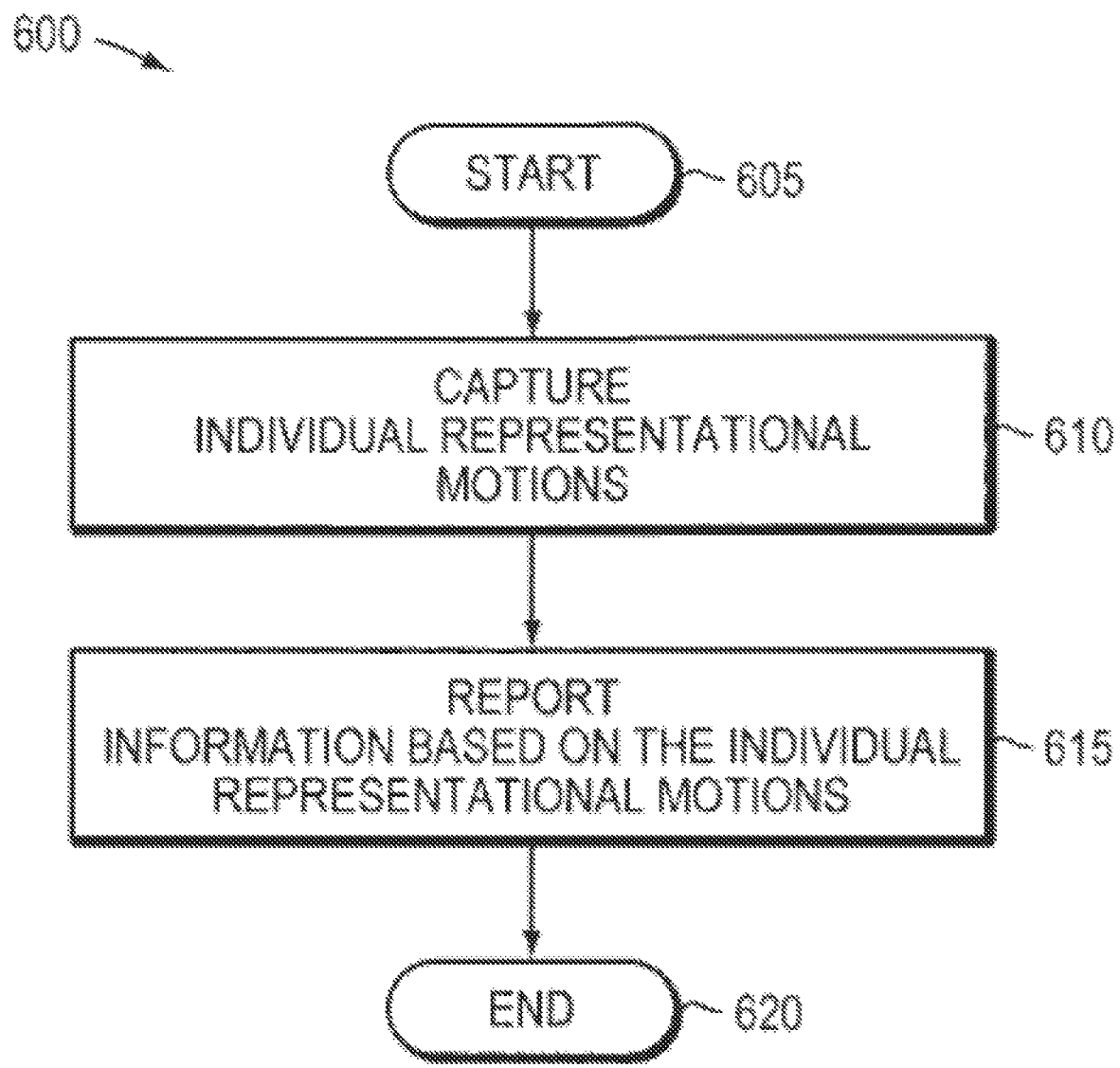
FIG. 6 is a process flow diagram of a method for measuring representational motions of a person.

FIG. 6 is a process flow diagram of an example method 600 for measuring representational motions as made by a person. The person begins to perform (605) the neuropsychological test using an embodiment of the apparatus and corresponding method. The individual representational motions made by the person may be captured (610). Next, information based on the individual representational motions may then be reported (615). The method ends (620) and a user (or examiner), such as a doctor, can begin analysis or other task based on the information obtained during the neuropsychological testing.

Figure 7A:
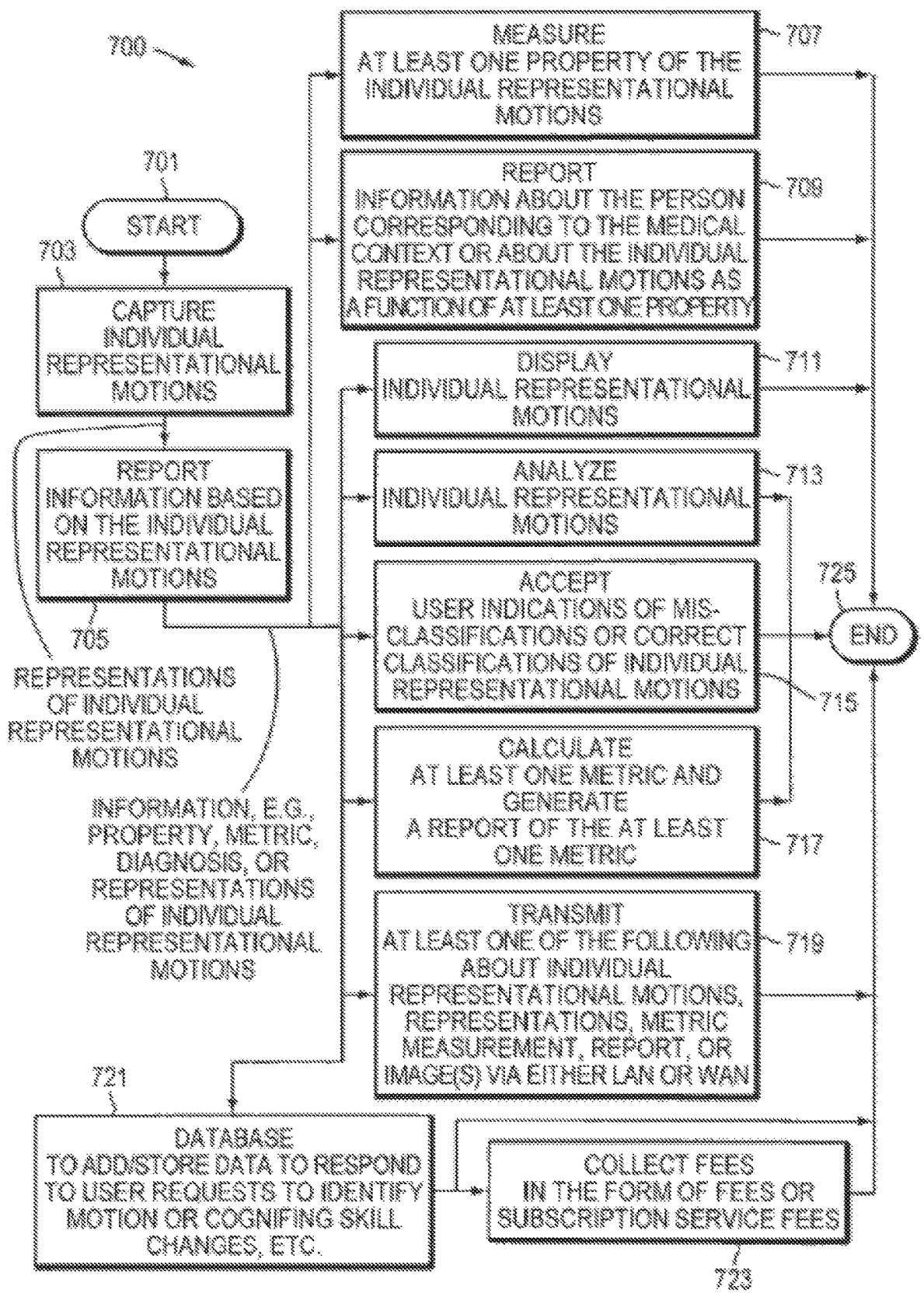
FIG. 7A is a process flow diagram of a method for measuring representational motions made by a person in accordance with an example embodiment of the present disclosure.

FIG. 7A is a process flow diagram of an example method 700 for measuring representational motions made by a person in accordance with the present disclosure. After the person begins (701) to perform the neuropsychological test, the individual representational motions made by the person are captured (703) with spatial precision, which may include logging timestamps that indicate the times at which the person made the individual representational motions.

"Individual representational motions" may be defined by at least one of the following: change in position of an appendage of the person relative to a reference point, acceleration, rate, time of making an individual representational motion relative to other individual representational motions, starting and ending positions relative to expected positions, null and absence of motion, or via point positions relative to expected via point positions between a starting position and an ending position. "Spatial precision," as used herein, is defined by capturing the individual representational motions within a tolerance recognized as acceptable to measure accurately an individual representational motion by the person in the medical context. Example tolerances with respect to handwritten motions may be less than 0.1 mm, 1 mm, 10 mm, 100 mm, or other value suitable for the particular handwritten motions. Similarly, "spatial precision" may have larger or smaller values depending on the appendage or extremity making the motion (e.g., arm, leg, finger, etc.). Information about the representations of the individual representational motions or about the person may be reported (705). "Information" as used in this context includes a property, metric, diagnosis (e.g., a list of potential diagnoses, list of observations, or list of observations and corresponding potential diagnoses), or representations of individual representational motions (i.e., the captured data in an unprocessed form). After reporting the information, at least one property of the individual representational motions may be measured (707, see FIG. 7B). Information about the person corresponding to the medical context or about the individual representational motions as a function of at least one property may be reported (709, see FIG. 7C). The reported information may also be displayed (711, see FIG. 7D), which could either occur as a single image; a chronological sequence; or a chronological sequence in real-time, slow motion mode, or fast forward mode.

The information about the individual representational motions may also be analyzed (713, see FIG. 7E) in an automatic or semi-automatic mode, which may be done based on the spatial, temporal, or geometric properties of the individual representational motions as well as the chronological sequence in which the person made the individual representational motions. Additionally, the user analyzing the information may indicate misclassifications or correct classifications of the individual representational motions (715). The information may be used to calculate a metric or to generate a report of the information or the metric (717). The information may also be transmitted (719) either via a network (local or wide area) or stored in a database (721).

The database 721 may be used for any of the following: to respond to user queries, to identify motor or cognitive skill changes of the person, to monitor the status of implantable interventions in the person, to monitor the pharmaceutical dosage given to or treatment administered on the person, to assist with differential diagnosis, or to identify additional tests that may be necessary. The database (721) may also be used by third parties for a fee, which may be collected in the form of single usage fees, subscription service fees, and the like. At any time, the user of the method may terminate (725) the measurement process of the motions made by a person. It should be understood that after the motions made by the person are captured and recorded, any of the aforementioned example aspects (e.g., 701, 703, 705, and so forth) of the method of FIG. 7A may or may not occur in any particular order. The preceding information was given to provide general guidance but not to serve as an exclusive explanation of all embodiments of the present invention.

Figure 7B:
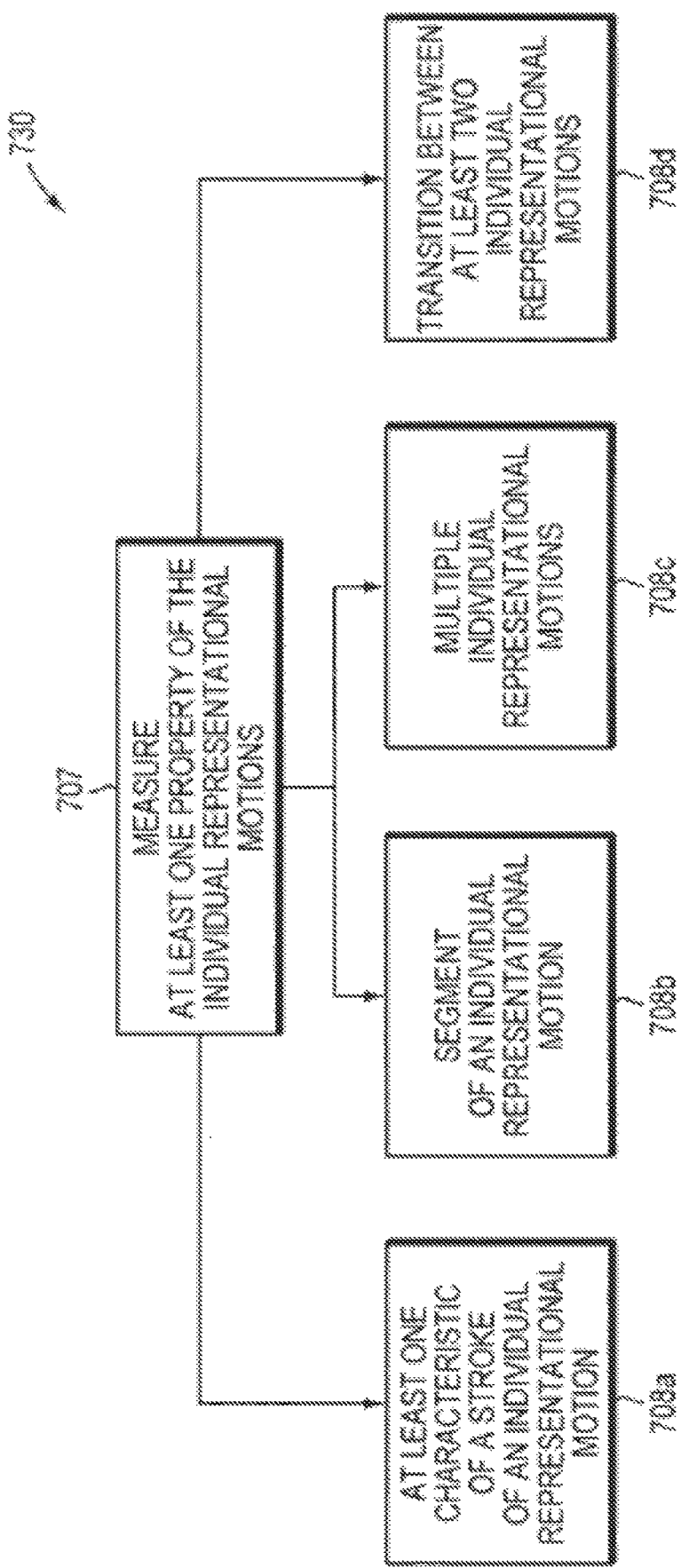
FIG. 7B is a block diagram of a method for measuring at least one property of the individual representational motions of the present disclosure.

FIG. 7B is a block diagram of an example method 730 for measuring at least one property of the individual representational motions of the present disclosure. After reporting the information, at least one property of the individual representational motions may be measured (707). The following is a list of examples of at least one property of the individual representational motions that may be measured: at least one characteristic of a stroke of an individual representational motion (708*a*), segment of an individual representational motion (708*b*), multiple individual representational motions (708*c*), or transition between at least two individual representational motions (708*d*).

Figure 7C:
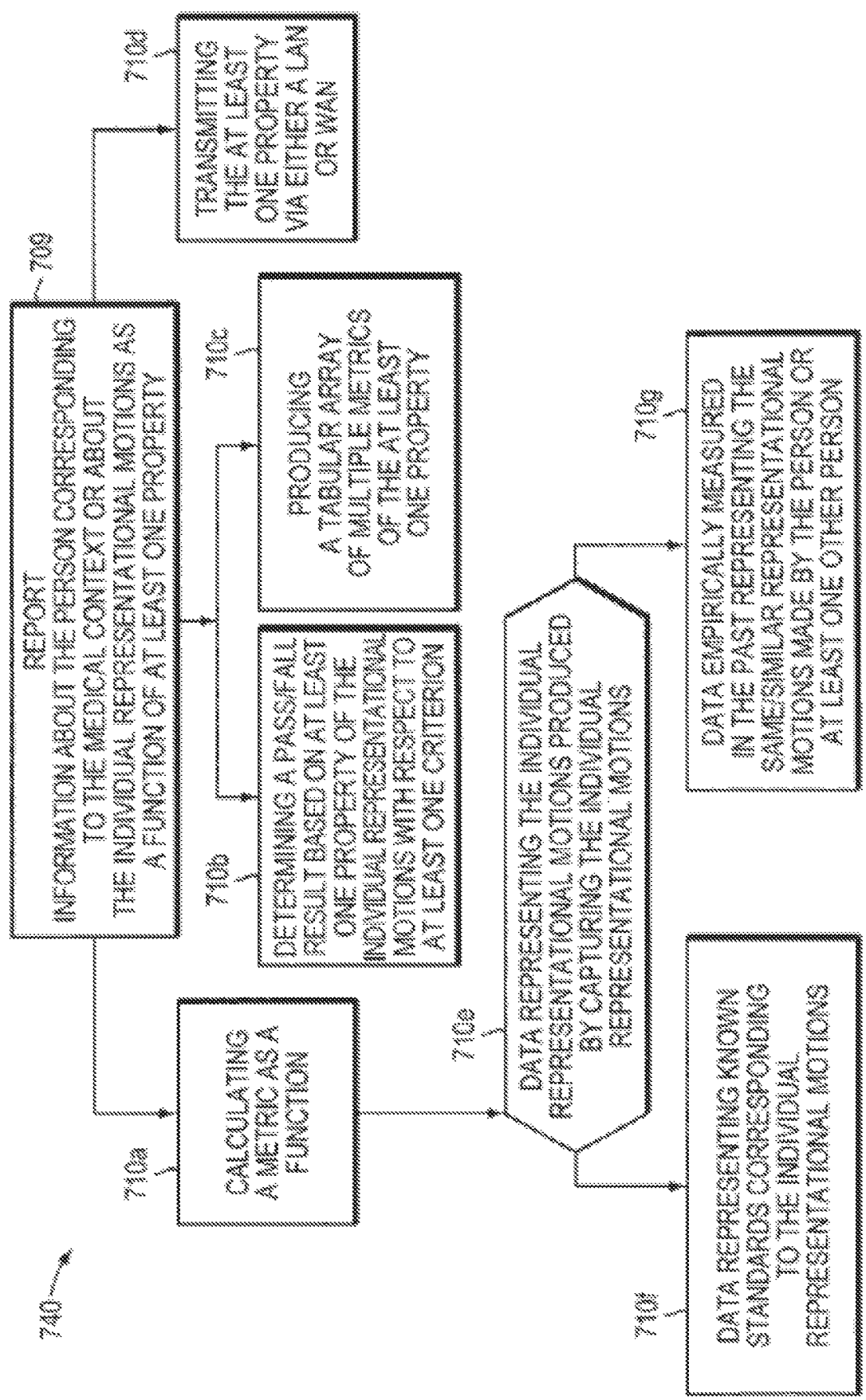
FIG. 7C is a block diagram of a method for reporting information about the person or the individual representational motions as a function of at least one property in accordance with an example embodiment.

FIG. 7C is a block diagram of an example method 740 for reporting information about the person or the individual representational motions as a function of at least one property in accordance with an example embodiment. Information about the person corresponding to the medical context or about the individual representational motions as a function of at least one property may be reported (709) in the following manners: calculating a metric as a function (710*a*), determining a pass or fail result based on at least one property of the individual representational motions with respect to at least one criterion (710*b*), producing a tabular array of multiple metrics of the at least one property (710*c*), or transmitting the at least one property via either LAN or WAN (710*d*). Calculating a metric as a function (710*a*) may be done based upon data representing the individual representational motions produced by capturing the individual representational motions (710*e*) as either data representing known standards corresponding to the individual representational motions (710*f*) or data empirically measured in the past representing the same/similar representational motions made by the person or at least one other person (710*g*).

Figure 7D:
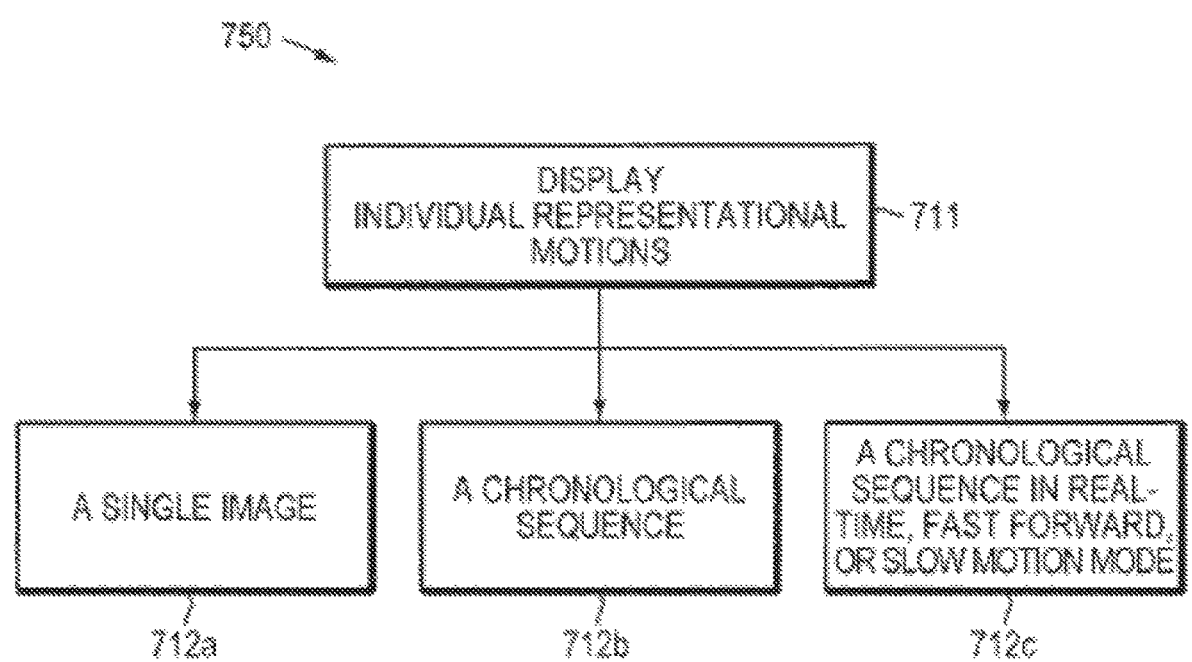
FIG. 7D is a block diagram of a method for displaying individual representational motions in accordance with an example embodiment.

FIG. 7D is a block diagram of an example method 750 for displaying individual representational motions in accordance with an example embodiment. The reported information may also be displayed (711), which could either occur as a single image (712*a*); a chronological sequence (712*b*); or a chronological sequence in real-time, slow motion mode, or fast forward mode (712*c*).

Figure 7E:
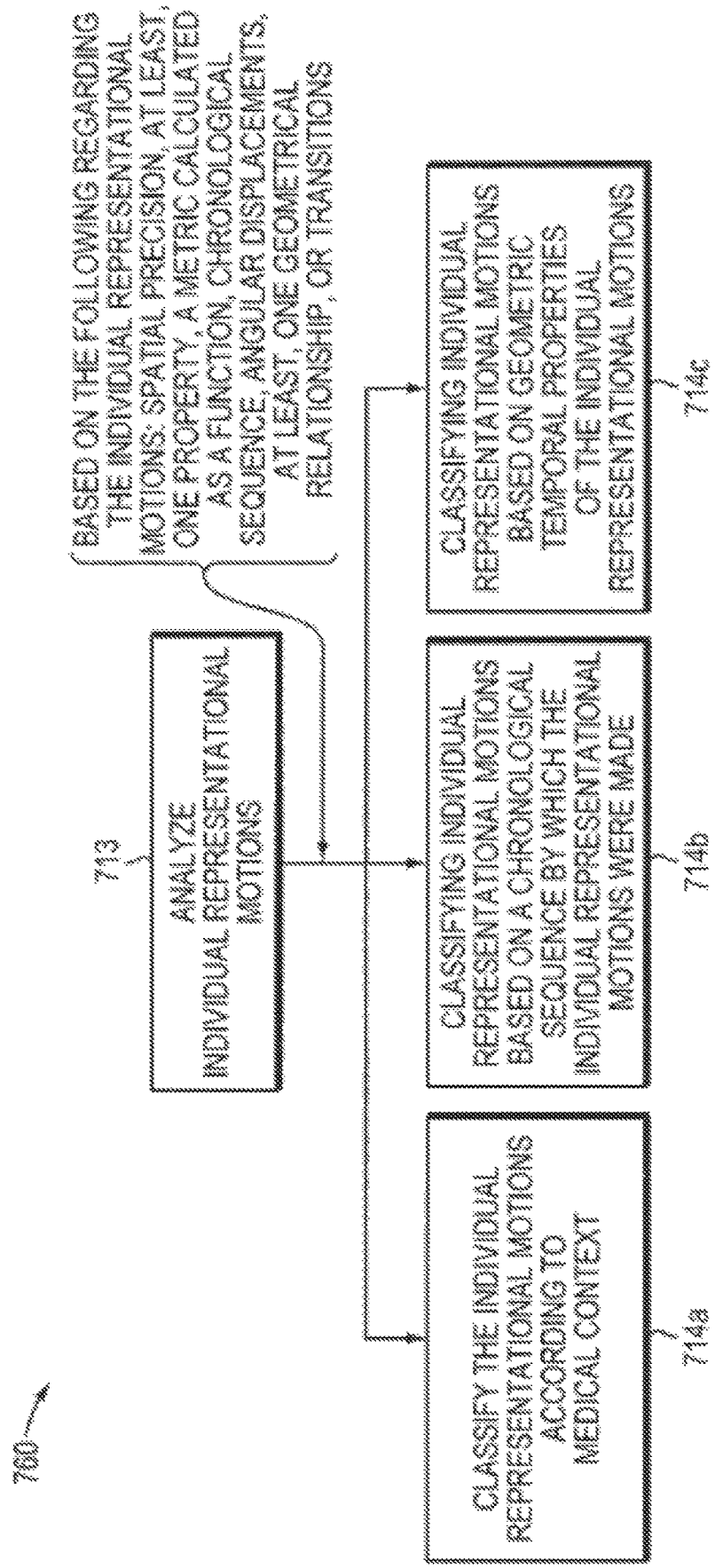
FIG. 7E is a block diagram of a method for analyzing individual representational motions in accordance with an example embodiment.

FIG. 7E is a block diagram of an example method 760 for analyzing individual representational motions in accordance with an example embodiment. The information about the individual representational motions may also be analyzed (713) based on the following regarding the individual representational motions: spatial precision, at least one property, a metric calculated as a function, chronological sequence, angular displacements, at least one geometrical relationship, or transitions. The individual representational motions may be analyzed in the following manners: classify the individual representational motions according to medical context (714*a*), classifying individual representational motions based on a chronological sequence by which the individual representational motions were made (714*b*), or classifying individual representational motions based on geometric or temporal properties of the individual representational motions (714c).

Figure 8A:
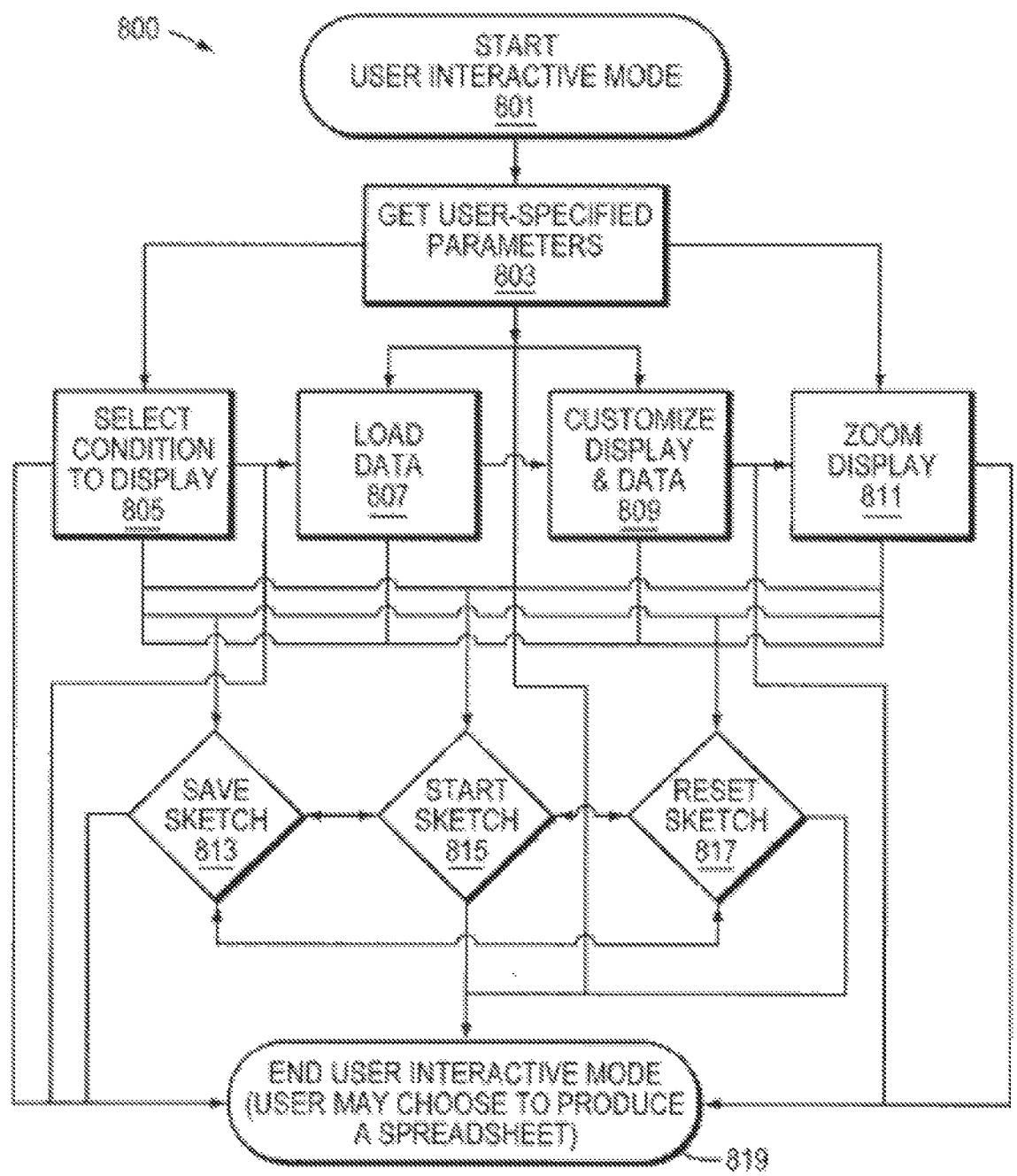
FIG. 8A is a process flow diagram of a user interactive mode of the present disclosure.

FIG. 8A is a process flow diagram 800 of a user interactive mode of the present disclosure. After the user interactive mode is initiated (801), the user is allowed to input certain parameters (803). The following is a list of example parameters available for user specification: select the condition to display (805), load data (807), customize display and data (809), zoom display (811), save a sketch (813), start a sketch (815), or reset a sketch (817). At any time, the user may terminate or may choose (819) to produce a tabular array of interaction or metrics, such as a spreadsheet. The user may choose to perform any of the aforementioned example aspects in any order, so the order shown in FIG. 8A is for illustrative purposes only.

Figure 8B:
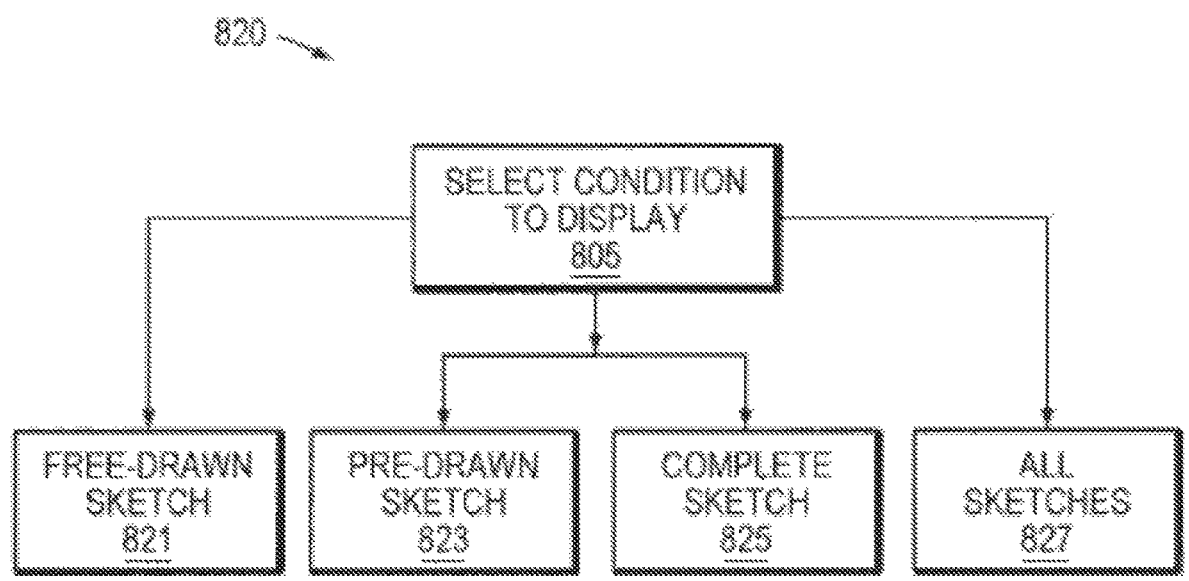
FIG. 8B is a process flow diagram of a user interactive option to select a condition to display captured individual representational motions in accordance with an example embodiment.

FIG. 8B is a process flow diagram 820 of a user interactive option to select a condition to display in accordance with an example embodiment of the present invention. The user may first select a condition to display (805). Example conditions include: free-drawn sketch (821), pre-drawn sketch (823), complete sketch (825), or all sketches (827). As understood in the art, the free-drawn sketch (821) or a completion sketch (825) may be represented as a command sketch; a pre-drawn sketch (823) may be represented as a copy sketch.

Figure 8C:
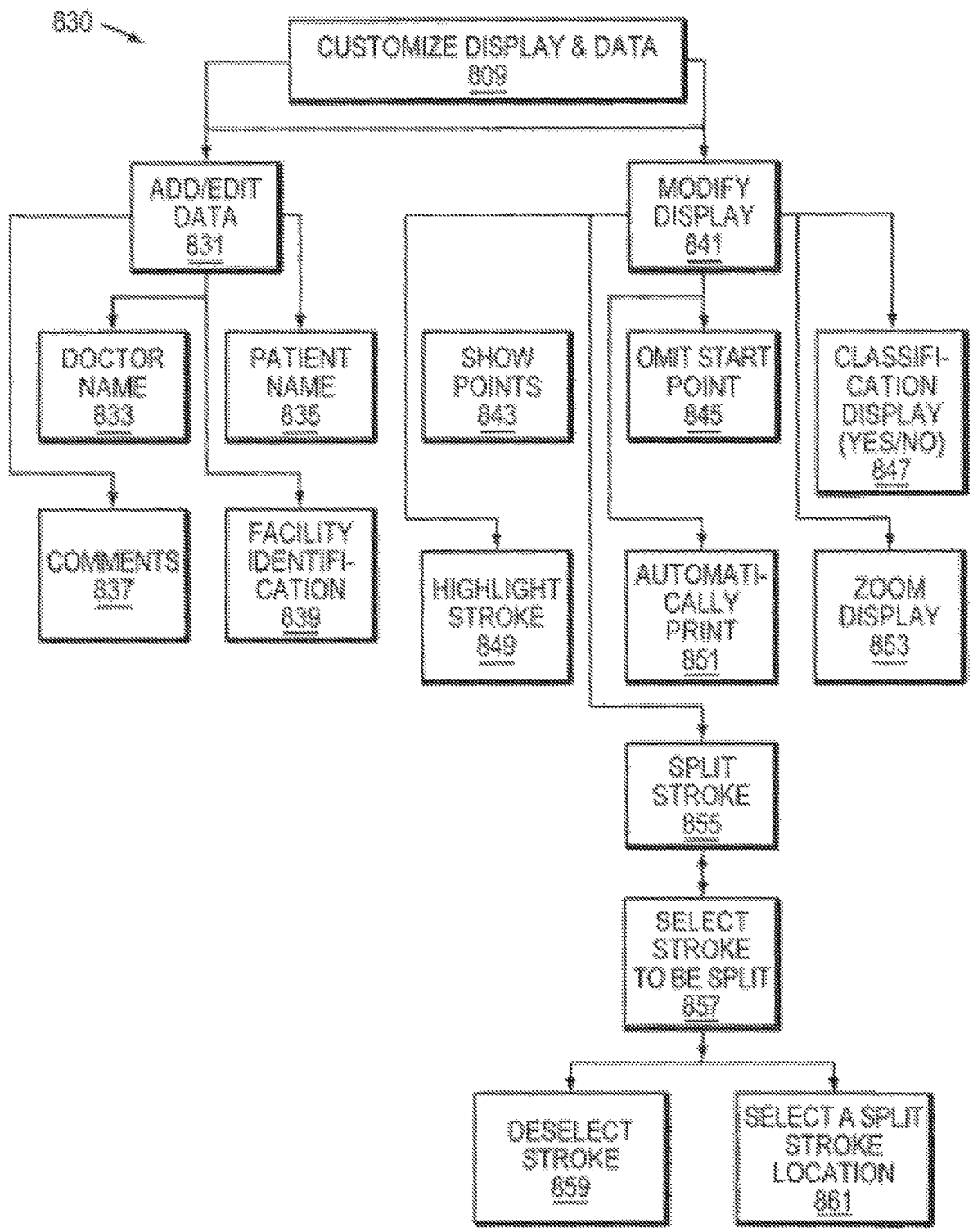
FIG. 8C is a process flow diagram of a user interactive option of the present disclosure to customize the display and data of the motions in accordance with an example disclosure.

FIG. 8C is a process flow diagram 830 of a user interactive option of the present disclosure to customize the display and presentation of data of the motions in accordance with an embodiment of the present invention. The user may be allowed to customize (809) the display and data information, which may include add/edit data (831) or modify the display (841). To add/edit the data (831), the user may add or edit information, such as: doctor name (833), patient name 835, comments 837, or the facility identification (839). To modify the display (841), the user may do at least any of the following: show points, which displays the data points (843); omit start point (845); show or hide the stroke classification display (847); highlight stroke (849); automatically print (851); zoom display (853); or split stroke (855). In one embodiment, when the user opts to split a stroke (835), the user is presented with an option to select the stroke to be split (857). In such a case, the user may either deselect the stroke (859) or select a split stroke location (861).

Figure 9:
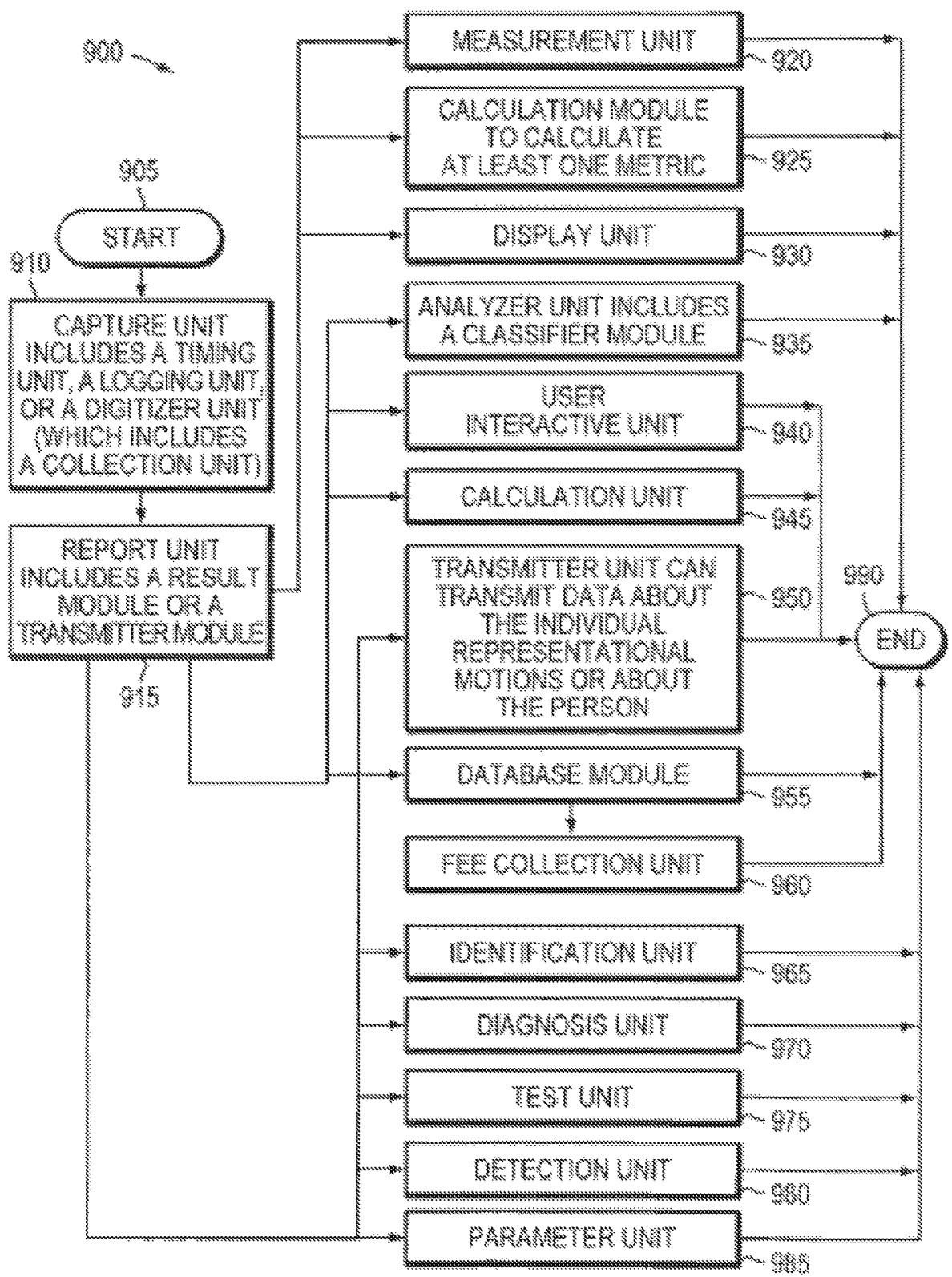
FIG. 9 is a block diagram of an apparatus for measuring representational motions made by a person in accordance with the present disclosure.

FIG. 9 is a block diagram 900 of an example apparatus for measuring representational motions made by a person in accordance with an embodiment of the present invention. When the person begins to perform the neuropsychological test (905), he or she may use a capture unit 910, which may capture the individual representational motions made by the person with spatial precision. The capture unit 910 may include a timing unit, logging unit, or digitizer, which may include a collection unit to collect data from a digitizing stylus used by the person. The capture unit 910 may be coupled to a report unit 915, which may include a result module or a transmitter module. The result module may be used to determine a pass or fail result based on at least one property of the individual representational motions with respect to at least one criterion. The report unit 915 maybe used to report information based on representations of the individual representational motions captured by the capture unit 910.

The following units and modules may or may not be coupled to the capture unit 910 and report unit 915 in any order. A measurement unit 920 may be coupled to the report unit 915, and the measurement unit 920 may be used to measure at least one property of the individual representational motions. A calculation module 925 may be coupled to the report unit 915, and the calculation module 925 may be used to calculate a metric as a function of data representing individual representational motions, known standards associated with the individual representational motions, or data empirically measured that is associated with the individual representational motions.

The report unit 915 may also be coupled to a display unit 930 that may be used to display representations of the individual representational motions or information about the individual representational motions or the person. The display unit 930 may display the representations of the individual representational motions as a single image; chronological sequence; or, chronological sequence in real-time mode, slow motion mode, or fast forward mode. An analyzer unit 935 may also be coupled to the report unit 915. The analyzer unit 935 may be used analyze the individual representational motions based upon spatial, temporal, or geometric properties as well as the chronological sequence in which the person made the representational motions. The analyzer unit 935 may also include a classifier module (not separately shown) that may be used to classify the elements of the individual representational motions as captured and recorded for the person. By classifying the elements of a CDT, the user may observe a person's ability to arrange correctly the numbers of a CDT, which may be an early indication of the cognitive decline of a person. See Clock Drawing at 97.

The report unit 915 may also be coupled to a user interactive unit 940, which may allow the user to indicate misclassifications and classifications made of the representations of the individual representational motions, such as the elements of the CDT. The report unit 915 may also be coupled to a calculation unit 945 that may be used to calculate at least one metric of at least one property of the individual representational motions. The report unit 915 may then report the metric calculated by the calculation unit 945. The calculation unit 945 may also be configured to calculate at least one metric as a function of data representing the individual representational motions, known standard associated with the individual representational motions, or empirical data. A transmitter unit 950 may be coupled to the report unit 915. The transmitter unit 950 may be used to transmit at least one of the following about the individual representational motions made by the person: representations of the individual representational motions; measurements of the at least one property of the individual representational motions; reports of the metric of at least one property; or images, either single image or a chronological sequence, of the individual representational motions.

A database module 955 may be coupled to the report unit 915. The database module 955 may be used to store data about the individual representational motions made by the person. "Data," as used herein, is defined as at least one of the following data based on the individual representational motions: stroke classification, stroke splitting points, or stroke origination, termination, via points, timestamps, or measurement of the at least one property of the individual representational motions. The database module 955 may be configured to respond to user queries and may be coupled to a fee collection unit 960. The fee collection unit 960 may be configured to collect fees and to grant access to metadata or data stored in the database module 955.

An identification unit 965 may be coupled to the report unit 915 and may be used to identify motor or cognitive skill changes in a person, which may be used in a longitudinal study (e.g., daily, weekly, monthly, yearly, etc.) of the person and whether to adjust a pharmaceutical dosage or treatment administered to the person. For example, a longitudinal study was performed on a group of patients suffering from dementia. Clock Drawing at 71. The study found that a person's inability to correctly depict time in a CDT using the clock hands signifies a cognitive impairment. Id. at 73. Additionally, the study showed that the person's ability to perform a CDT deteriorated proportionally with the deterioration of the person's cognitive and functional abilities, which could be useful in determining if a person will need to be institutionalized. Id. at 75. A diagnosis unit 970 may also be coupled to the report unit 915. The diagnosis unit 970 may be used to provide a differential diagnosis of the person. The report unit 915 may also be coupled to a test unit 975, which may be used to identify additional tests that may be administered to the person. A detection unit 980 may be coupled to the report unit 915. The detection unit 980 may be used to detect changes of the implantable interventions in the person. A parameter unit 985 may be coupled to the report unit 915. The parameter unit 985 may be used to change the parameters of implantable interventions in the person based upon at least one property of the individual representational motions. The user may choose at any time to end use of the apparatus to measure motions made by a person in accordance with the present disclosure.

It should be understood that the components (e.g., capture unit 910 or report unit 915) or any of the flow diagrams (e.g., FIG. 8A) may be implemented in hardware, firmware, or software. If implemented in software, it may be implemented in any form of software suitable for use with embodiments of the present invention. The software may be stored on any computer readable medium, such as magnetic or optical disk, RAM, ROM, and so forth, and loaded by a custom general purpose processor to cause the processor to perform operations consistent with embodiments disclosed herein.

Figure 10:
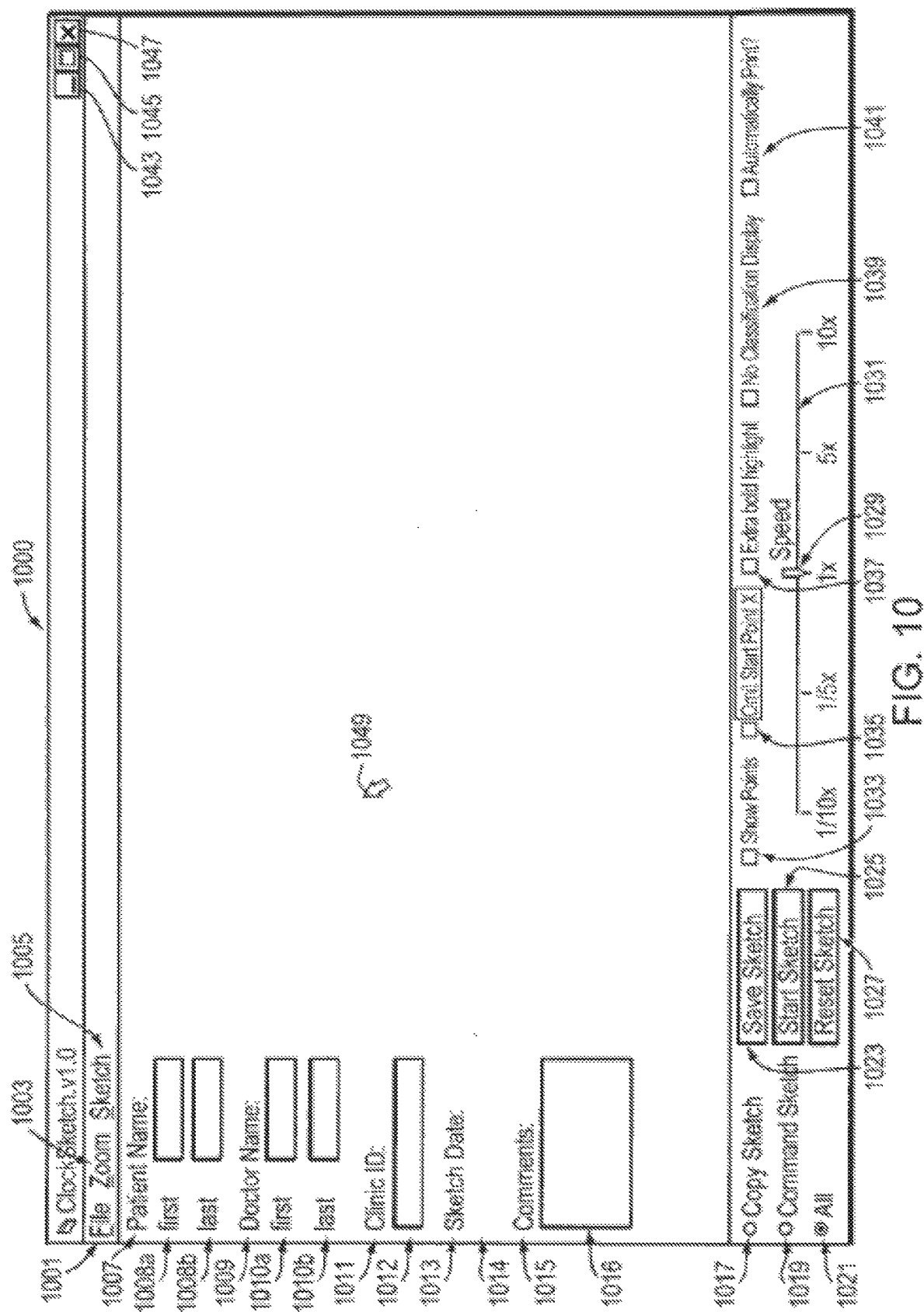
FIG. 10 is an example screen shot of an initial window at program initialization.

FIG. 10 is an example screen shot of a screen 1000 of an initial window at program initialization in accordance with an example embodiment of the present invention. Upon initializing the program, the user may select a File Menu 1001, Zoom Menu 1003, or Sketch Menu 1005. In the left of the screen, the "Patient Name" 1007, "Doctor Name" 1009, "Clinic ID" 1011, "Sketch Date" 1013, and "Comments" 1015 may be displayed. The name of the person may be displayed in the "Patient Name" 1007 section as first name 1008*a* and last name 1008*b*. The name of the doctor may be displayed in the "Doctor Name" 1009 section as first name 010*a* and last name 1010*b*. The location in which the neuropsychological test was or is being administered ("Clinic ID" 1011) may also be displayed 1012. The date on which the neuropsychological test was administered may also be displayed 1014 and may be titled "Sketch Date" 1013. There is an area reserved for "Comments" 1015 to be displayed 1016.

Continuing to refer to FIG. 10, there is a bottom panel which allows the user to interact with the displayed information. The user may select to display a "movie" of the "Copy Sketch" 1017, "Command Sketch" 1019, or all of the sketches 1021 collected from the person, showing the strokes as they were drawn. The user may also select the "Save Sketch" button 1023, "Start Sketch" button 1025, or "Reset Sketch" button 1027. The user may control the speed at which the images are displayed by using a Speed Toolbar 1031, which has a separate control mechanism 1029. By selecting a "Show Points" button 1033, the user is able to display the representations of individual representational motions as created by the person when the neuropsychological test was administered. The user may opt not to display the starting point of the motions made by the person by selecting an "Omit Start Point X" button 1035. The user may also choose to display additional highlighting on the sketch by selecting an "Extra bold highlight" button 1037. If the user does not want to display the classification information for each element of the clock face (see FIG. 2C), the user may select a "No Classification Display" button 1039. The user may also choose to print the displayed information in an automated manner by selecting an "Automatically Print" button 1041. The user may also minimize the screen 1000 by selecting a minimize button 1043, maximize the screen 1000 by selecting a maximize button 1045, or close the screen 1000 by selecting a "close" button 1047. The user may perform any of the aforementioned options by using a cursor 1049, as well known in graphical user interface (GUI) arts.

Figure 11:
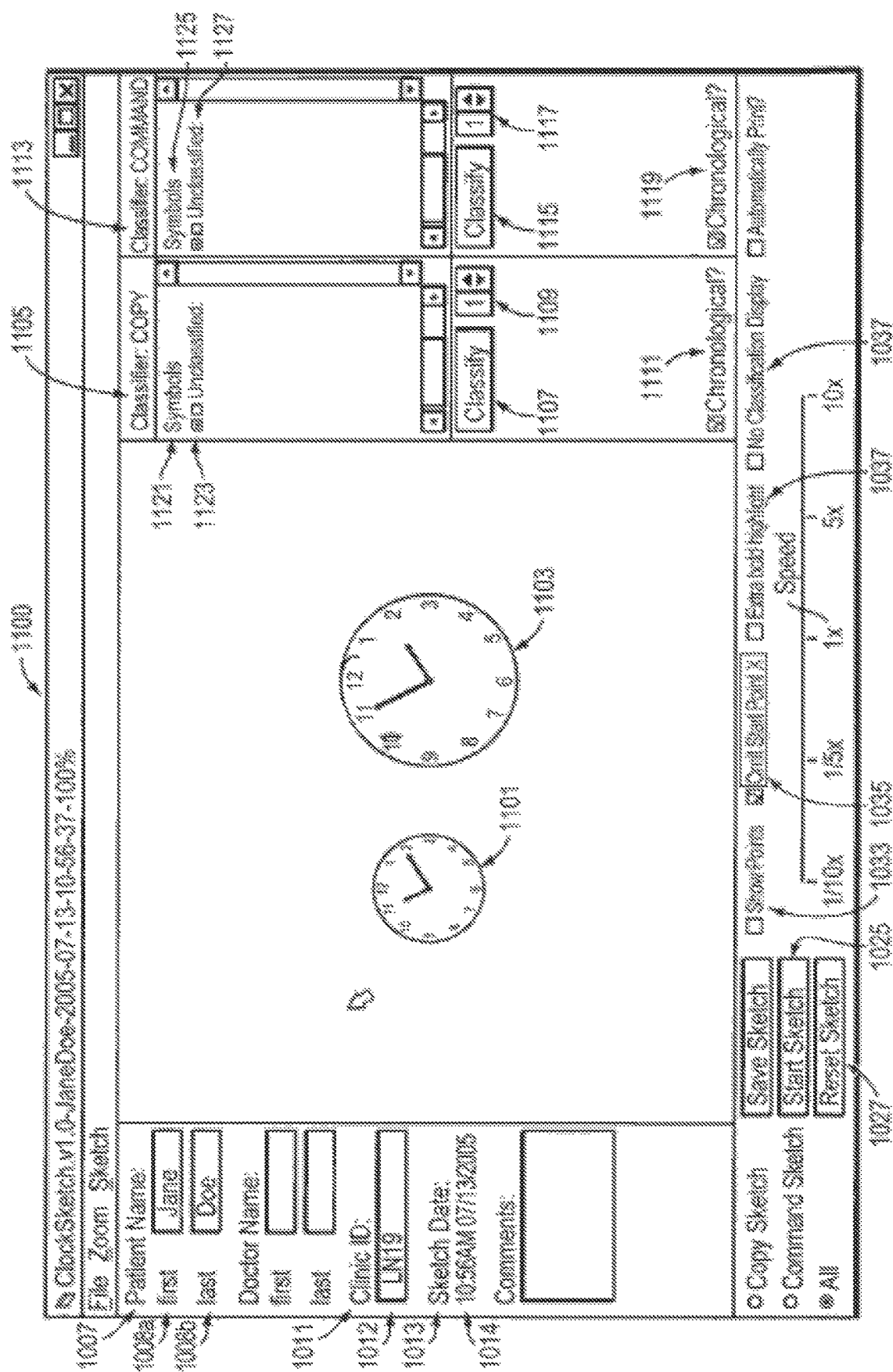
FIG. 11 is an illustrative screen shot presenting data for the motions made by a person.

FIG. 11 is an example screen shot of an initial window 1100 illustrating presentation of data representing the motions made by a person. When the data is loaded, the identification information and the sketch(es) collected, such as clock sketches, may be displayed. In FIG. 11, the identification information included the "Patient Name" 1007, "Clinic ID" 1011, and "Sketch Date" 1013, collected during the test in a format available for automatic default in the fields, or can be entered by a user. The name of the person "Jane Doe" is displayed in the "Patient Name" 1007 section as first name 1008*a* ("Jane") and last name 1008*b* ("Doe"). Additionally, the patient's medical record identifier (represented as "LN19" 1012) is displayed in the "Clinic ID" 1011 section. Lastly, the "Sketch Date" 1013 is displayed as "10:56 AM Jul. 13, 2005" 1014, showing the time and date that the drawing was made.

Continuing to refer to the example embodiment of FIG. 11, the sketch information is displayed as the copy sketch 1101, command sketch 1103, and corresponding classification subfolders 1105 and 1113, respectively. The classification subfolder 1105 for the copy sketch 1101 contains a subfolder for "Symbols" 1121 and a corresponding folder titled "Unclassified" 1123, which contains the collected data for each element of the sketch. Each element (meaning, "1," "2," hour hand, etc.) may be classified using the "Classify" button 1107 and the element selection menu 1109. The classification information for each element (or symbols) of the clock face may be displayed in chronological order by selecting the "Chronological?" button 1111 or the classification information may be displayed in non-chronological order by deselecting the same button 1111. Likewise, the classification subfolder 1113 for the command sketch 1103 contains a subfolder for "Symbols" 1125 and a corresponding folder titled "Unclassified" 1127, which contains the collected data for each element of the sketch. Each element (meaning, "1["] "2["] hour hand, etc.) may be classified using the "Classify" button 1115 and the element selection menu 1117. The classification information for each element of the clock face (or symbols) may be displayed in chronological order by selecting the "Chronological?" button 1119 or the classification information may be displayed in non-chronological order by deselecting the same button 1119. Lastly, in the lower panel of the screen, the "Save Sketch" button 1025 and "Reset Sketch" button 1027 are illustrated in an activated state. Also, the "Show Points" button 1033, "Omit Start Point X" button 1035, which has been selected in FIG. 11, "Extra bold highlight" button 1037, and "No Classification Display" button 1039 are illustrated in an activated state.

Figure 12:
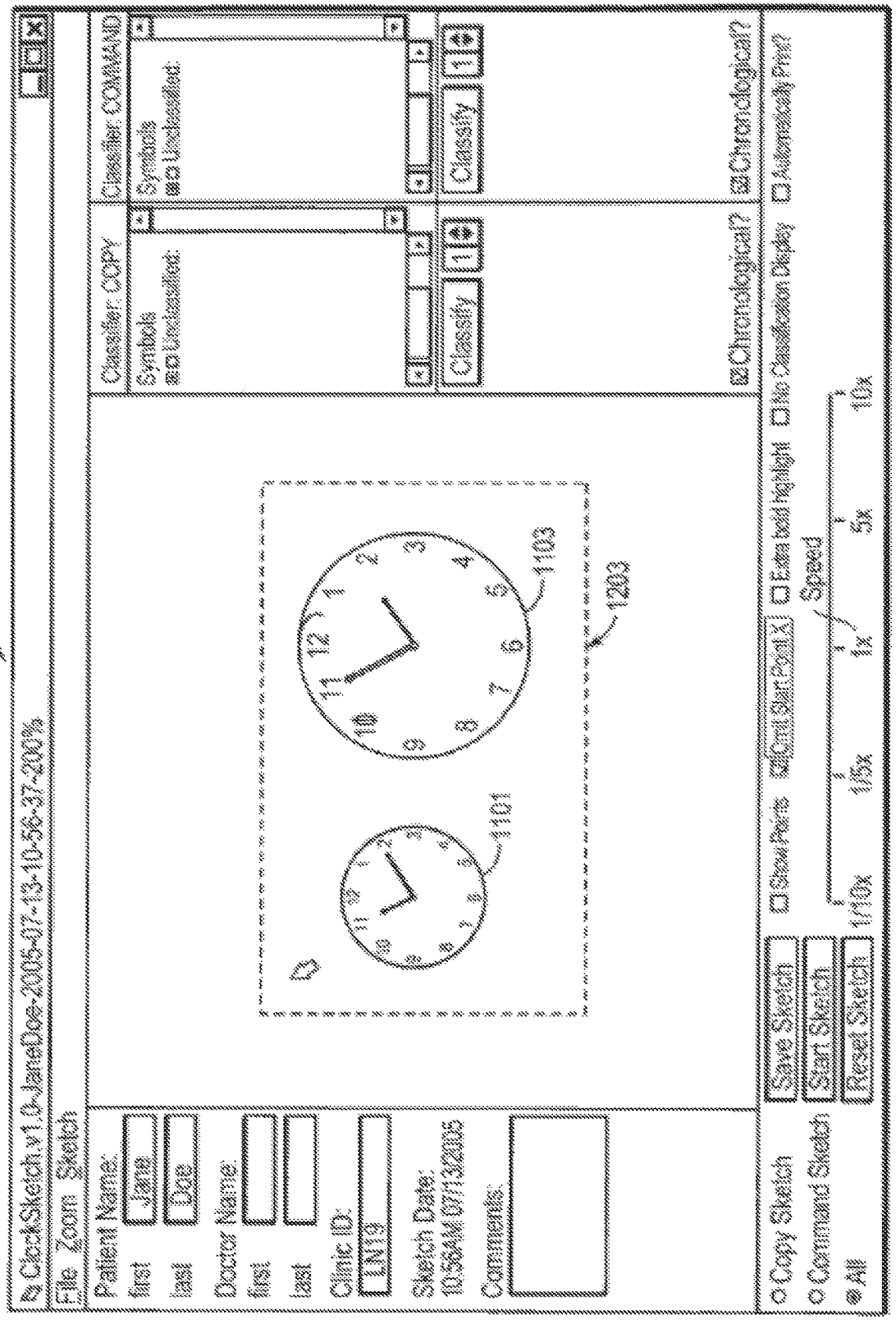
FIG. 12 is an illustrative screen shot of the data of FIG. 11 following a zoom request of the loaded data by the user.

FIG. 12 is an example screen shot of a GUI 1200 illustrating the option to "zoom in" on loaded data for the motions made by a person in accordance with the example embodiment. The "zoom in" display 1203 allows closer viewing of the copy sketch 1101 and command sketch 1103 as displayed in FIG. 11. In current practice, a proctor may provide the examinee with a pre-drawn circle if the patient is unable to draw a circle or draws a circle that is too small or distorted. Clock Drawing at 7. If a clock face of a CDT is distorted, small, or asymmetrical, the examinee may be unable to draw or arrange the numbers or clock hands. Id. However, the present disclosure may resolve the aforementioned issue by providing the examiner (or user) with a zoom option to "zoom in" on an examinee's completed or attempted CDT. Id. If a person is unable to draw a circle that is large enough for the completion of a CDT, the person may suffer from micrographia, which is a symptom of a deficit associated with multiple neurological conditions including subcortical white matter disease, hydrocephalous, Parkinson's Disease, stroke and in the basal ganglia. See Id. The presence of micrographia can be crucial in the common diagnostic question of depression (i.e., pseudo dementia) in contrast to dementia. Depressed patients can look as if they are dementing, and can have slowed motor movement (or psychomotor retardation), like a person with subcortical deficit, but will not have micrographia.

Figure 13:
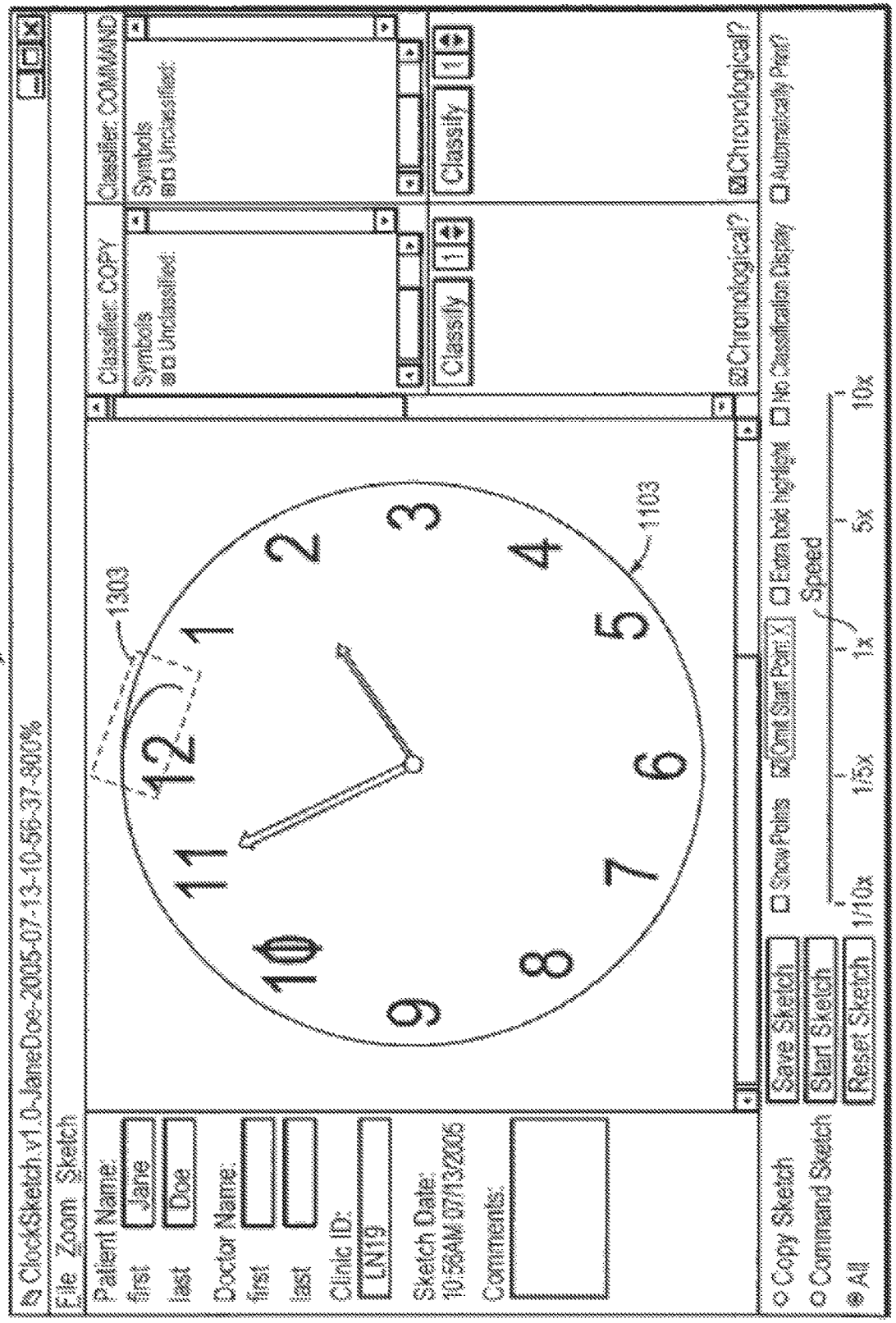
FIG. 13 is the screen shot of FIG. 12 following a zoom request of a particular section of the loaded data by the user.

FIG. 13 is an example screen shot of a GUI 1300 illustrating the option to "zoom in" on a particular section of loaded data captured and recorded for the motions made by a person in accordance with an example embodiment. FIG. 13 illustrates that the program may be used to "zoom in" to the display to allow for viewing further detail of any elements being presented, such as the command sketch 1103, as shown. Such an option is useful to observe an overlap of the start and end 3303 of the clock face, for example, because such an overlap can be caused by perseveration, which may be an indication that the person may suffer from a brain injury or other physical brain disorder (e.g., vascular dementia). See Clock Drawing at 45. The overlap is slightly noticeable in FIG. 11 when the data was originally loaded, but the overlap is particularly observable in FIG. 13 through use of the "zoom in" option. In scoring clock drawings, seven categories of errors have been observed, which are: "omissions, perseverations, rotations, misplacements, distortions, substitutions, and additions." Id. at 46. An example embodiment of the present invention allows many other types of "errors" to be observed, such as slow time, pauses, hooklets or lack thereof, and number of strokes.

Figure 14:
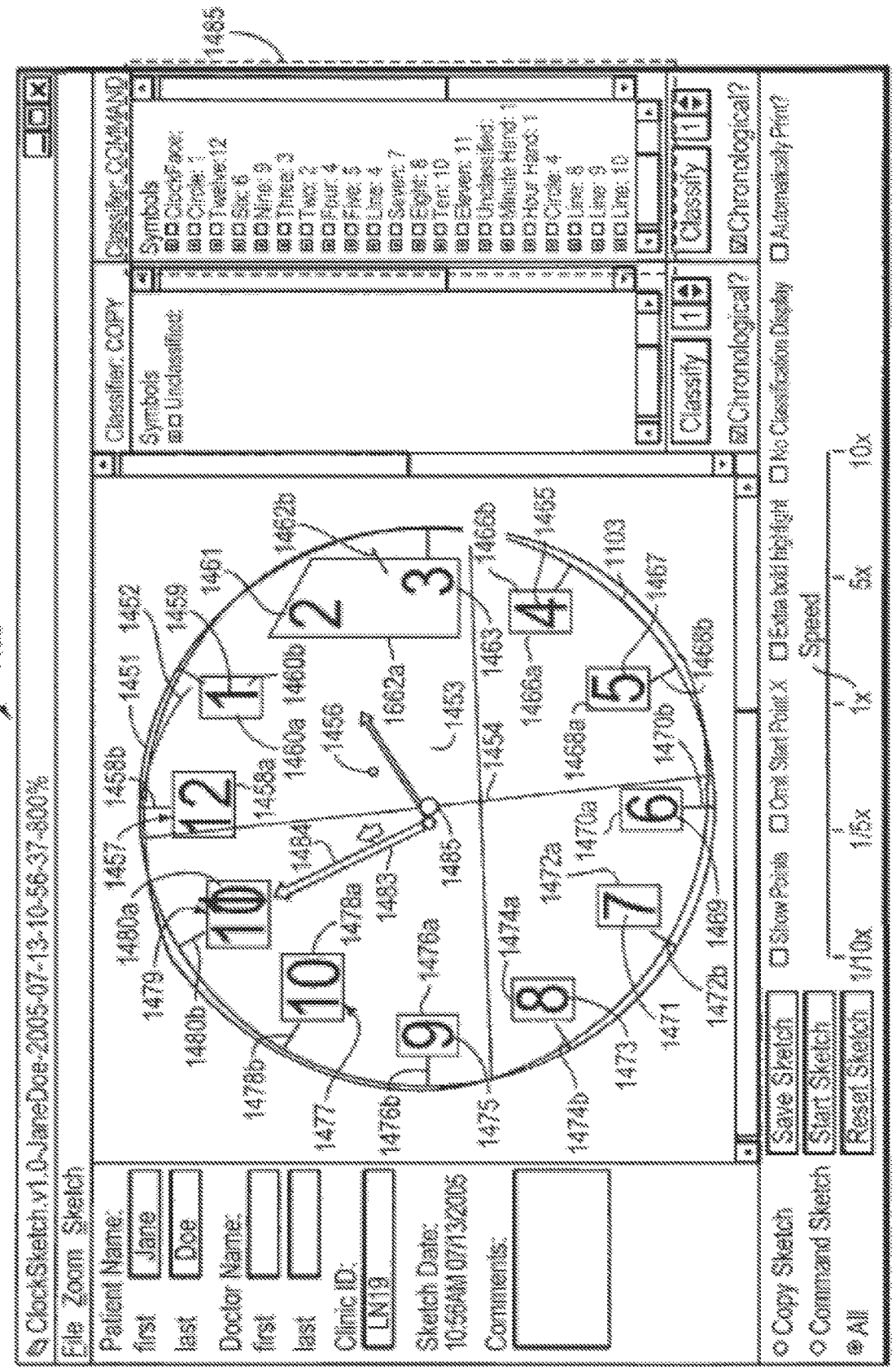
FIG. 14 is an example screen shot highlighting a classification of each symbol of the clock as drawn by a person in accordance with an example embodiment of the present disclosure.

FIG. 14 is an example screen shot of a GUI 1400 illustrating annotations of classification of each symbol of the clock 1103 as drawn by a person in accordance with an example embodiment of the present invention. In FIG. 14, certain elements of the clock 1103 have been approximated with an ideal corresponding element. For example, the clock face 1451 is drawn by the person and the present embodiment may approximate the clock face with an ellipse or circle 1452 that best fits the clock face 1451. The ellipse or circle has a major axis 1453 (major axis center 1455) and a minor axis 1454 (minor axis center 1456). Additionally, each number on the clock face 1451 is placed inside of a "bounding box" (or box) that is a rectangle with horizontal or vertical sides that are just large enough to enclose the number. The following is a list of the numbers with its corresponding box: "12" 1457 (box 1458a, line 1458b), "1" 1459 (box 1460a, line 1460b), "2" 1461 and "3" 1463 (box 1462a, line 1462b), "4" 1465 (box 1466a, line 1466b), "5" 1467 (box 1468a, line 1468b), "6" 1469 (box 1470a, line 1470b), "7" 1471 (box 1472a, line 1472b), "8" 1473 (box 1474a, line 1474b), "9" 1475 (box 1476a, line 1476b), "10" 1477 (box 1478a, line 1478b), and "11" 1479 (box 1480a, line 1480b). A hand drawn hour hand 1481 is approximated in the present embodiment with a computer rendered arrow 1482 that best fits the hand drawn hour hand 1481. A hand drawn minute hand 1483 is approximated in the present embodiment with a computer rendered arrow 1484 that best fits the hand drawn minute hand 1483. The classification information for the command sketch 1103 is displayed in the corresponding classification subfolder 1485.

Figure 15:
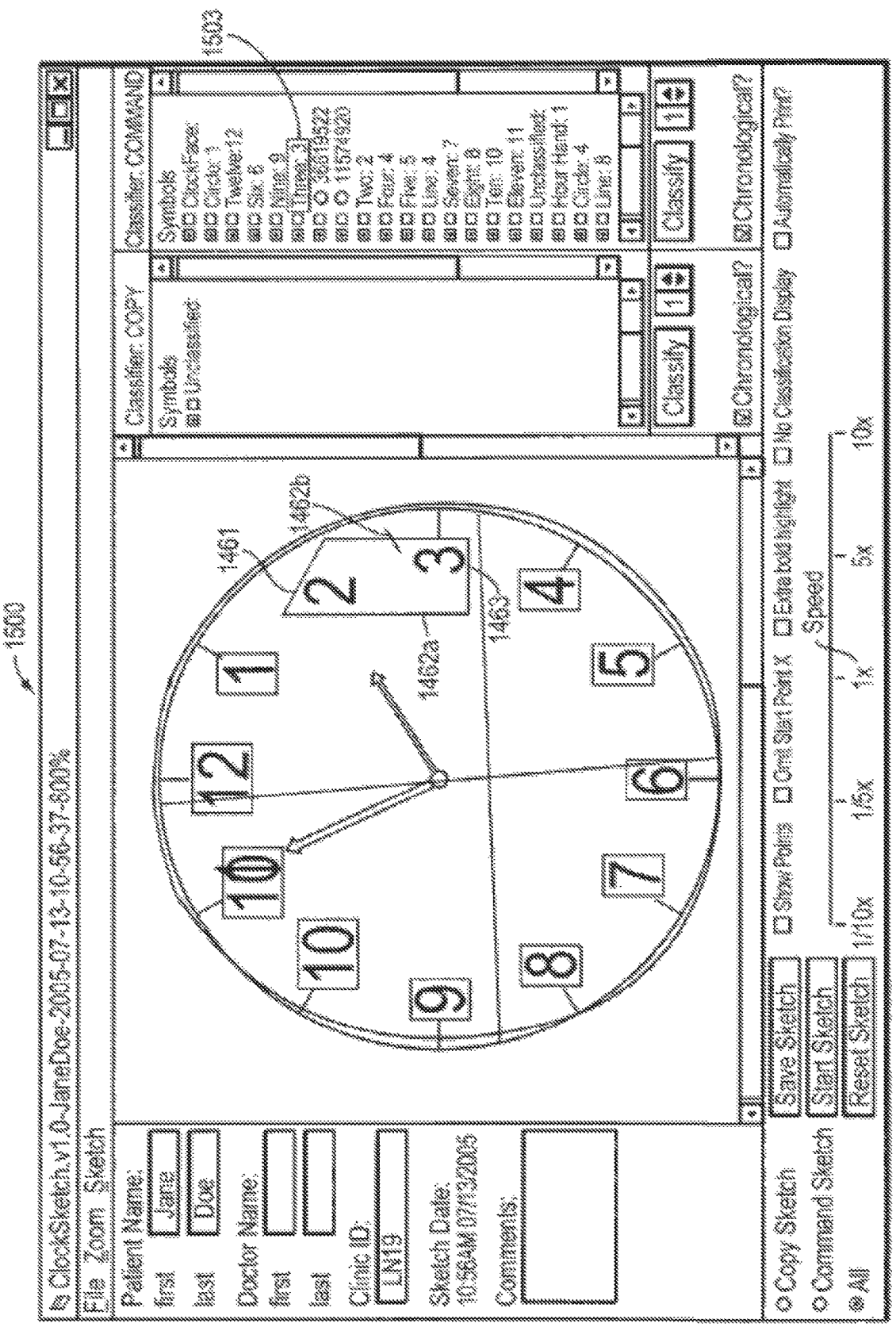
FIG. 15 is an illustrative screen shot of highlighted misclassifications of motions made by a person in preparation for user interactive correction.

FIG. 15 is a screen view of a GUI 1500 illustrating misclassifications of motions that have been highlighted by the user in preparation for user interactive correction. The misclassification occurred where the bounding box 1462a was fit to enclose numerals "2" 1461 and "3" 1463, which are highlighted in the current figure. The classification information for number "3" is also highlighted 1503.

Figure 16:
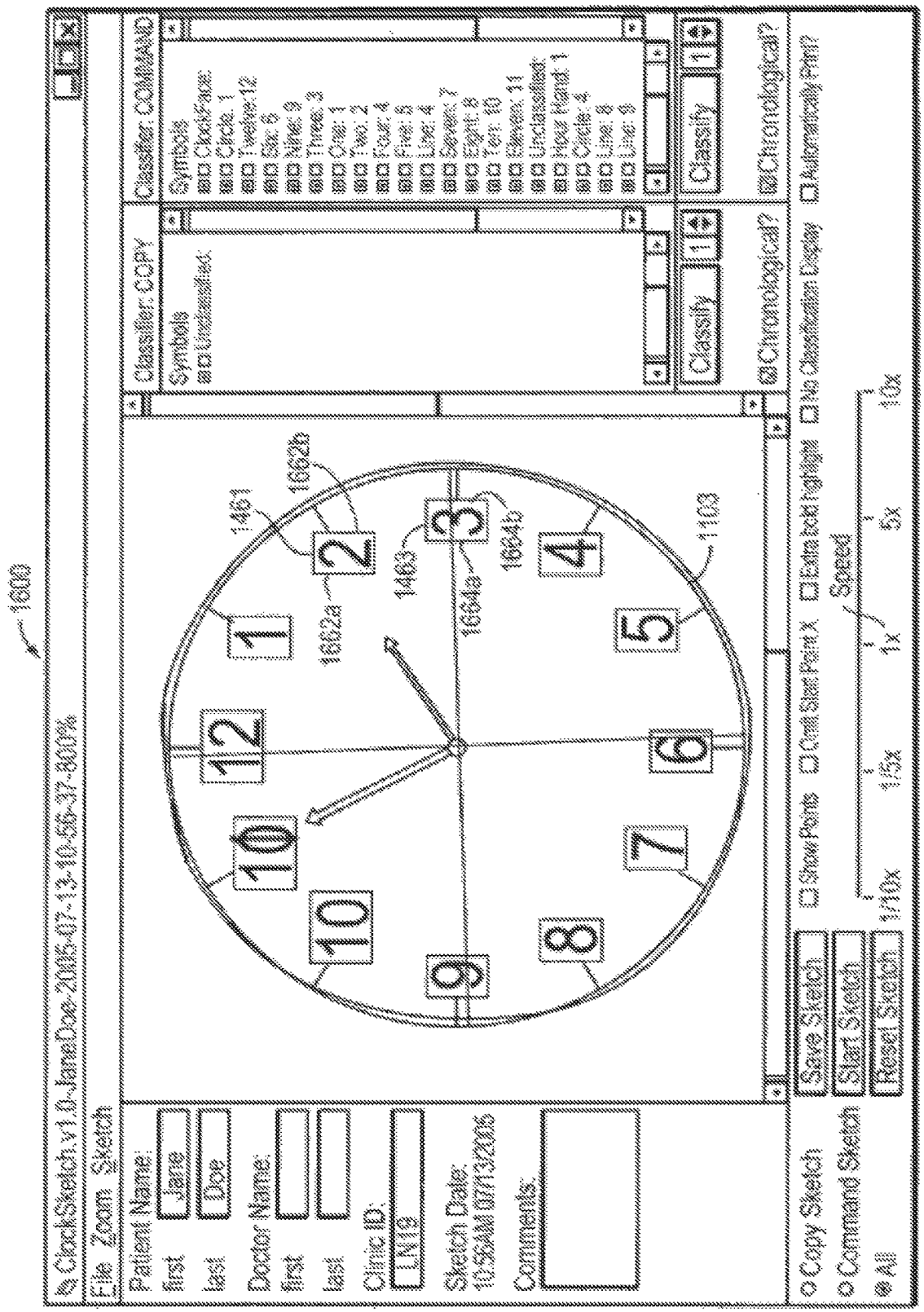
FIG. 16 is an example screen shot of a corrected misclassification of motions made by a person in accordance with the present disclosure.

FIG. 16 is an example screen shot of a GUI 1600 illustrating corrected misclassification of motions, corrected by the user in accordance with the present disclosure. Based upon information input by the user, the program corrects the classification of the numeral "2" 1461 by placing a new computer bounding box 1662a and line 1662b around the numeral "2" 1461. Likewise, the numeral "3" 1463 was rebounded with a new box 1664a and line 1664b.

Currently, practitioners have difficulty in establishing a standard range of accuracy to measure a person's arrangement of clock hands and numbers because of inconsistencies between shape, size, and arrangements of features of a CDT. Clock Drawing at 23. In contrast, the present disclosure establishes standards based upon numerous features of a CDT, such as geometrical, spatial, temporal, or angular displacements or relationships between representations of individual representational motions as made by the person (see Table 1).

Figure 17:
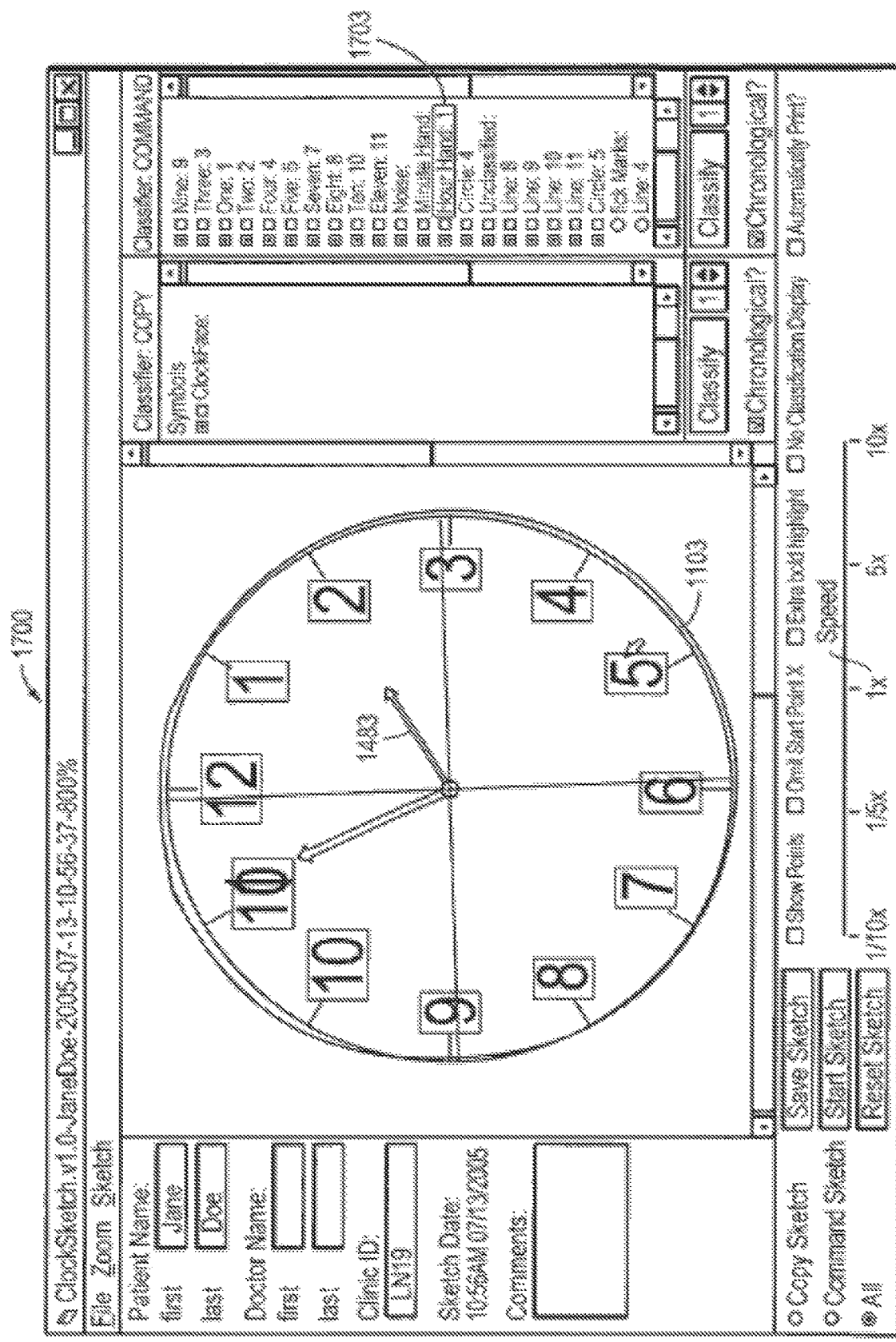
FIG. 17 is an illustrative screen shot of completed classification of motions made by a person in accordance with the present disclosure.

FIG. 17 is an illustrative screen shot of a GUI 1700 with highlights of an element of a clock face made by a person in accordance with the present disclosure. The hour hand 1483 of the command sketch 1103 is shown in a highlighted state. In this embodiment, if the user selects the classification information 1703 for the hour hand 1483, the hour hand 1483 is highlighted in the display 1700.

Figure 18:
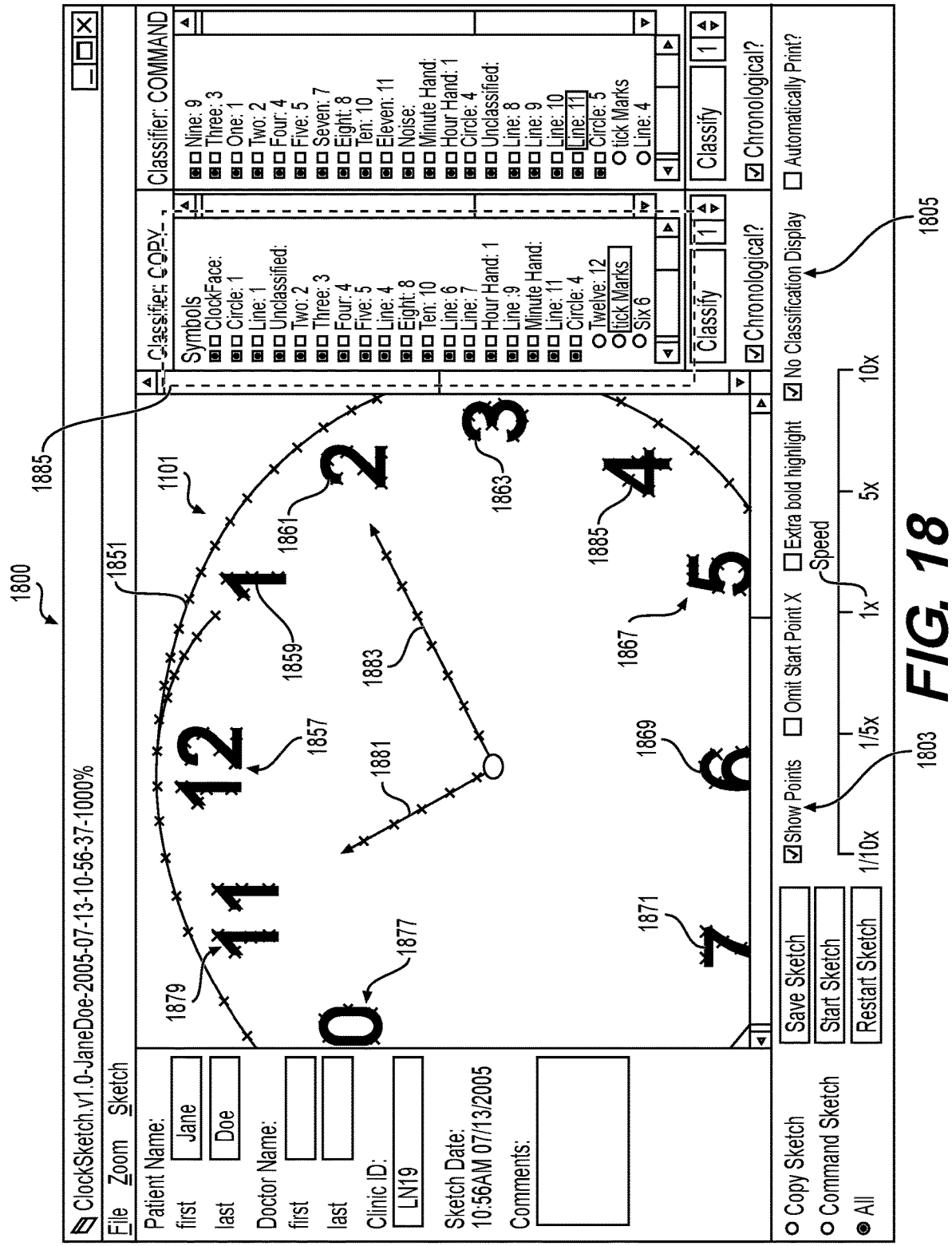
FIG. 18 is an example screen shot of a "zoom in" option as well as an option to display data points in accordance with the present disclosure.

FIG. 18 is an example screen shot of a GUI 1800 illustrating a "zoom in" option, option to display data points, and classification option in accordance with an example embodiment of the present disclosure. FIG. 18 illustrates that a user may "zoom in" on the display 1800, which is represented here as a close-up view of the copy sketch 1101. The user may also choose to display the data points of the sketch by selecting the "Show Points" button 1803, but not to display the classification information by selecting the "No Classification Display" button 1805. The clock face 1851 as drawn by the person is displayed using each individual data point collected by a capture unit. Additionally, each number on the clock face 1851 is displayed using each individual data point collected by the capture unit. The following is a list of the numerals as displayed in FIG. 18 with each numeral's corresponding data points: "12" 1857, "1" 1859, "2" 1861, "3" 1863, "4" 1865, "5" 1867, "6" 1869, "7" 1871, "10" 1877, and "11" 1879. The hour hand 1881 and the minute hand 1883 are displayed using each individual data point collected by the capture unit. The classification information for the copy sketch 1101 is displayed in the corresponding classification subfolder 1885.

Figure 19:
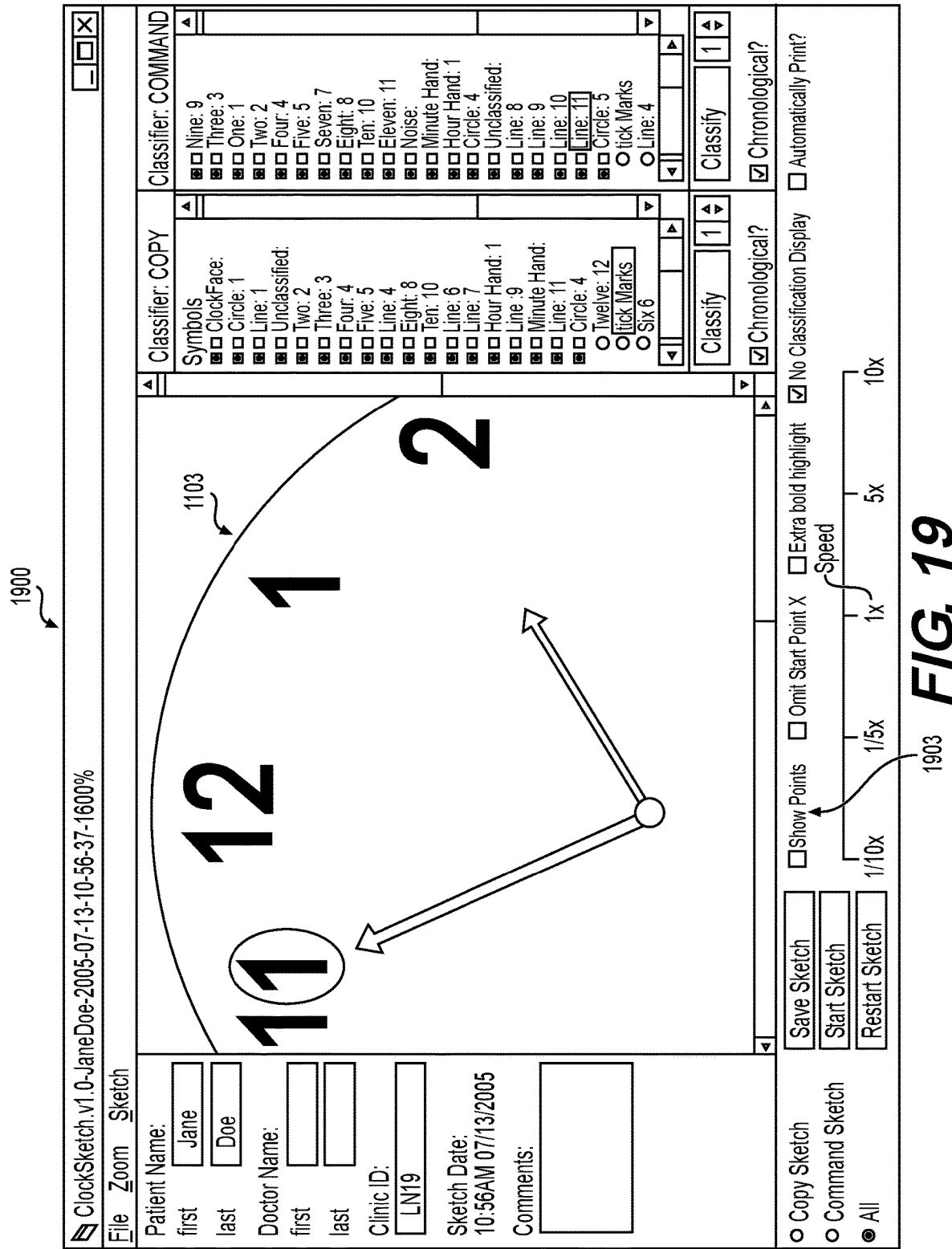
FIG. 19 is an illustrative screen shot of a "zoom in" option in preparation to split a stroke made by a person in accordance with the present disclosure.

FIG. 19 is an illustrative screen shot of a GUI 1900 illustrating a "zoom in" option in preparation to split a stroke made by a person in accordance with the present disclosure. The figure illustrates that a user may "zoom in" on the command sketch 1103 in preparation to split a stroke. The "Show Points" button 1903 is illustrated in a deactivated state.

Figure 20:
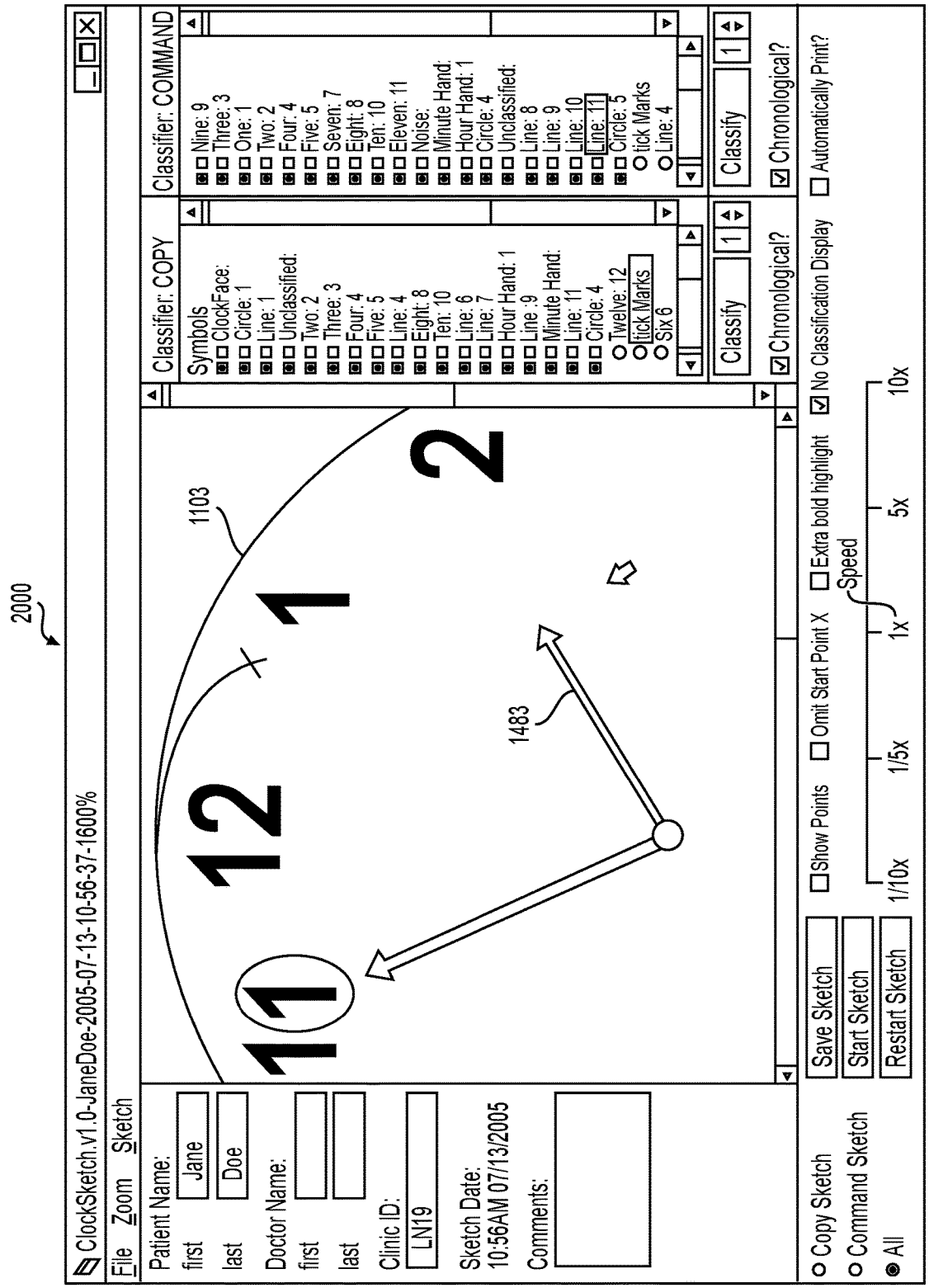
FIG. 20 is an example screen shot of the option to split a stroke in which the selected stroke is highlighted in accordance with the present disclosure.

FIG. 20 is an example screen shot of a GUI 2000 illustrating the option to split a stroke in which the selected stroke is highlighted in accordance with the present disclosure. The figure illustrates that a user may select an element of the command sketch 1103, such as the hour hand 1483 (as shown), as a location to split a stroke.

Figure 21:
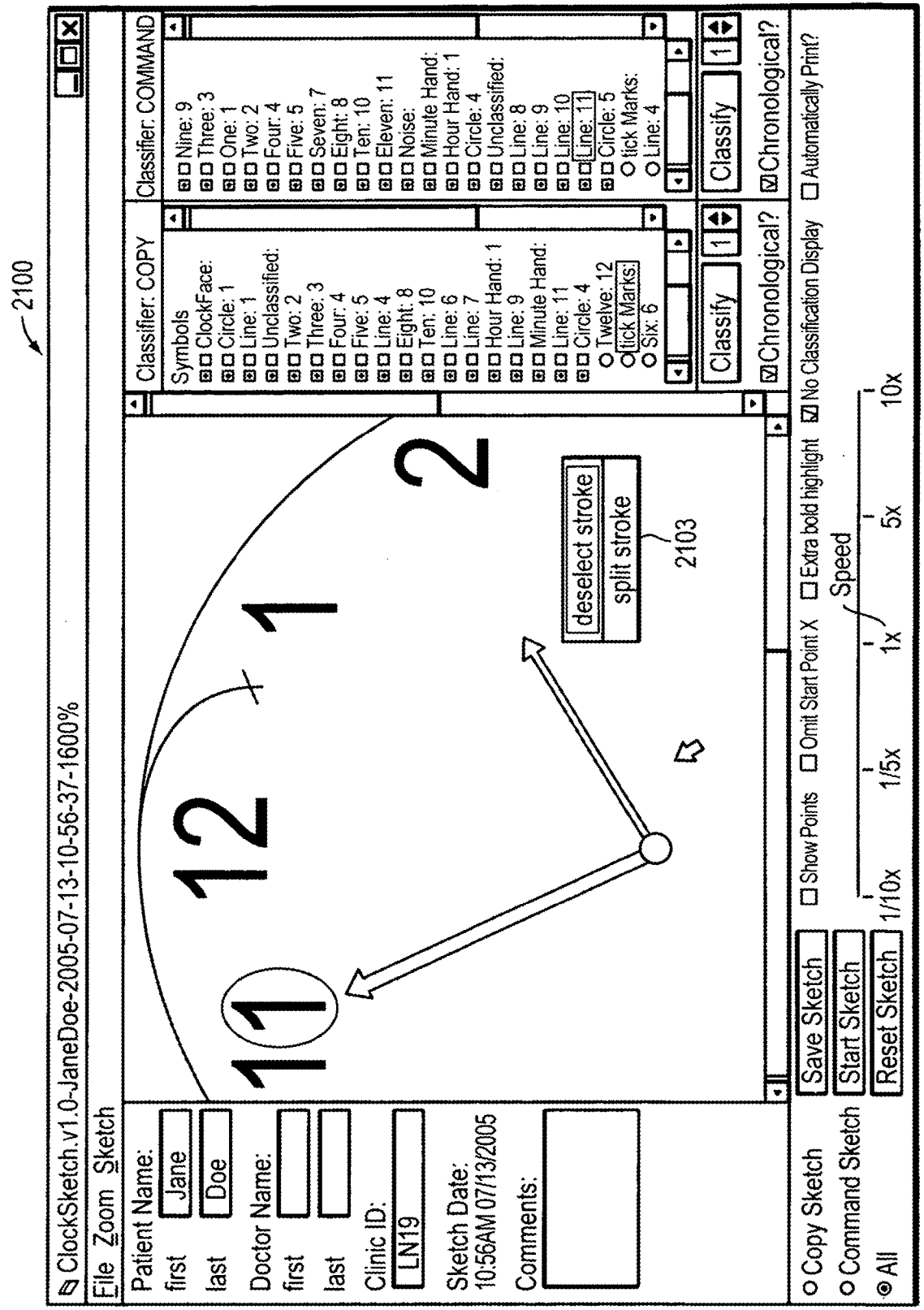
FIG. 21 is an example screen shot of a pop-up window to allow the user to select a stroke interactively to split the stroke or to select a new stroke split location in accordance with the present disclosure.

FIG. 21 is an example screen shot of a GUI 2100 illustrating a pop-up window to allow the user to select interactively a stroke to split or to select a new stroke split location in accordance with the present disclosure. When a user opts to split a stroke, a pop-up window 2103 appears and presents the user with an option to "deselect the stroke" or to "split [the] stroke."

Figure 22:
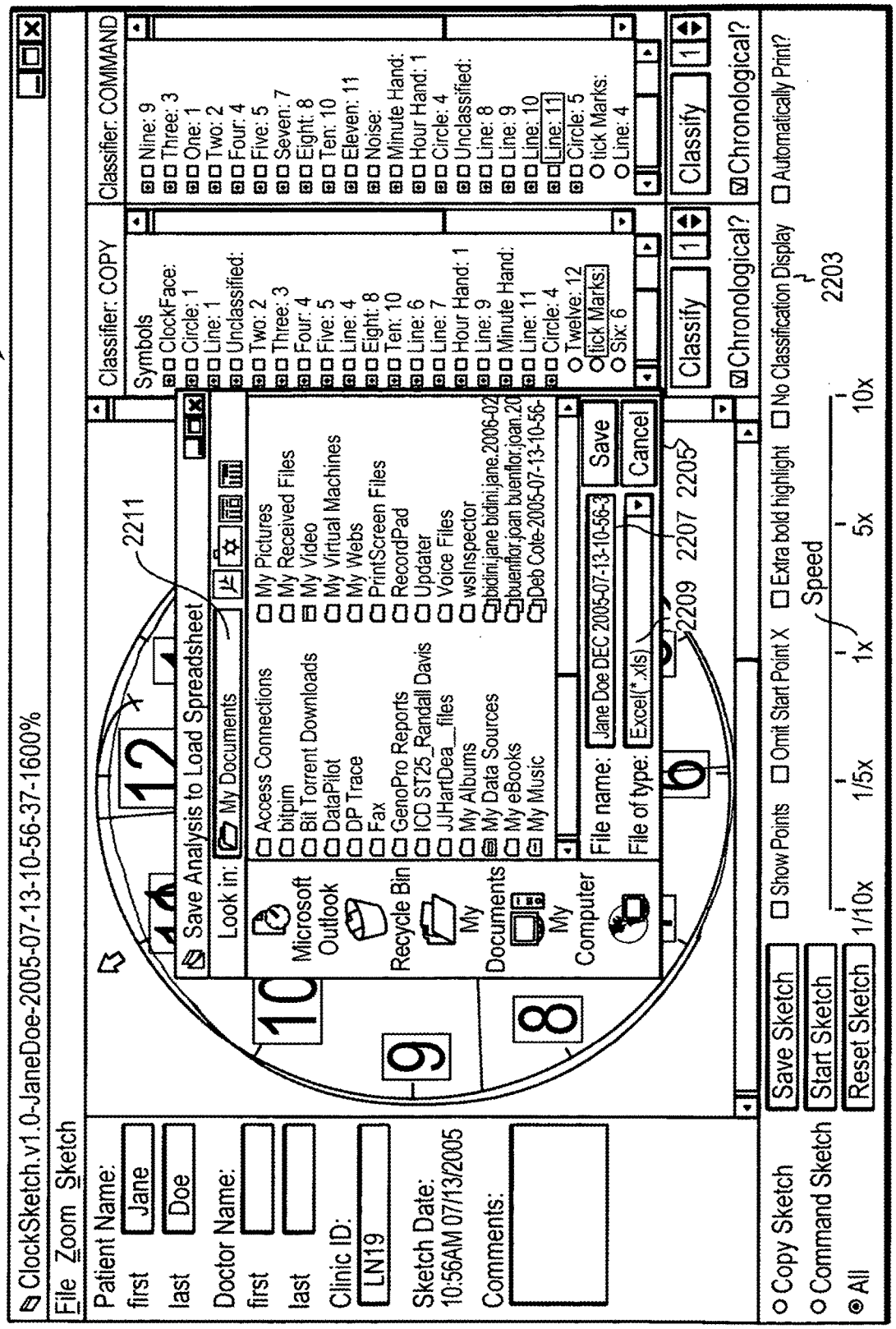
FIG. 22 is an example screen shot of a pop-up window to allow a user to produce a spreadsheet with detailed analysis of a classified clock drawing in accordance with the present disclosure.

FIG. 22 is an example screen shot of a GUI 2200 illustrating a pop-up window to allow a user to produce a spreadsheet with detailed analysis of a classified clock drawing in accordance with the present disclosure. In FIG. 22, the "No Classification Display" button 2203 is illustrated in a deactivated state. To allow a user to save the analysis as a spreadsheet, a pop-up window 2205 appears. The pop-up window 2205 allows the user to select the "File Name" 2207 as well as the type of file 2209 to be saved. The user may also select the location 2211 where the spreadsheet is to be saved.

Referring to FIG. 23a-FIG. 23c, a table provides an example of a spreadsheet of detailed analysis of a classified clock drawing in accordance with the present disclosure. Table 1 is provided as an example of data analysis, but the data presented is not an exhaustive listing of data that may be provided in accordance with the present disclosure.

As introduced above, a variety of features can be determined from the user's input in performing the drawing task, and one class of those features relates to the dynamic characteristics of representational motions. Examples of dynamic characteristics associated with representational motions include but are not limited to acceleration of motion, velocity of motion, activity and inactivity time of motion, and so on. The features may relate to the drawing task as a whole and/or may relate to individual elements (e.g., a circle, a clock hand, etc.). A selection of features representing an execution of the drawing task by a subject may be represented as a real-valued vector.

As introduced above, automated extraction of the feature values from an execution of the drawing task may be followed by automated generation of a report based on those feature values. In some examples, to derive diagnostic information in a report from the features of the representational motions described above, a mapping between the features of the representation motions and diagnoses is established based on previous executions of the task. For example, drawing task results for a group of known healthy subjects and a group of subjects known to have a particular neurocognitive disorder are collected. The test results for both groups include features related to as dynamic characteristics of representational movements. The test results are appropriately labeled as normal versus disordered and are provided to a machine learning algorithm (e.g., a support vector machine training algorithm) which trains a model using the test results. In some examples, the model is represented as a set of model parameters. The trained model is provided to a classifier (e.g., a support vector machine) which, given a test result for a subject, can predict a diagnosis based on the test results. Other forms of mapping may be used, for example, based on other parametric or non-parametric statistical techniques, Bayesian modeling and the like.

In some examples, all the measured features may be provided to the machine learning algorithm to train the model. In other examples, only selected features, or derived features, are used. In some such examples, an expert chooses certain features which are known to be or believed to be correlated with certain diagnoses and only the chosen features are provided to the machine learning algorithm to train the model.

In some examples, the dynamic characteristics of a representational motion are analyzed to determine information known or believed to be related to the neurocognitive mechanisms underlying the representational motion which may not be apparent to a trained eye of a doctor. For example, if a representational motion made by a user during a clock drawing test includes a relatively long time of inactivity when the user is attempting to arrange the numbers on the clock face, the inactivity time associated with the representational motion may be indicative the presence of a neurocognitive disorder. In another example, a representative motion made by a user when attempting to draw a circular face of a clock may include a failure to decelerate when completing the circle. Such a failure to decelerate can be used to differentiate between different neurocognitive disorders such as vascular dementia and fronto-temporal dementia. Yet another feature known or believed to be significant in the clock drawing task is a "pre first hand latency" defined as the delay before the drawing of the first hand of the clock.

Certain features that are automatically extracted from the subject's execution of the drawing task relate to occurrences of particular elements. One example of such an element, which can be determined from the user's input in performing a drawing task is referred to herein as a "hooklet." A hooklet is defined as a sharp turn at an end of a writing stroke which points toward the next stroke that the user intends to make. Hooklets are generally indicative of planning and a change in a number of hooklets drawn by a user may be an early sign of decreased executive function. Thus, the mere presence or absence of hooklets in the representational motions made by the user can indicate the presence or absence of a neurocognitive disorder. Therefore, the set of measured features may include a number of hooklets. Furthermore, features of hooklets such as the speed with which a hooklet was made, the length of a hooklet, the total number of hooklets, the size of a hooklet relative to a stroke associated with the hooklet, and the distance between the end of a hooklet and the beginning of the next stroke can be used in the set of features as providing diagnostic information related to neurocognitive disorders.

As introduced above, successive executions of the same or related drawing tasks or executions of sub-tasks within one larger task by a particular subject may provide information that is not available in a single execution of the task. For example, successive executions of the same drawing task by a subject over an extended time (e.g., once a week, once a month) may provide evidence of a progression of a disorder. In some such examples, the features of each execution are compared to previously determined mapping or models, for example, providing a measure of a degree of correspondence of the features with the model or mapping associated with a disorder. This degree of correspondence may be tracked over time to determine progression of the disorder. In some examples, the features themselves are compared between executions. For example, the progression of overall execution time, drawing time, "thinking"/idle time, or other features may provide an indication of progression of a disorder. In some examples, the successive executions may be related to different states of the subject, for example, with different levels of medication, with different types of intervention (e.g., neural stimulation), etc., and the comparison of the different executions may provide information about the different states of the subject (e.g., the effectiveness of medication or intervention).

In some examples, comparison of successive executions of drawing tasks may provide evidence of neurocognitive characteristics of the subject. In one such example, a first drawing task is executed by the subject, and then shortly thereafter, the subject performs the same or a related drawing task. The first execution provides a "priming" of the subject for the second execution. A comparison of features of the two executions may provide evidence related to functions such as memory or planning. In one simple example, a second execution of the same task may be somewhat faster than the first execution by a normal subject, and may take approximately the same amount of time for a subject with deficiencies in their memory functions.

Figure 24:
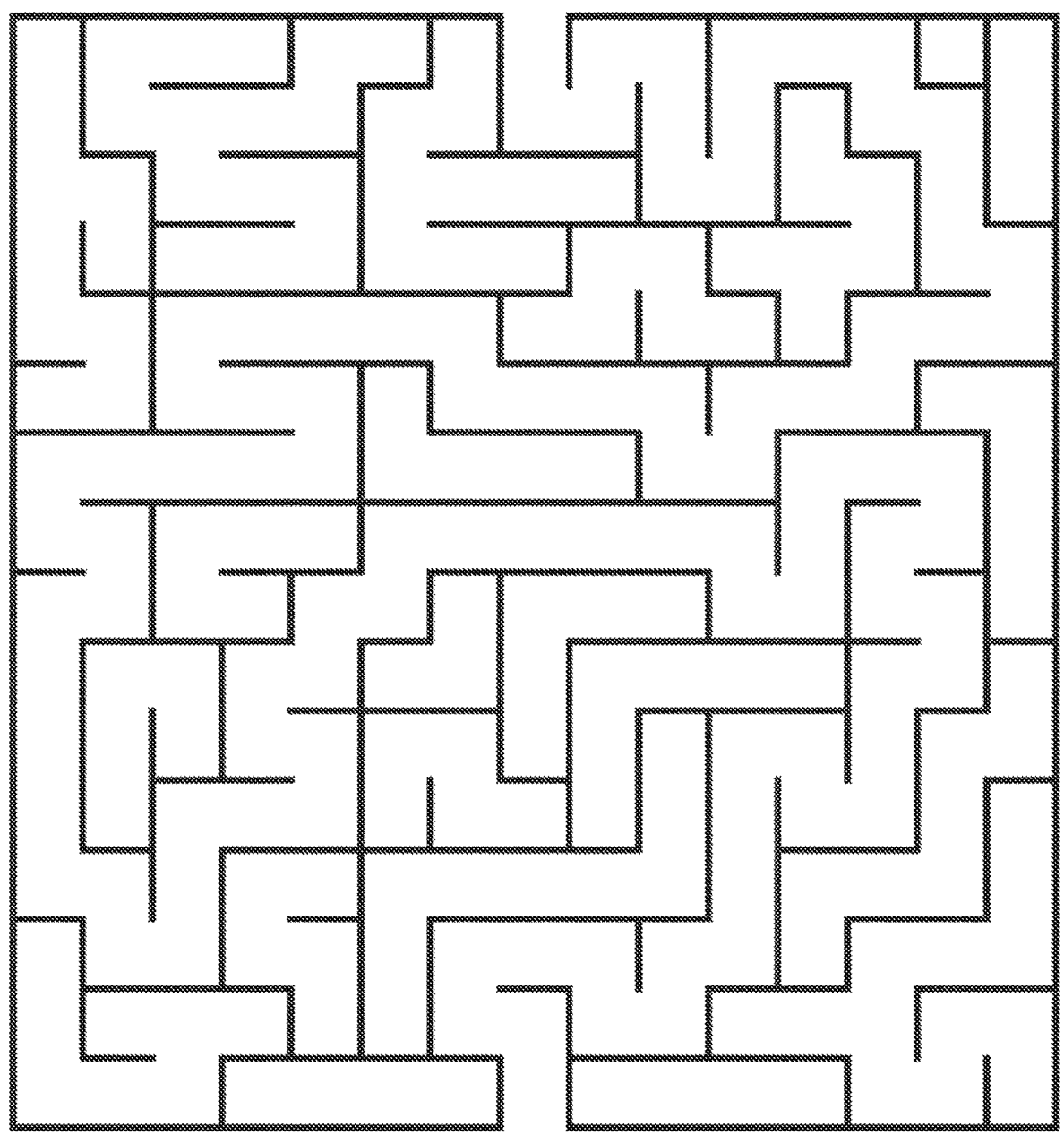
FIG. 24 is an illustration of a maze drawing task.

A type of drawing task that is particularly adapted to comparison of features of successive executions is based on the subject tracing a path through a maze. The characteristics of these executions can be indicative of neurocognitive disorders. Referring to FIG. 24, one such task includes first having a test subject draw a path through a first maze 2400 which has no decision points (i.e., the test subject can not diverge from the correct path through the maze). By making the test subject go through the first maze 2400 once, the subject is said to be "primed" since they become familiar with the correct solution to the first maze 2400.

Figure 25:
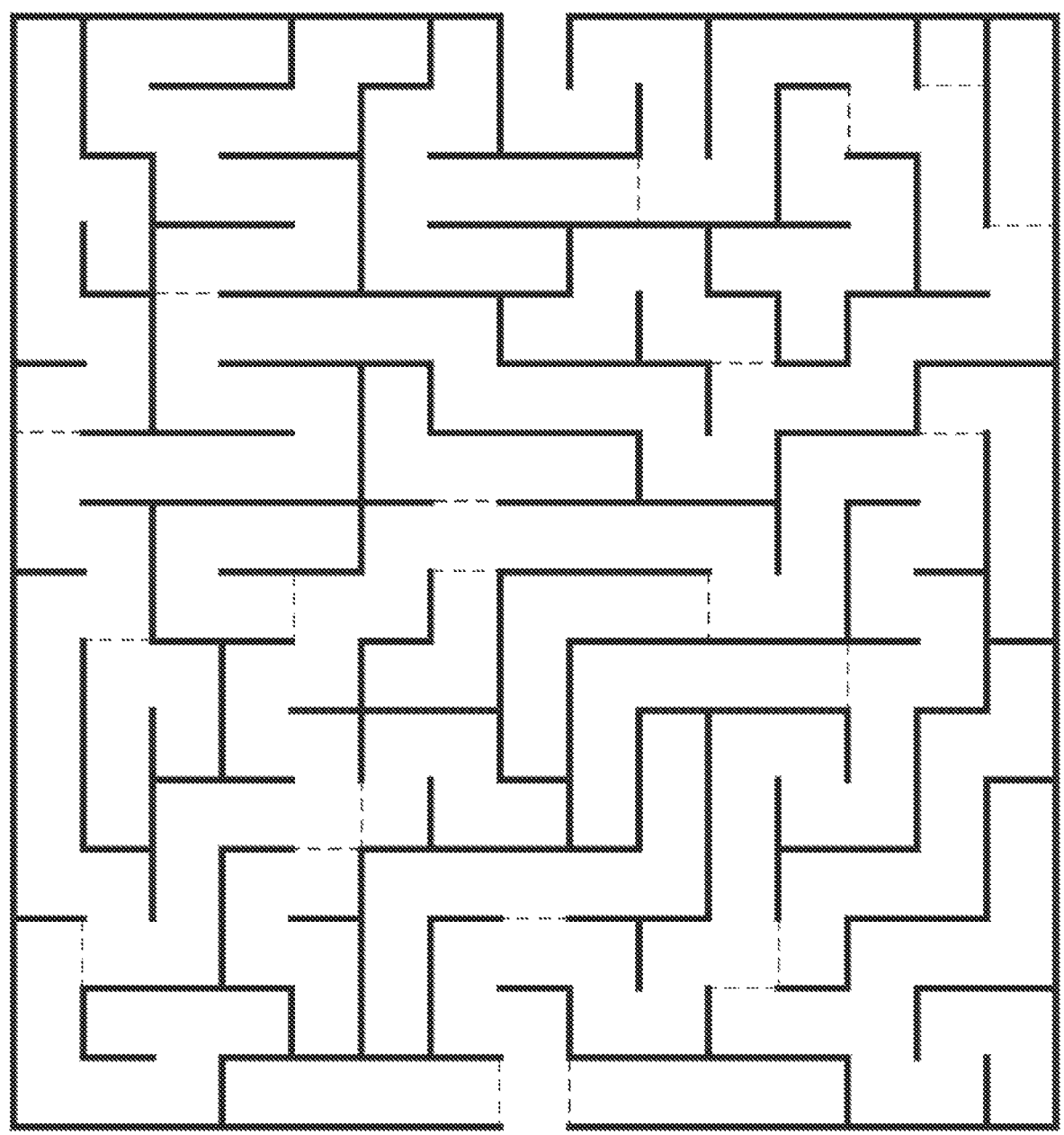
FIG. 25 is an illustration of a maze drawing task with decision points.

Referring to FIG. 25, the subject is then made to draw a path through a second, similar maze 2500 which has the same solution as the first maze 2400 but has a number of lines added or removed (e.g., the dashed lines of the second maze 2500) such that the second maze 2500 requires the subject to make decisions. Features (e.g., dynamic characteristics, incorrect decisions, etc.) of the subject's movement when drawing the path through the second maze 2500 are recorded. Since the subject has been primed and is familiar with the maze, the subject should be able to complete the second maze 2500 faster than if they hadn't been primed. Furthermore, the subject should be able to complete the second maze without pausing too often, taking too long, making too many incorrect decisions, and/or backtracking too far (i.e., over correcting) when an incorrect decision is made. If the subject has difficulties completing the second maze after being primed (as compared to a predetermined performance baseline or norm), they may have an executive dysfunction disorder or another disorder such as a short term memory defect. In some examples, a subject's performance in completing the second maze is objectively analyzed by comparing features associated with the subject's performance at decision points in the second maze to features associated with the subject's performance at non-decision points in the first maze corresponding to the decision points of the second maze. In other examples, features related to the subject's performance in completing the second maze is objectively analyzed by comparing features related to the subject's performance at different decision points of a single execution of the second maze.

In some examples, data is collected for normal subjects to establish a relationship between features of the first (priming) execution and the second execution. The features collected in two executions for a test subject are then assessed according to the established normal relationship. As a simple approach, distribution of percentage speedup (e.g., an average and standard deviation over a normal population) is used to determine if the test subject's percentage speedup close to that of the normal population. In some examples, multiple models including a model for a normal population and one or more models for populations with particular disorders are used, and the test subject is compared to the multiple models, for example, to determine a probability or other measure of match of the subject's features to each of the models.

Features of the execution of particular parts of the maze drawing task may also be used. For example, the "thinking" time, drawing speed, or other local feature in the vicinity of a decision point introduced in the second maze may provide an indication of the difficulty in recalling the previous run and/or determining the selection of the path to follow.

Other global features of the drawing task may be used as well, including average speed, thinking versus drawing cumulative time, and speed variation. Further, in the maze task, qualitative measures of compliance with rules such as staying within the marked paths (or equivalently deviations across boundaries) in the maze, extent and/or recovery of such deviations etc. may be informative.

As is the case with the clock drawing test, in some examples, to derive diagnostic information from the features of the movement when drawing a path through the second maze, a mapping between the features of the movement and diagnoses is made. To make the mapping, maze drawing test results for a group of known healthy subjects and a group of subjects known to have a neurocognitive disorder are collected. The maze drawing test results for both groups include features related to as dynamic characteristics of representational movements, incorrect decisions, and so on. The maze drawing test results are appropriately labeled as normal or disordered and are provided to a machine learning algorithm (e.g., a support vector machine training algorithm) which trains a model using the test results. In some examples, the model is represented as a set of model parameters. The trained model is provided to a classifier (e.g., a support vector machine) which, given a maze test result for a subject, can predict a diagnosis based on the maze test result.

In some examples, the entire set of maze drawing test results is provided to the machine learning algorithm to train the model. In other examples, an expert chooses certain features which are known to be correlated with certain diagnoses and only the chosen features are provided to the machine learning algorithm to train the model.

In some examples, additional features of maze drawing test results can be used to determine diagnoses. For example, an impaired test subject may have difficulty drawing a path through the maze which stays within the lines of the maze. For example, the impaired subject may run into a wall or cut through walls since head and eyes don't keep up with their hand.

In some examples, different degrees of decision points can be used to assess different levels of neurocognitive ability, where the term "degree" denotes a number of paths branching from a given decision point. For example, a first degree decision point might force a user to decide between two possible paths, of which one may be correct. A second degree decision point might force a user to decide between three possible paths, of which one may be correct. A third degree decision point might force a user to decide between four possible paths, of which one may be correct. Higher degree decision points are possible. In general, higher degree decision points are present in non-rectangular mazes.

Having multiple degrees of decision points is useful in assessing different levels of decision making abilities and/or difficulties. For example, a user with moderate decision making difficulties may exhibit little to no difficulties when confronted with a first degree decision point but may exhibit substantial difficulties when confronted with second and third degree decision points. In the rectangular second maze 2500 of FIG. 25, there are both first and second degrees at the decision points.

In some examples, decision making difficulty can be further stratified by providing embedded decision points where one decision point that leads to subsequent decision points even though all choices after the first choice lead to dead ends.

In some examples, mazes are specified such that they include at least some paths which result in a dead end after varying numbers of embedded choices. For example, in the simplest case, a maze may include a path where, after making a single decision, no more choices are required until a dead end is reached. For more complex cases, multiple decisions may present which eventually result in a dead end.

In some examples, all of the paths emanating from a decision point are balanced in that a distance from the decision point to an end of any dead end path connected to the decision point is equal to a distance from the decision point to any other dead end path connected to the decision point. Furthermore, a distance from the decision point to any other decision points (i.e., junctions) is equal to the distance from the decision point to the end of any of the dead ends connected to the decision point. By using a set of equally balanced correct and incorrect choices the test can assess the subject's level of decision making difficulty. Furthermore, differences due to scanning time can be reduced in the test.

In some examples, mazes are specified such that they have at least two decision points of each type, where a "type" is defined as a pairing of a degree and a number of embedded choices (e.g., a second degree decision point paired with no embedded decision points or a third degree decision point paired with a single embedded decision point).

in some examples, rather than only measuring completion time and motion characteristics for the entire maze, the maze is also divided into a number of sections, the motions through which can be individually measured and used in diagnostic assessments.

As is introduced above, a computer system which is used to administer the diagnostic tests described above can generate a diagnostic report for presentation of the results of a given diagnostic test. In some examples, the diagnostic report includes metrics which were determined from the execution of the diagnostic task. For example, a diagnostic report may include a test subject's time of completion for the second maze described above.

In other examples, the diagnostic report may include a processed version of the metrics determined from the execution of the diagnostic task. For example, the diagnostic report may include a ratio of a time of completion for the second maze described above to an average time of completion of the second maze for a number of prior completions of the maze (e.g., made by the same test subject or by one or more different test subjects). The ratio can be expressed as a percentage of completion time.

In other examples, the diagnostic report includes a diagnosis which is determined based on a particular combination of the metrics. For example, if a time of completion by a test subject of the second maze described above were considerably greater than an average time of completion for a number of prior completions of the second maze, a diagnosis indicating that the test subject has an executive dysfunction may be presented in the diagnostic report.

Figure 26:
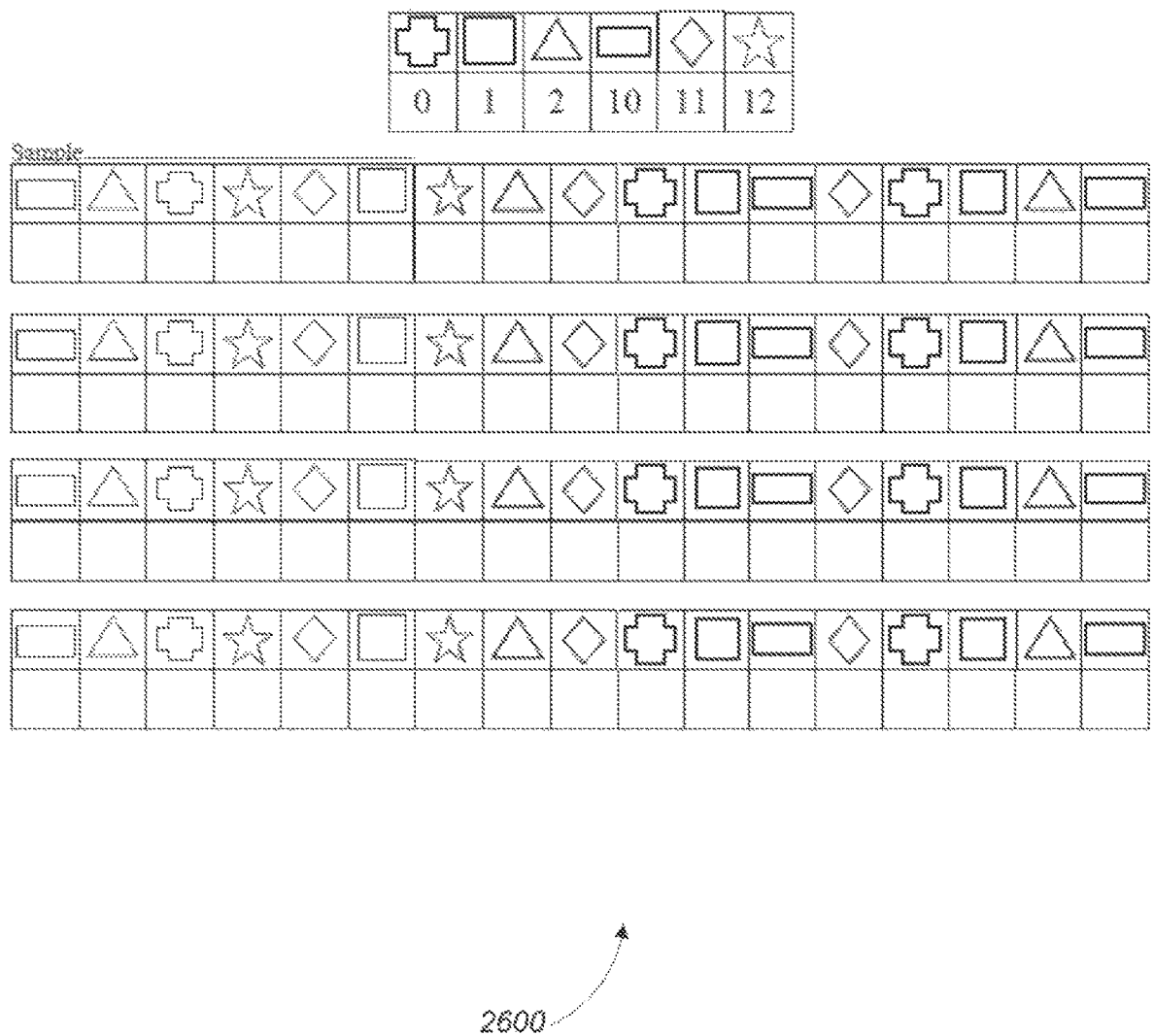
FIG. 26 is a symbol-digit test.

Referring to FIG. 26, a test conventionally referred to as a symbol-digit test requires a subject to write in the lower boxes in each row the digit corresponding to the symbol in the upper half of the row (i.e., as is given in the key at the top). Note that in FIG. 26, the symbol rows are all the same. However, in some examples each row is different.

In some examples, a subject's execution of the symbol-digit test is recorded in a digitized format which permits extraction of features such as test completion speed, decision latencies, and so on. In some examples, the digitized recording of the subject's execution of the test also permits semi-automated scoring of the test (i.e., the program) makes educated guesses as to whether the subject's answer is the expected answer, and the educated guess is confirmed by a human.

Figure 27:
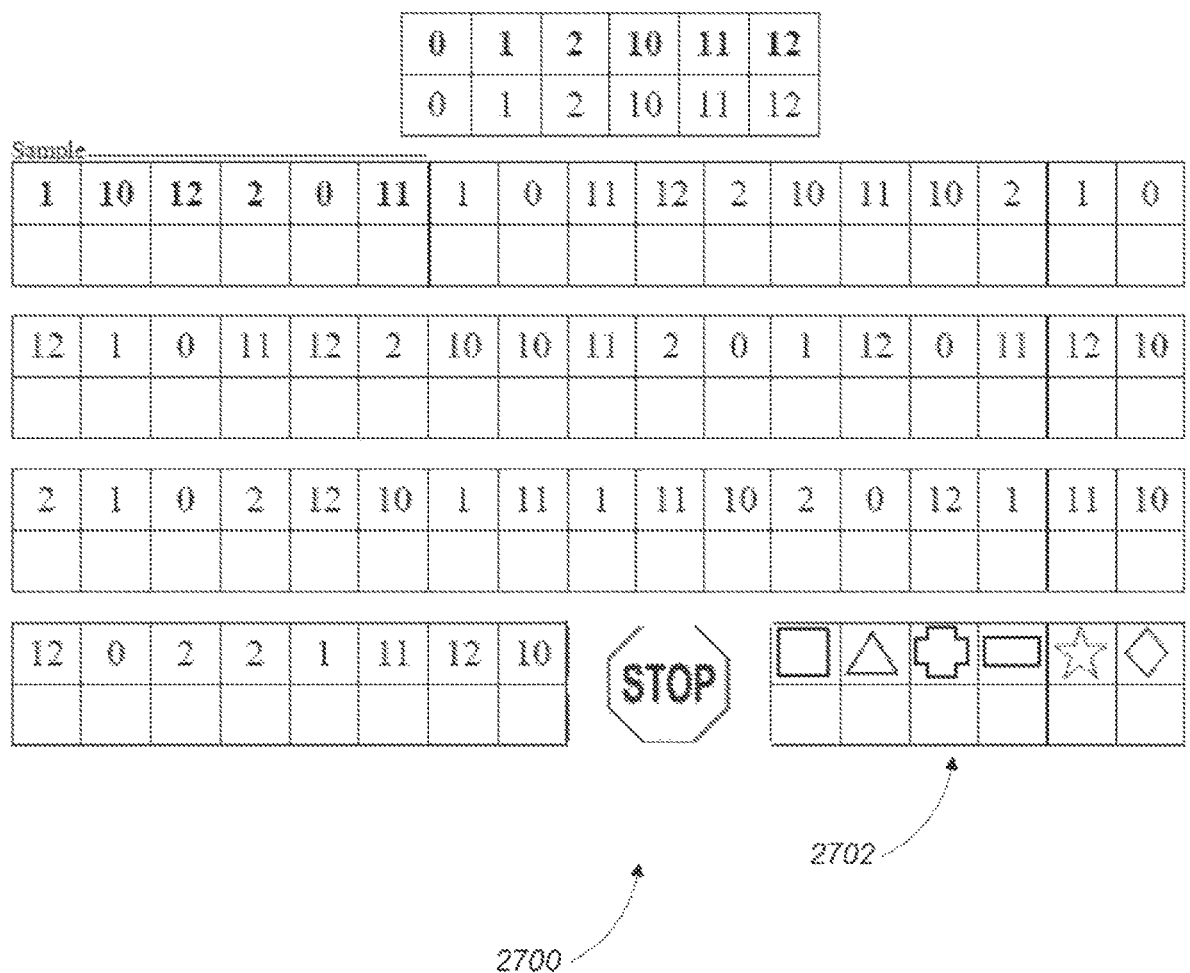
FIG. 27 is a digit-digit test.

Referring to FIG. 27, a test referred to as the digit-digit task requires a user to write in the bottom halves of the rows the digits in the top halves. Again, the subject's execution of the task can be recorded in a digitized format and features such as hooklets, completion time, decision latencies, and so on can be extracted from the recording. The digit-digit task can also be semi-automatically scored as is described above.

In some examples, the two tests described above include 6 different cues (i.e., the shapes in the top half, the digits themselves in the bottom half), and (unknown to the subject) each six successive blocks in each test contains a permutation of the six cues (so that every six stimuli you encounter contains all the stimuli).

In some examples, both of the two tests described above are given to the subject in succession. In some examples, this is accomplished by printing both tests on a sheet of paper and folding the paper in half so the subject sees only one of the tests at a given time.

When the subject is finished with both tests, they are asked to complete a final portion 2702 of the test in which they are asked produce, from memory, the numbers that correspond to the symbols shown at bottom right without having a symbol to digit key available.

Various features related to dynamic characteristics and correctness of the subject's execution of the test can be extracted from the recording of the subjections execution of the test.

It is to be understood that the foregoing description is intended to illustrate and not to limit the scope of the invention, which is defined by the scope of the appended claims. Other embodiments are within the scope of the following claims.

What is claimed is:

1. A computer-implemented method comprising:
providing a first task to a subject in a medical context;
monitoring a performance of the first task by the subject using one or more sensors;
collecting first data corresponding to individual representational motions made by the subject during the performance of the first task;
analyzing the first data, using a machine learning algorithm trained with a set of training data including prior performances of the first task, to classify the individual representational motions and identify a plurality of elements of the individual representational motions; and evaluating one or more medical characteristics of the subject based on the plurality of elements of the individual representational motions.

2. The computer-implemented method of claim 1, wherein the first task includes a graphomotor diagnostic task.

3. The computer-implemented method of claim 2, wherein the graphomotor diagnostic task includes a clock drawing test.

4. The computer-implemented method of claim 3, wherein at least some of the plurality of elements correspond to one or more element types including one or more of hour labels, an hour hand, a minute hand, a second hand, a clock face outline, and a clock face center point.

5. The computer-implemented method of claim 1, wherein the one or more sensors include motion sensors configured to capture one or more aspects of the individual representational motions made by the subject during the performance of the first task.

6. The computer-implemented method of claim 5, wherein at least one of the one or more sensors is physically associated with the subject during at least a portion of the performance of the first task.

7. The computer-implemented method of claim 5, wherein at least one of the one or more sensors is associated with a surface upon which the first task is performed.

8. The computer-implemented method of claim 5, wherein the first data comprises data representing subject motion characteristics, the subject motion characteristics including one or more of a change of position relative to a reference point, a velocity of the change of position, an acceleration of the velocity of the change of position, a first duration of a first motion relative to a second duration of a second motion, a distance between an observed initial position and an expected initial position, and a distance between an observed ending position and an expected ending position.

9. The computer-implemented method of claim 1, wherein the one or more medical characteristics include at least one of motor skills or cognitive skills.

10. The computer-implemented method of claim 1, wherein evaluating one or more medical characteristics of the subject includes providing a second task to the subject and comparing the performance of the first task with a performance of the second task.

11. A non-transitory computer-readable medium storing instructions that, when executed by one or more computing devices, cause the one or more computing devices to perform a method for assessing a subject by processing individual representational motions, the method comprising:
provinding a first task to a subject in a medical context;
monitoring a performance of the first task by the subject using one or more sensors;
collecting first data corresponding to individual representational motions made by the subject during the performance of the first task;
analyzing the first data, using a machine learning algorithm trained with a set of training data including prior performances of the first task, to classify the individual representational motions and identify a plurality of elements of the individual representational motions; and
evaluating one or more medical characteristics of the subject based on the plurality of elements of the individual representational motions.

12. The non-transitory computer-readable medium of claim 11, wherein the first task includes a graphomotor diagnostic task.

13. The non-transitory computer-readable medium of claim 12, wherein the graphomotor diagnostic task includes a clock drawing test.

14. The non-transitory computer-readable medium of claim 13, wherein at least some of the plurality of elements correspond to one or more element types including one or more of hour labels, an hour hand, a minute hand, a second hand, a clock face outline, and a clock face center point.

15. The non-transitory computer-readable medium of claim 11, wherein the one or more sensors include motion sensors configured to capture one or more aspects of the individual representational motions made by the subject during the performance of the first task, and wherein at least one of the one or more sensors is physically associated with the subject during at least a portion of the performance of the first task.

16. The non-transitory computer-readable medium of claim 15, wherein at least one of the one or more sensors is associated with a surface upon which the first task is performed.

17. The non-transitory computer-readable medium of claim 15, wherein the first data comprises data representing subject motion characteristics, the subject motion characteristics including one or more of a change of position relative to a reference point, a velocity of the change of position, an acceleration of the velocity of the change of position, a first duration of a first motion relative to a second duration of a second motion, a distance between an observed initial position and an expected initial position, and a distance between an observed ending position and an expected ending position.

18. The non-transitory computer-readable medium of claim 11, wherein evaluating one or more medical characteristics of the subject includes providing a second task to the subject and comparing the performance of the first task with a performance of the second task.

19. A system for assessing a subject by processing individual representational motions, the system including:
a data storage device that stores instructions for assessing a subject by processing individual representational motions; and
a processor configured to execute the instructions to perform a method including:
providing a graphomotor diagnostic task to a subject in a medical context;
monitoring a performance of the graphomotor diagnostic task by the subject using one or more sensors;
collecting first data corresponding to individual representational motions made by the subject during the performance of the graphomotor diagnostic task;
analyzing the first data, using a machine learning algorithm trained with a set of training data including prior performances of the graphomotor diagnostic task, to classify the individual representational motions and identify a plurality of elements of the individual representational motions; and
evaluating one or more medical characteristics of the subject based on the plurality of elements of the individual representational motions.

20. The system of claim 19, wherein the one or more sensors include motion sensors configured to capture one or more aspects of the individual representational motions made by the subject during the performance of the graphomotor diagnostic task, and wherein:

at least one of the one or more sensors is configured to be physically associated with the subject during at least a portion of the performance of the graphomotor diagnostic task; and at least one of the one or more sensors is associated with a surface upon which the graphomotor diagnostic task is performed.

* * * * *